United States Patent
Wan et al.

(10) Patent No.: US 12,275,753 B2
(45) Date of Patent: Apr. 15, 2025

(54) GLYCOSYLATION METHOD INVOLVING TRIVALENT IODINE REAGENT

(71) Applicant: HUAZHONG UNIVERSITY OF SCIENCE AND TECHNOLOGY, Hubei (CN)

(72) Inventors: Qian Wan, Hubei (CN); Lingkui Meng, Hubei (CN); Jing Zeng, Hubei (CN); Yulin Tan, Hubei (CN); Yue Yin, Hubei (CN); Qin Zhang, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 18/964,637

(22) Filed: Dec. 1, 2024

(65) Prior Publication Data
US 2025/0092075 A1  Mar. 20, 2025

Related U.S. Application Data

(63) Continuation of application No. PCT/CN2023/131488, filed on Nov. 14, 2023.

(30) Foreign Application Priority Data

Apr. 20, 2023 (CN) .......................... 202310427740.2

(51) Int. Cl.
| | |
|---|---|
| C07H 1/00 | (2006.01) |
| C07H 15/04 | (2006.01) |
| C07H 15/12 | (2006.01) |
| C07H 15/14 | (2006.01) |
| C07H 15/18 | (2006.01) |
| C07H 15/207 | (2006.01) |
| C07H 17/07 | (2006.01) |
| C07H 19/04 | (2006.01) |
| C07H 19/052 | (2006.01) |
| C07H 19/06 | (2006.01) |
| C07H 19/16 | (2006.01) |
| C07H 19/23 | (2006.01) |

(52) U.S. Cl.
CPC .............. *C07H 1/00* (2013.01); *C07H 15/04* (2013.01); *C07H 15/12* (2013.01); *C07H 15/14* (2013.01); *C07H 15/18* (2013.01); *C07H 15/207* (2013.01); *C07H 17/07* (2013.01); *C07H 19/04* (2013.01); *C07H 19/052* (2013.01); *C07H 19/06* (2013.01); *C07H 19/16* (2013.01); *C07H 19/23* (2013.01)

(58) Field of Classification Search
None
See application file for complete search history.

(56) References Cited

FOREIGN PATENT DOCUMENTS

| CN | 102127135 | 7/2011 |
| CN | 114163483 | 3/2022 |
| CN | 114891049 | 8/2022 |
| CN | 116554245 | 8/2023 |

OTHER PUBLICATIONS

Chu et al. Org. Lett. (2014), vol. 16, pp. 1780-1782.*
Lingkui Meng et al., "Glycosylation Enabled by Successive Rhodium(II) and Brønsted Acid Catalysis", Journal of the American Chemical Society, Jul. 17, 2019, pp. 11775-11780, vol. 141, Issue 30.
G.H. Veeneman et al., "Iodonium ion promoted reactions at the anomeric centre. II An efficient thioglycoside mediated approach toward the formation of 1,2-trans linked glycosides and glycosidic esters", Tetrahedron Letters, 1990, pp. 1331-1334, vol. 31, Issue 9.
"International Search Report (Form PCT/ISA/210) of PCT/CN2023/131488," mailed on Feb. 18, 2024, with English translation thereof, pp. 1-7.
"Written Opinion of the International Searching Authority (Form PCT/ISA/237) of PCT/ CN2023/131488," mailed on Feb. 18, 2024, with English translation thereof, pp. 1-10.

* cited by examiner

*Primary Examiner* — Patrick T Lewis
(74) *Attorney, Agent, or Firm* — JCIPRNET

(57) ABSTRACT

A glycosylation method involving a trivalent iodine reagent, wherein a glycosyl donor (I) is activated in the presence of a trivalent iodine reagent and a transition metal catalyst, and then reacts with a acceptor (II) under acid catalysis or directly to obtain a glycosylation product (III); in the glycosyl donor (I), Gly is a glycosyl group in which one or more hydroxyl groups on the sugar ring are protected by a protecting group; X is an oxygen, sulfur, or selenium atom; R is an alkyl group or an aryl group; the acceptor (II) is a nucleophile selected from sugars, alcohols, phenols, flavonoids, carboxylic acids, phosphates, pyrimidines, purines, amides, sulfonamides, guanidines, arylamines, indoles, enol silyl ethers, thiols, or thiophenol containing one or more free hydroxyl groups.

12 Claims, No Drawings

GLYCOSYLATION METHOD INVOLVING TRIVALENT IODINE REAGENT

CROSS-REFERENCE TO RELATED APPLICATION

This application is a continuation of international application of PCT application serial no. PCT/CN2023/131488, filed on Nov. 14, 2023, which claims the priority benefit of China application no. 202310427740.2, filed on Apr. 20, 2023. The entirety of each of the above-mentioned patent applications is hereby incorporated by reference herein and made a part of this specification.

TECHNICAL FIELD

The disclosure belongs to the technical field of carbohydrate chemistry, and more specifically, relates to a glycosylation method involving a trivalent iodine reagent, and in particular to a glycosylation method involving a trivalent iodine reagent and the activation of a glycosyl donor by a transition metal catalyst and an acid.

DESCRIPTION OF RELATED ART

Carbohydrates are one of the four important types of biological molecules involved in the essence of life activities, which are widely distributed in animals, plants, microorganisms, and viruses, and play an important role in organisms. Studies have shown that carbohydrates have good application prospects in many fields such as anti-cancer, anti-inflammatory, anti-viral, anti-diabetic, immune regulation, and organ transplantation. Therefore, establishing an efficient method for synthesis of carbohydrates is of great significance for studying the biological functions of natural carbohydrates and developing new carbohydrate-based drugs and vaccines. The key to the synthesis of carbohydrates is to efficiently construct glycosidic bonds through glycosylation reactions. However, since the first glycosylation reaction was discovered in 1879, although carbohydrate chemists have developed dozens of different modes of glycosylation reactions, there is still a lack of mild, efficient, and widely applicable glycosylation methods. Many carbohydrates with good biological activity lack effective glycosylation methods for their chemical synthesis, which highly hinders the research of carbohydrates and the development of new carbohydrate drugs.

Over the past 100 years, chemists have developed a series of of different types of glycosyl donors, including halogenated sugars, glycosyl hemiacetals, acetates, glycans, thioglycosides, selenoglycosides, trichloroacetimidates, and o-alkynyl benzoates, in which thioglycosides, selenoglycosides, and oxygenglycoside are the most commonly used glycosyl donors in carbohydrate chemical synthesis due to the advantages, such as easy preparation and long storage life. The activation reagents (or methods) of the thioglycoside and selenoglycoside donors in the glycosylation methods mainly fall into the following four categories: metal salts, halonium ion reagents, sulfonium ion reagents, and single electron transfer reagents/methods. The methodologies under discussion frequently employ metal salts, particularly heavy metal salt activators, in the earlier stages. These activators typically necessitate stoichiometric quantities, and the reaction conditions are often severe. This approach is associated with several challenges, including high toxicity, complications in post-treatment, and inadequate reproducibility of the reactions. While certain glycosylation techniques utilizing halonium and sulfonium ion reagents have gained considerable traction, they generally require the use of excessive amounts of promoters for effective activation. Furthermore, many of these promoters are both costly and toxic, and the reaction conditions are not sufficiently mild, leading to poor compatibility with the reactants. Although there have been some investigations into single electron transfer reagents and methods, the research in this area remains underdeveloped and lacks depth, resulting in a limited range of applications. The applicant team also reported a method for sequentially catalyzing (H+) activation of thioglycosides using metal Rh catalysts and Brønsted acids (J. Am. Chem. Soc. 2019, 141, 11775-11780), compared with the method of the disclosure, the Rh/H+-catalyzed thioglycoside activation method has the following problems: only precious metal rhodium salts can be used, and the activation of some thioglycosides requires a higher catalytic equivalent of Rh catalyst. In addition, azo reagents with explosion risks need to be used, and the scope of application of glycosyl acceptors is limited.

The demand for carbohydrate compounds, especially in the context of synthesizing complex carbohydrates, is experiencing a consistent increase. Nevertheless, current methodologies and technologies present challenges in the chemical synthesis of a substantial array of carbohydrates that possess significant application value and developmental potential. Consequently, the advancement of a mild and efficient glycosylation technique utilizing thioglycosides and selenoglycosides as glycosyl donors holds considerable importance in the field of carbohydrate chemical synthesis.

SUMMARY OF INVENTION

In light of the previously identified deficiencies and areas for enhancement in current methodologies, the objective of this disclosure is to introduce a novel glycosylation technique. This method employs a trivalent iodine reagent to activate the glycosyl donor, thereby circumventing the necessity for hazardous azo reagents and costly transition-metal catalysts. The proposed glycosylation method is characterized by its mild conditions, efficiency, ease of operation, cost-effectiveness, and broad applicability.

According to the above purpose, the disclosure provides a glycosylation method involving a trivalent iodine reagent and transition metal catalyst: a glycosyl donor (I) is activated by a mixture of trivalent iodine reagent and a transition metal catalyst, and then reacts with an acceptor (II) under acid catalysis or directly to deliver a glycosylation product (III).

The reaction equation is as follows:

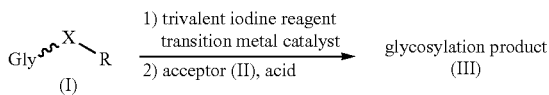

In the equation, in the glycosyl donor (I), Gly is a glycosyl group in which one or more hydroxyl groups on the sugar ring are protected by a protecting group; X is an oxygen (O), sulfur (S), or selenium (Se) atom; and R is an alkyl group or an aryl group.

In the glycosyl donor (I), when R is an alkyl group, the alkyl group is preferably selected from ethyl (Et), isopropyl (iPr), benzyl (Bn); when R is an aryl group, the aryl group is preferably selected from phenyl (Ph), p-methylphenyl (Tol), or 2-ethylphenyl (°EP).

The glycosyl (Gly) is selected from one of the structures represented by a formula (I-a) or a formula (I-b), in which the substituent on the sugar ring may be hydrogen, an alkyl group, an alkoxy group, an acyloxy group, a siloxy group, a substituted amino group, a cyclic acetal group, a cyclic ketal group, or a glycosyl group.

Preferably, the formula (I-a) is selected from a compound of any of the following structures:

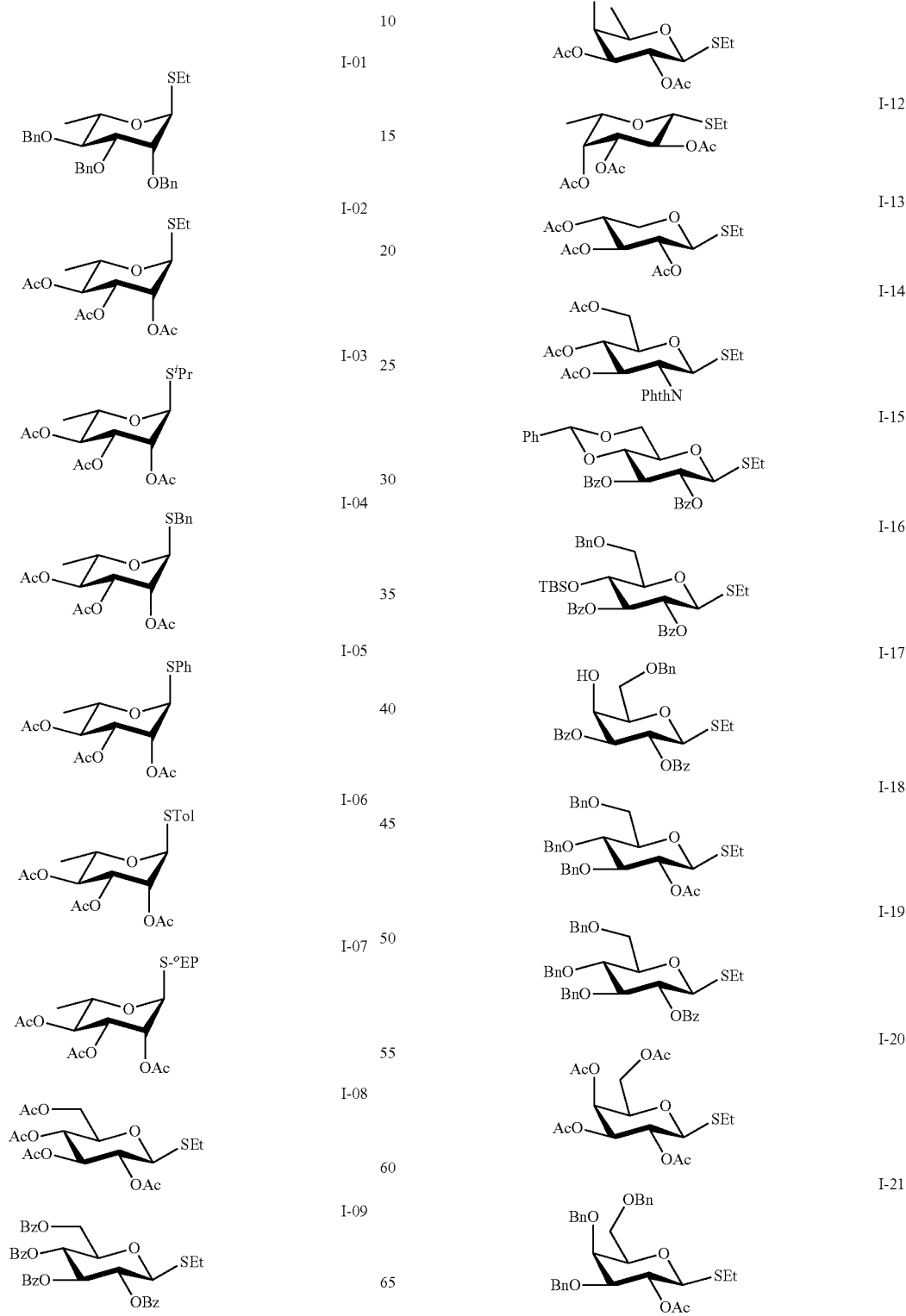

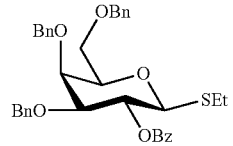
I-22

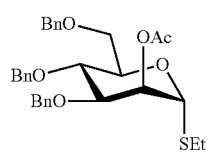
I-23

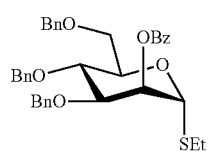
I-24

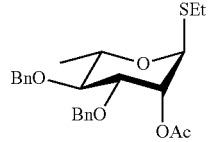
I-25

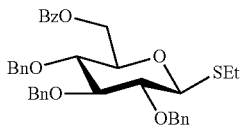
I-26

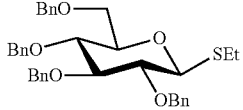
I-27

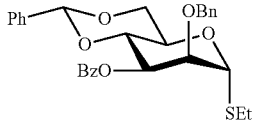
I-28

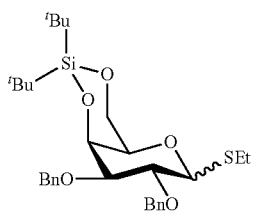
I-29

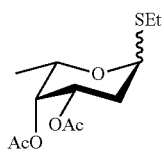
I-30

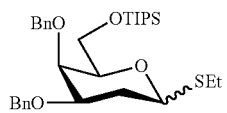
I-31

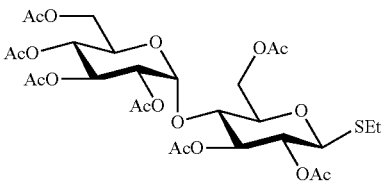
I-32

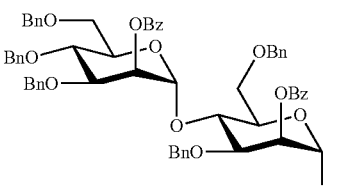
I-33

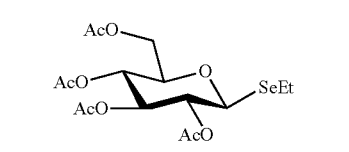
I-34

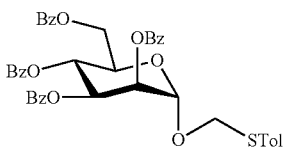
I-35

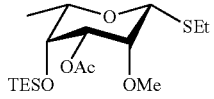
I-36

Preferably, the formula (I-b) is selected from a compound of any of the following structures:

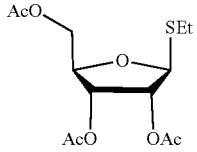
I-37

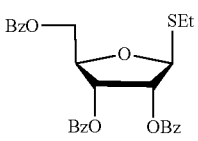
I-38

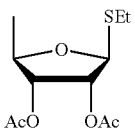
I-39

The glycosyl acceptor (II) is a nucleophile Nu-H, with the nucleophile selected from sugars, alcohols, phenols, flavonoids, carboxylic acids (no need to add additional acid in this case), phosphates, pyrimidines, purines, amides, sulfonamides, guanidines, arylamines, indoles, enol silyl ethers, thiols, or thiophenols containing one or more free hydroxyl groups.

Preferably, the glycosyl acceptor containing one or more free hydroxyl groups is selected from a compound of any of the following structures:

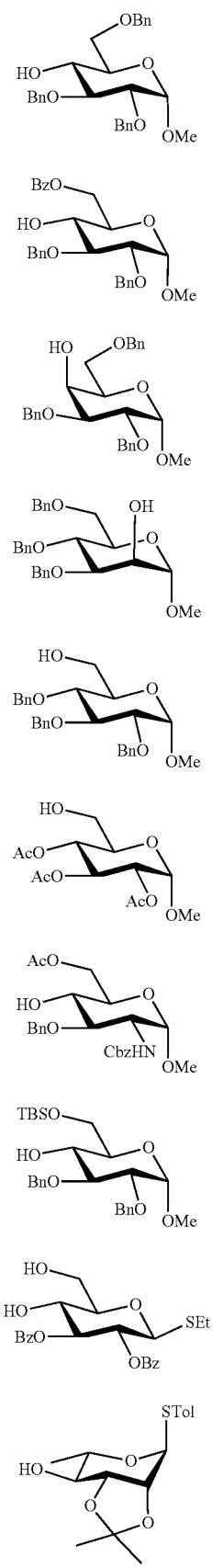
II-01
II-02
II-03
II-04
II-05
II-06
II-07
II-08
II-09
II-10
-continued
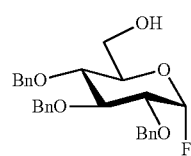
II-11
Preferably, the alcohol or phenol acceptor is selected from a compound of any of the following structures:
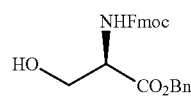
II-12
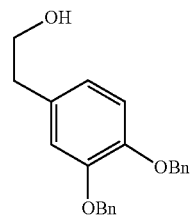
II-13
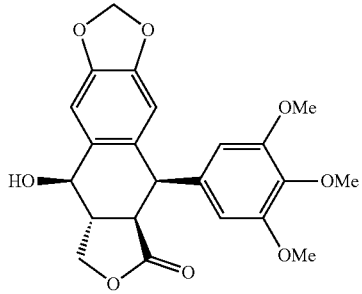
II-14
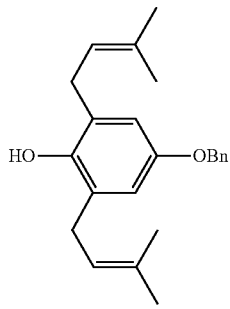
II-15
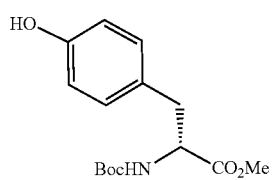
II-16
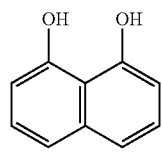
II-17
Preferably, the flavonoid acceptor is selected from a compound of the following structure:

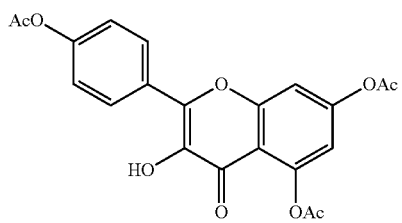
II-18

Preferably, the carboxylic acid or phosphate acceptor is selected from a compound of the following structure:

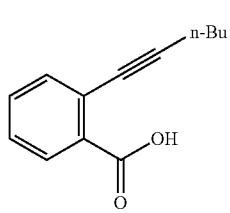
II-19

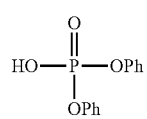
II-20

Preferably, the pyrimidine acceptor is selected from a compound of any of the following structures:

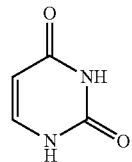
II-21

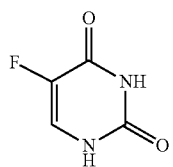
II-22

II-23

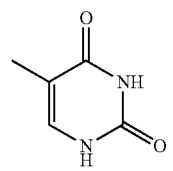
II-24

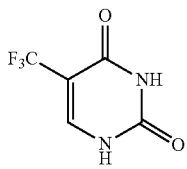
II-25

II-26

Preferably, the purine acceptor is selected from a compound of any of the following structures:

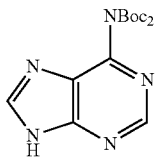
II-27

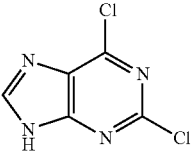
II-28

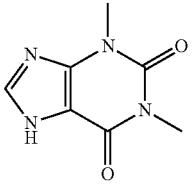
II-29

Preferably, the amide acceptor is selected from a compound of any of the following structures:

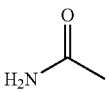
II-30

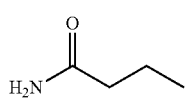
II-31

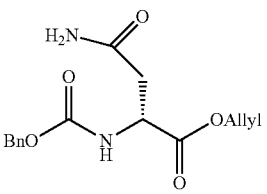
II-32

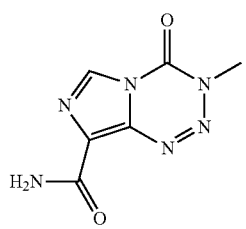
II-33

II-34

II-35

Preferably, the sulfonamide acceptor is selected from a compound of the following structure:

II-36

Preferably, the guanidine acceptor is selected from a compound of the following structure:

II-37

Preferably, the arylamine acceptor is selected from a compound of the following structure:

II-38

Preferably, the indole acceptor is selected from a compound of the following structure:

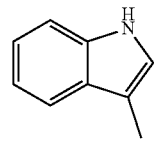
II-39

Preferably, the enol silyl ether acceptor is selected from a compound having any of the following structures:

II-40

II-41

Preferably, the thiol or thiophenol acceptor is selected from a compound of any of the following structures:

II-42

II-43

The trivalent iodine reagent is selected from the iodine ylide reagent represented by formula (IV-a) and the imino iodide represented by formula (IV-b). In the formula, $R^1$ and $R^2$ are alkyl acyl (alkyl-CO), aryl formyl (ArCO), alkyl sulfonyl (alkyl-SO$_2$), aryl sulfonyl (ArSO$_2$), alkoxy acyl (alkyl-OCO), phenoloxy acyl (ArO—CO) the same or independent of each other, for example; $R^3$ is a sulfonyl group, preferably a p-toluenesulfonyl group (Ts); Ar is an aryl group, preferably selected from a phenyl group (Ph), a 2-methoxyphenyl group (o-OMe-Ph), or a 2-nitrophenyl group (o-NO$_2$—Ph).

(IV-a)

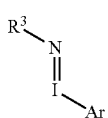
(IV-b)

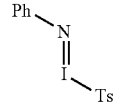
IV-8

Preferably, the iodine ylide represented by formula (IV-a) is selected from a compound of any of the following structures:

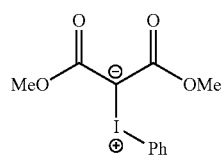
IV-1

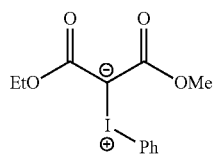
IV-2

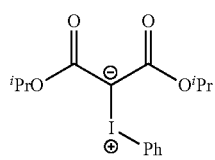
IV-3

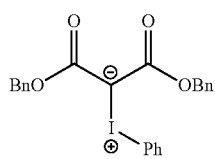
IV-4

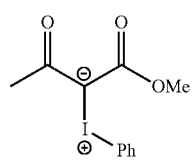
IV-5

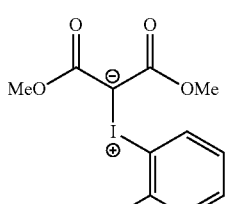
IV-6

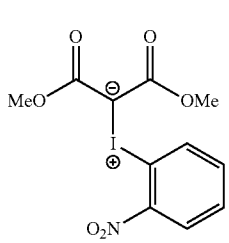
IV-7

Preferably, the imino iodide represented by formula (IV-b) is:

More preferably, the trivalent iodine reagent is an iodine ylide reagent represented by formula (IV-1).

In an embodiment, the molar ratio of the glycosyl acceptor represented by formula (II) to the trivalent iodine reagent may be 1:(1-6), preferably 1:(1-4), such as 1:(1.3-3), such as 1:(1.5-2).

The transition metal catalyst is a substance containing copper or rhodium, in which the copper-containing substance is selected from copper inorganic acid salts, copper organic acid salts, and copper complexes, for example, selected from cuprous chloride (CuCl), cuprous bromide (CuBr), cuprous iodide (CuI), cuprous bromide·dimethyl sulfide (CuBr—SMe$_2$), cuprous tetrafluoroborate tetraacetonitrile (Cu(MeCN)$_4$BF$_4$), cuprous trifluoromethanesulfonate (CuOTf), cuprous acetate (CuOAc), cuprous hexafluoroacetylacetonate ·1,5-cyclooctadiene (Cu(hfacac) (cod)), cuprous chloride [1,3-bis(2,6-diisopropylphenyl) imidazole-2-ylidene]((iPr)CuCl), cuprous diphenyl phosphate (Ph$_2$PO$_2$Cu), cuprous thiophene-2-carboxylate (CuTc), cupric chloride (CuCl$_2$), cupric bromide (CuBr$_2$), cupric acetate (Cu(OAc)$_2$), copper acetylacetonate (Cu(acac)$_2$), copper(II) hexafluoroacetylacetonate (Cu(hfacac)$_2$), copper(II) p-toluenesulfonate (Cu(OTs)$_2$), copper(II) trifluoromethanesulfonate (Cu(OTf)$_2$), copper(II) sulfate (CuSO$_4$), cuprous trifluoromethanesulfonate toluene complex ((CuOTf)$_2$·Toluene); the rhodium-containing substance is selected from rhodium (II) acetate dimer (Rh$_2$(OAc)$_4$) and rhodium (II) octanoate dimer (Rh$_2$(oct)$_4$). Preferably, the transition metal catalyst is selected from CuCl, CuBr, CuI, CuBr·SMe$_2$, Cu(MeCN)$_4$BF$_4$, CuOTf, CuOAc, (iPr)CuCl, Ph$_2$PO$_2$Cu, CuTc, CuCl$_2$, CuBr$_2$, Cu(OAc)$_2$, Cu(acac)$_2$, Cu(OTf)$_2$, (CuOTf)$_2$·Toluene, Rh$_2$(OAc)$_4$, Rh$_2$(oct)$_4$; more preferably selected from CuCl, CuBr, CuI, CuTc, Cu(MeCN)$_4$BF$_4$, and CuBr$_2$, and most preferably selected from CuCl and CuBr.

In an embodiment, the amount of the transition metal catalyst is 0.01-10% of the glycosyl acceptor in mole percentage (mol %), for example, 0.01%, 0.025%, 0.05%, 0.1%, 0.25%, 0.5%, 5%, 10%, and any numerical value within the interval range or range formed by the arbitrary values, such as 0.01-5%, such as 0.1-1%, and such as 0.25-0.5%.

The acid catalyst is selected from Brønsted acid or Lewis acid. For example, the Brønsted acid is selected from methanesulfonic acid (MsOH), p-toluenesulfonic acid (TsOH), camphorsulfonic acid (CSA), trifluoromethanesulfonic acid (TfOH), trifluoromethanesulfonic acid-2,5-di-tert-butylpyridinium salt (TfOH·DTBP), trifluoromethanesulfonic acid-2,5-di-tert-butyl-4-methylpyridinium salt (TfOH·DTBMP), pyridinium trifluoromethanesulfonate (TfOH·Pyr), diisopropylamine trifluoromethanesulfonate (TfOH·iPr$_2$NH), tetrafluoroboric acid ethyl ether (HBF$_4$·Et$_2$O), bistrifluoromethanesulfonimide (Tf$_2$NH); the Lewis acid is selected from boron trifluoride etherate (BF$_3$·Et$_2$O), tris(pentafluorophenyl)borane (BCF), trimethylsilyl trifluoromethanesulfonate (TMSOTf), triethylsilyl trifluoromethanesulfonate (TESOTf), copper(II) trifluoromethanesulfonate (Cu(OTf)$_2$), cuprous trifluoromethanesulfonate (CuOTf), trityltetrakis(pentafluorophenyl)borate (Ph$_3$CB(C$_6$F$_5$)$_4$). Preferably, the acid is selected from TfOH, TfOH·DTBP, Tf$_2$NH, TMSOTf, Cu(OTf)$_2$, BF$_3$·Et$_2$O or the acidic substrate (carboxylic acid) is used to promote the glycosylation reaction without adding additional acid; more preferably, the acid is selected from TfOH, TMSOTf, and TfOH·DTBP.

Preferably, in terms of mole percent (mol %), the amount of the acid is 5-30%, such as 5-25%, such as 10%-25%, such as 10-20%, of the glycosyl acceptor. When the glycosyl acceptor (II) is a carboxylic acid, the amount of the acid used may be 0.

Preferably, the reaction is carried out in an organic solvent. The organic solvent may be selected from dichloromethane, chloroform, 1,2-dichloroethane, benzene, toluene, acetonitrile, and tetrahydrofuran of a combination of two or more of these solvents. Preferably, the organic solvent is selected from dichloromethane, chloroform, 1,2-dichloroethane, or a combination thereof. Specifically, the reaction solvent may be selected by persons skilled in the art based on common knowledge.

The reaction temperature is range from −78° C. to 30° C., for example, −60° C., −40° C., −20° C., −10° C., 0° C., 10° C., 25° C. or any range of the temperature values, preferably −78° C. to 25° C., such as −78° C. to 0° C., such as −60° C. to 0° C., such as −40° C. to 0° C., and such as −10° C. to 0° C. Specifically, the reaction temperature may be selected by persons skilled in the art based on common knowledge.

In general, the above technical solution conceived by the disclosure has the following technical advantages compared with the related art:

(1) The reaction of the disclosure is mild and efficient, and avoids the use of dangerous azo reagents and expensive metal catalysts.

(2) The disclosure exhibits a broad operational temperature range and accommodates a diverse array of trivalent iodine reagents, transition metal catalysts, and acids. This versatility facilitates the efficient glycosylation of various active substrates. Furthermore, the approach demonstrates significant applicability across a wide spectrum of substrates, effectively engaging glycosyl donors and acceptors of differing types and structural configurations.

(3) The trivalent iodine reagent used in the disclosure may be prepared rapidly and in large quantities at a low cost.

(4) The transition metal catalyst referenced in this disclosure may be chosen from widely available, cost-effective, and abundant metal salts or complexes that exhibit low toxicity and necessitate a reduced quantity of catalyst for effective application.

(5) The acid catalyst used in the disclosure may be selected from commercially available Brønsted acids or Lewis acids.

(6) The donor used in the disclosure may be thioglycoside, selenoglycoside, or oxygenoglycoside donor with mature synthesis technology, stable properties, easy preparation and storage.

In summary, the glycosylation method involving the trivalent iodine reagent provided by the disclosure effectively overcomes the problems existing in the existing methods, such as harsh reaction conditions, narrow substrate applicability or complex donor structure that is difficult to prepare, poor donor stability and difficult to store, and the disclosure provides a new and easy-to-implement solution for the synthesis of carbohydrates.

DESCRIPTION OF THE EMBODIMENTS

In order to make the purpose, technical solutions, and advantages of the disclosure more clearly understood, the disclosure is further described in detail below together with the accompanying drawings and embodiments. It should be understood that the specific embodiments described herein are only used to explain the disclosure, and the embodiments are not used to limit the disclosure. In addition, the technical features involved in the various embodiments of the disclosure described below may be combined with each other as long as the features do not conflict with each other.

Unless otherwise specified, the raw materials and reagents used in the disclosure are commercially available. All reagents were of commercial grade and used as received. All moisture-sensitive reactions were performed under argon atmosphere. The reaction was monitored by thin layer chromatography (TLC) and detected by ultraviolet absorption (254 nm). If necessary, a 10% by volume ethanol solution of sulfuric acid was sprayed, and carbonization was performed at 80-150° C. for color development. Flash column chromatography uses silica gel H. $^1$H and $^{13}$C NMR spectra were recorded on a Bruker AV 400 and Bruker Av 600 using deuterated chloroform (CDCl$_3$) as the deuterated reagent. Chemical shifts (δ) are expressed in ppm with tetramethylsilane as the internal standard. Coupling constants (J) are expressed in Hz.

Unless otherwise specified, scientific and technical terms and abbreviations used in the disclosure have the meanings commonly understood by persons skilled in the art. For example, "equivalent" in the disclosure refers to the ratio of the amount of each substance involved in the reaction; for another example, the meanings of some abbreviations are as follows:

| Abbreviation | Meaning | Abbreviation | Meaning |
|---|---|---|---|
| Me | Methyl | Nap | Naphthylmethyl |
| Et | Ethyl | Ns | p-Nitrobenzenesulfonyl |
| iPr | Isopropyl | Ph | Phenyl |
| Ac | Acetyl | Phth | Phthaloyl |
| Bn | Benzyl | TBS | tert-Butyldimethylsilyl |
| Bz | Benzoyl | TBDPS | tert-Butyldiphenylsilyl |
| tBu | Tert-butyl | TMS | Trimethylsilyl |
| Boc | tert-Butyloxycarbonyl | TIPS | Triisopropylsilyl |
| n-Bu | n-Butyl | Tol | Toluene |
| Cbz | Benzyloxycarbonyl | Ts | p-Toluenesulfonyl |
| Fmoc | Fmoc | Tf | Trifluoromethanesulfonyl |
| MeCN | Acetonitrile | DCE | 1,2-Dichloroethane |
| MsOH | Methanesulfonic acid | BSTFA | Bis(trimethylsilyl)trifluoroacetamide |

The glycosylation method of the disclosure comprises steps of: mixing a glycosyl donor (I) with a trivalent iodine reagent, adding a transition metal catalyst to perform a pre-activation reaction, and then adding an acceptor (II) and an acid catalyst to perform a glycosylation reaction to deliver a glycosylation product (III); alternatively, mixing the glycosyl donor, the acceptor, and the trivalent iodine reagent, adding the transition metal catalyst to perform an activation reaction, and then adding the acid catalyst to perform the glycosylation reaction to obtain the glycosylation product (III). The detailed experimental process may be referred to the following examples.

EXAMPLES 1-54

In Examples 1-22 and 24-51: the glycosyl donor compound I (1.2 equivalents) and the trivalent iodine reagent are mixed in a reaction solvent of dichloromethane, and a transition metal catalyst is added at the temperature shown in Table 1 to react until the compound I disappears or no longer decreases, then, the acceptor compound II (1.0 equivalent) was added in sequence to react with the acid catalyst. After the reaction was completed as monitored by TLC, a saturated NaHCO$_3$ solution was added to terminate the reaction, and the reaction solution was extracted with dichloromethane. The extract is concentrated and then separated and purified by silica gel column chromatography to obtain the glycosylation product.

In Examples 23, 52-54: the glycosyl donor (I) and the acceptor (II) and the trivalent iodine reagent are mixed in a reaction solvent of dichloromethane, a transition metal catalyst is added at a temperature shown in Table 1 until the reaction is complete, and then an acid catalyst is added to react. After the reaction was completed as monitored by TLC, a saturated NaHCO$_3$ solution was added to terminate the reaction, and the reaction solution was extracted with dichloromethane. The extract is concentrated and then separated and purified by silica gel column chromatography to obtain the glycosylation product.

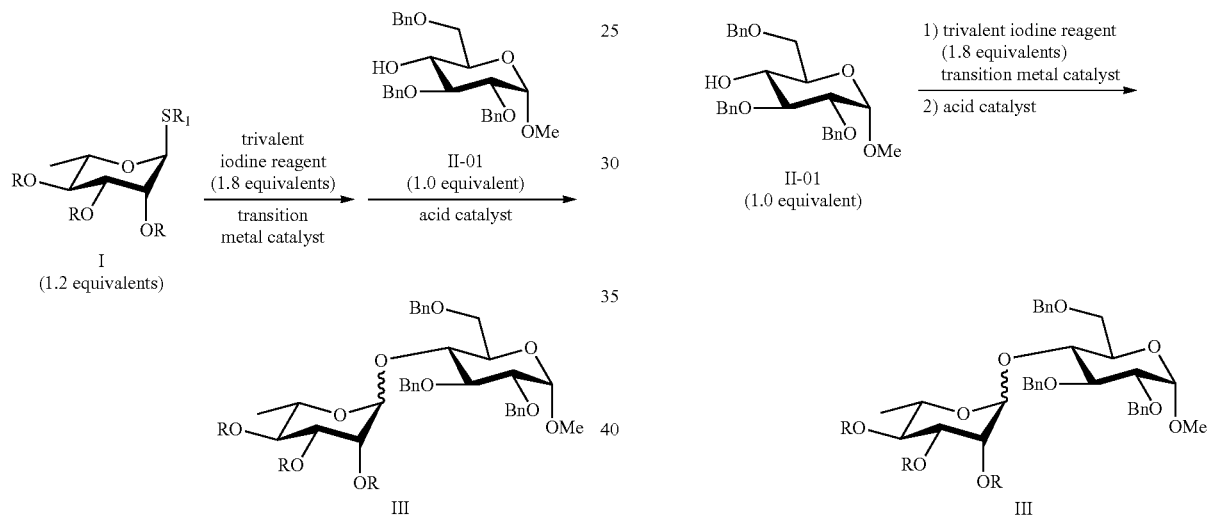

TABLE 1

| Example | I | IV | Transition Metal Catalyst (x mol %) | Acid (y eq.) | Solvent | Temperature | Product | Yield |
|---|---|---|---|---|---|---|---|---|
| 1 | I-02 | IV-1 | CuBr (0.5) | TfOH (0.2) | CH$_2$Cl$_2$ | 0° C. | III-01 | 95% |
| 2 | I-03 | IV-1 | CuBr (0.5) | TfOH (0.2) | CH$_2$Cl$_2$ | 0° C. | III-01 | 89% |
| 3 | I-04 | IV-1 | CuBr (0.5) | TfOH (0.2) | CH$_2$Cl$_2$ | 0° C. | III-01 | 92% |
| 4 | I-05 | IV-1 | CuBr (0.5) | TfOH (0.2) | CH$_2$Cl$_2$ | 0° C. | III-01 | 94%[a] |
| 5 | I-06 | IV-1 | CuBr (0.5) | TfOH (0.2) | CH$_2$Cl$_2$ | 0° C. | III-01 | 93% |
| 6 | I-07 | IV-1 | CuBr (0.5) | TfOH (0.2) | CH$_2$Cl$_2$ | 0° C. | III-01 | 48% |
| 7 | I-02 | IV-2 | CuBr (0.5) | TfOH (0.2) | CH$_2$Cl$_2$ | 0° C. | III-01 | 87% |
| 8 | I-02 | IV-3 | CuBr (0.5) | TfOH (0.2) | CH$_2$Cl$_2$ | 0° C. | III-01 | 94% |
| 9 | I-02 | IV-4 | CuBr (0.5) | TfOH (0.2) | CH$_2$Cl$_2$ | 0° C. | III-01 | 85% |
| 10 | I-02 | IV-5 | CuBr (0.5) | TfOH (0.2) | CH$_2$Cl$_2$ | 0° C. | III-01 | 58% |
| 11 | I-02 | IV-6 | CuBr (0.5) | TfOH (0.2) | CH$_2$Cl$_2$ | 0° C. | III-01 | 87% |
| 12 | I-02 | IV-7 | CuBr (0.5) | TfOH (0.2) | CH$_2$Cl$_2$ | 0° C. | III-01 | 84% |
| 13 | I-02 | IV-8 | CuBr (0.5) | TfOH (0.2) | CH$_2$Cl$_2$ | 0° C. | III-01 | 87% |
| 14 | I-02 | IV-1 | CuCl (0.5) | TfOH (0.2) | CH$_2$Cl$_2$ | 0° C. | III-01 | 98% |
| 15 | I-02 | IV-1 | CuI (0.5) | TfOH (0.2) | CH$_2$Cl$_2$ | 0° C. | III-01 | 95% |
| 16 | I-02 | IV-1 | CuOTf (0.5) | TfOH (0.2) | CH$_2$Cl$_2$ | 0° C. | III-01 | 90% |
| 17 | I-02 | IV-1 | Cu(MeCN)$_4$BF$_4$ (0.5) | TfOH (0.2) | CH$_2$Cl$_2$ | 0° C. | III-01 | 87% |

TABLE 1-continued

| Example I | IV | Transition Metal Catalyst (x mol %) | Acid (y eq.) | Solvent | Temperature | Product | Yield |
|---|---|---|---|---|---|---|---|
| 18 | I-02 | IV-1 | Ph$_2$PO$_2$Cu (0.5) | TfOH (0.2) | CH$_2$Cl$_2$ | 0° C. | III-01 | 95% |
| 19 | I-02 | IV-1 | CuTc (0.5) | TfOH (0.2) | CH$_2$Cl$_2$ | 0° C. | III-01 | 96% |
| 20 | I-02 | IV-1 | CuCl$_2$ (0.5) | TfOH (0.2) | CH$_2$Cl$_2$ | 0° C. | III-01 | 90% |
| 21 | I-02 | IV-1 | CuBr$_2$ (0.5) | TfOH (0.2) | CH$_2$Cl$_2$ | 0° C. | III-01 | 94% |
| 22 | I-02 | IV-1 | Cu(OTf)$_2$ (0.5) | TfOH (0.2) | CH$_2$Cl$_2$ | 0° C. | III-01 | 87% |
| 23 | I-02 | IV-1 | Cu(acac)$_2$ (0.5) | TfOH (0.2) | CH$_2$Cl$_2$ | 0° C. | III-01 | 93%[a] |
| 24 | I-02 | IV-1 | CuBr•SMe$_2$ (0.5) | TfOH (0.2) | CH$_2$Cl$_2$ | 0° C. | III-01 | 95% |
| 25 | I-02 | IV-1 | CuSO$_4$ (0.5) | TfOH (0.2) | CH$_2$Cl$_2$ | 0° C. | III-01 | 25% |
| 26 | I-02 | IV-1 | Cu(OAc)$_2$ (0.5) | TfOH (0.2) | CH$_2$Cl$_2$ | 0° C. | III-01 | 77% |
| 27 | I-02 | IV-1 | Cu(OTs)$_2$ (0.5) | TfOH (0.2) | CH$_2$Cl$_2$ | 0° C. | III-01 | 92% |
| 28 | I-02 | IV-1 | Cu(OTf)$_2$•Toluene (0.5) | TfOH (0.2) | CH$_2$Cl$_2$ | 0° C. | III-01 | 85% |
| 29 | I-02 | IV-1 | (iPr)CuCl (0.5) | TfOH (0.2) | CH$_2$Cl$_2$ | 0° C. | III-01 | 85% |
| 30 | I-02 | IV-1 | Rh$_2$(oct)$_4$ (0.5) | TfOH (0.2) | CH$_2$Cl$_2$ | 0° C. | III-01 | 89% |
| 31 | I-02 | IV-1 | Rh$_2$(OAc)$_4$ (0.5) | TfOH (0.2) | CH$_2$Cl$_2$ | 0° C. | III-01 | 87% |
| 32 | I-02 | IV-1 | CuBr (10) | TfOH (0.2) | CH$_2$Cl$_2$ | 0° C. | III-01 | 81% |
| 33 | I-02 | IV-1 | CuBr (0.1) | TfOH (0.2) | CH$_2$Cl$_2$ | 0° C. | III-01 | 53% |
| 34 | I-02 | IV-1 | CuBr (0.05) | TfOH (0.2) | CH$_2$Cl$_2$ | 0° C. | III-01 | 96% |
| 35 | I-02 | IV-1 | CuBr (0.025) | TfOH (0.2) | CH$_2$Cl$_2$ | 0° C. | III-01 | 82% |
| 36 | I-02 | IV-1 | CuBr (0.01) | TfOH (0.2) | CH$_2$Cl$_2$ | 0° C. | III-01 | 48% |
| 37 | I-02 | IV-1 | CuBr (0.5) | TfOH (0.1) | CH$_2$Cl$_2$ | 0° C. | III-01 | 41% |
| 38 | I-01 | IV-1 | CuBr (0.5) | Tf$_2$NH (0.2) | CH$_2$Cl$_2$ | 0° C. | III-02 | 92% |
| 39 | I-01 | IV-1 | CuBr (0.5) | TfOH•DTBMP (0.2) | CH$_2$Cl$_2$ | 0° C. | III-02 | 84% |
| 40 | I-01 | IV-1 | CuBr (0.5) | TfOH•DTBP (0.2) | CH$_2$Cl$_2$ | 0° C. | III-02 | 96% |
| 41 | I-01 | IV-1 | CuBr (0.5) | TfOH•Pyr. (0.2) | CH$_2$Cl$_2$ | 0° C. | III-02 | 15% |
| 42 | I-01 | IV-1 | CuBr (0.5) | TfOH•iPr$_2$NH (0.2) | CH$_2$Cl$_2$ | 0° C. | III-02 | 13% |
| 43 | I-01 | IV-1 | CuBr (0.5) | TMSOTf (0.2) | CH$_2$Cl$_2$ | 0° C. | III-02 | 89% |
| 44 | I-01 | IV-1 | CuBr (0.5) | Cu(OTf)$_2$ (0.2) | CH$_2$Cl$_2$ | Room temperature | III-02 | 90%[b] |
| 45 | I-01 | IV-1 | CuBr (0.5) | MsOH (0.2) | CH$_2$Cl$_2$ | 0° C. | III-02 | <5% |
| 46 | I-01 | IV-1 | CuBr (0.5) | TfOH•DTBP (0.2) | MeCN | 0° C. | III-02 | 96% |
| 47 | I-01 | IV-1 | CuBr (0.5) | TfOH•DTBP (0.2) | Toluene | 0° C. | III-02 | 53% |
| 48 | I-01 | IV-1 | CuBr (0.5) | TfOH•DTBP (0.2) | THF | 0° C. | III-02 | 17% |
| 49 | I-01 | IV-1 | CuBr (0.5) | TfOH•DTBP (0.2) | CHCl$_3$ | 0° C. | III-02 | 87% |
| 50 | I-01 | IV-1 | CuBr (0.5) | TfOH•DTBP (0.2) | DCE | 0° C. | III-02 | 84% |
| 51 | I-01 | IV-1 | CuBr (0.5) | TfOH•DTBP (0.2) | CH$_2$Cl$_2$ | 30° C. | III-02 | 75% |
| 52 | I-01 | IV-1 | CuBr (0.5) | TfOH•DTBP (0.2) | CH$_2$Cl$_2$ | −20° C. | III-02 | 96%[c] |
| 53 | I-01 | IV-1 | CuBr (0.5) | TfOH•DTBP (0.2) | CH$_2$Cl$_2$ | −40° C. | III-02 | 96%[c] |
| 54 | I-01 | IV-1 | CuBr (0.5) | TfOH•DTBP (0.2) | CH$_2$Cl$_2$ | −78° C. | III-02 | 74%[d] |

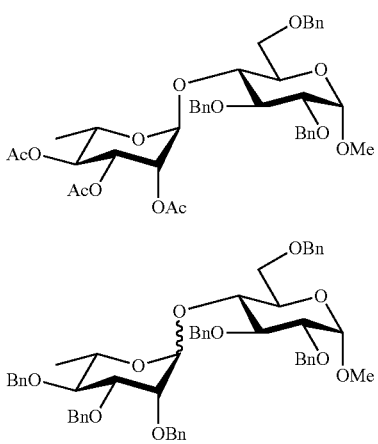

III-01: $^1$H NMR (600 MHz, CDCl$_3$) δ 7.42 (m, 2H), 7.35-7.25 (m, 13H), 5.48 (dd, J=1.8, 3.0 Hz, 1H), 5.30 (dd, J=3.6, 9.6 Hz, 1H), 5.14 (d, J=1.8 Hz, 1H, H-iF), 5.02 (t, J=9.6 Hz, 1H), 4.85 (d, J=12.0 Hz, 1H), 4.81 (d, J=11.4 Hz, 1H), 4.68 (d, J=11.4 Hz, 1H), 4.63 (d, J=11.6 Hz, 1H), 4.60 (d, J=3.6 Hz, 1H, H-i), 4.54 (s, 2H), 4.10 (d, J=1.8 Hz, 1H), 3.96 (dd, J=3.6, 10.2 Hz, 1H), 3.93 (mn, 2H), 3.88 (dd, J=2.4, 9.6 Hz, 1H), 3.62 (dd, J=6.6, 9.6 Hz, 1H), 3.58 (dd, J=6.6, 9.6 Hz, 1H), 3.36 (s, 3H), 2.04 (s, 3H), 2.02 (s, 3H), 1.98 (s, 3H), 1.12 (d, J=6.0 Hz, 3H).

III-02: $^1$H NMR (400 MHz, CDCl$_3$) δ 7.33-7.18 (30H, mn, Ar—CH), 5.00 (1H, s, H-i), 4.90 (1H, d, J=10.4 Hz, PhCH2), 4.86 (1H, d, J=11.2 Hz, PhCH2), 4.69 (2H, d, J=11.6 Hz, PhCH2), 4.56-4.51 (7H, mn, 6xPhCH2, H-i'), 4.44 (1H, d, J=12.0 Hz, PhCH2), 4.37 (1H, d, J 12.0 Hz, PhCH2), 3.91-3.84 (1H, m, H-5), 3.77-3.70 (3H, m), 3.66-3.39 (6H, m), 3.30 (3H, s, OCH3), 1.01 (3H, d, J=6.0 Hz, H-6).

It may be seen from the above examples that different donor structures, such as ethyl thioglycoside, isopropyl thioglycoside, benzyl thioglycoside, p-tolyl thioglycoside, phenyl thioglycoside, and o-ethyl phenyl thioglycoside all show good effects, preferably alkyl thioglycosides such as ethyl thioglycoside, isopropyl thioglycoside, and benzyl thioglycoside, and more preferably ethyl thioglycoside; good yields can obtain by using different trivalent iodine reagents, preferably IV-1 to IV-8, and more preferably IV-1.

Good yields can be obtained by using different transition metal catalysts, such as different copper salts and rhodium salts, preferred transition metal catalysts are cuprous chloride (CuCl), cuprous bromide (CuBr), cuprous iodide (CuI), cuprous bromide·dimethyl sulfide (CuBr·SMe$_2$), cuprous tetrafluoroborate tetraacetonitrile (Cu(MeCN)$_4$BF$_4$), cuprous trifluoromethanesulfonate (CuOTf), cuprous acetate (CuOAc), cuprous chloride [1,3-bis(2,6-diisopropylphenyl) imidazol-2-ylidene]((iPr)CuCl, cuprous diphenyl phosphate (Ph$_2$PO$_2$Cu), cuprous thiophene-2-carboxylate (CuTc), cupric chloride (CuCl$_2$), cupric bromide (CuBr$_2$), cupric acetate (Cu(OAc)$_2$), copper acetylacetonate (Cu(acac)$_2$), copper(II) hexafluoroacetylacetonate (Cu(hfacac)$_2$), copper (II) p-toluenesulfonate (Cu(OTs)$_2$), copper(II) trifluoromethanesulfonate (Cu(OTf)$_2$), cuprous trifluoromethanesulfonate toluene complex ((CuOTf)$_2$·Toluene), Rh$_2$(OAc)$_4$, Rh$_2$(oct)$_4$, in which in terms of molar percentage, the amount of the transition metal catalyst used is 0.01-10% of the glycosyl acceptor, such as 0.01-5%, such as 0.1-1%, 0.25-0.5%, and such as 0.5%.

Different acid catalysts, such as Brønsted acid, Brønsted salts, or Lewis acid, may play a catalytic role, for example, preferred acid catalysts are trifluoromethanesulfonic acid (TfOH), trifluoromethanesulfonic acid-2,5-di-tert-butylpyridinium salt (TfOH·DTBP), trifluoromethanesulfonic acid-2, 5-di-tert-butyl-4-methylpyridinium salt (TfOH·DTBMP), bistrifluoromethanesulfonimide (Tf$_2$NH), trimethylsilyl trifluoromethanesulfonate (TMSOTf), copper(II) trifluoromethanesulfonate Cu(OTf)$_2$), in which in terms of molar percentage, the amount of the acid catalyst used is 5-30% of the glycosyl acceptor, more preferably 10%-25%, such as 10-20%.

EXAMPLES 55-103

Unless otherwise specified, the standard operating procedure for the glycosylation reaction of Examples 55-103 is as follows: the glycosyl donor, the iodine ylide IV-1, and a dry molecular sieve 4A MS (160 mg/mL in CH$_2$Cl$_2$ solution) were placed in a Schlenk bottle, sealed with rubber stoppers, deoxygenated by argon replacement on double-row tubes; then, anhydrous CH$_2$Cl$_2$ (c=0.1 M, calculated based on 1.0 equivalent of reactants) was added in an argon atmosphere, the reaction system was precooled to 0° C., and a 0.02 M CuCl acetonitrile solution (0.5 mol %) was added, and the reaction was continued at 0° C. for about 5 min until the reaction was complete, then, the glycosyl acceptor and an acid catalyst (20 mol %) were added, and the mixture was reacted at 0° C. until the reaction was completed. A saturated NaHCO$_3$ solution was added to terminate the reaction. The concentrated product after extraction is separated and purified by silica gel column chromatography to obtain the glycosylation product. In some implementation examples, if the contents with special instructions are inconsistent with the standard operating procedure for the reaction, then the contents with special instructions shall prevail.

EXAMPLE 55: Preparation of a Compound III-03 by Glycosylation with the Trivalent Iodine Reagent

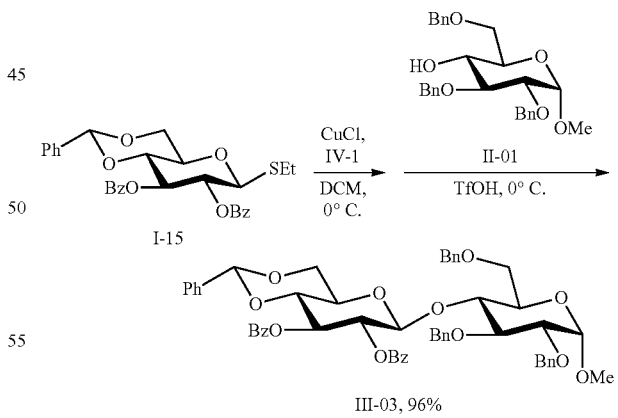

According to the standard operating procedure for the reaction, the donor I-15 (30.0 mg, 0.058 mmol, 1.2 equivalents), the trivalent iodine reagent IV-1 (24.1 mg, 0.072 mmol, 1.5 equivalents), and the molecular sieve were added to the reaction bottle. CuCl was added, and until I-15 was completely converted, the acceptor II-01 (22.3 mg, 0.048 mmol, 1.0 equivalent) and TfOH were added. After the reaction was completed, a white solid compound III-03

(42.5 mg, 96%) was obtained after treatment. $^1$H NMR (600 MHz, CDCl$_3$) δ 7.93 (d, J=7.8 Hz, 2H, Ar—H), 7.86 (d, J=7.8 Hz, 2H, Ar—H), 7.54-7.25 (m, 26H, Ar—H), 5.56 (t, J=9.6 Hz, 1H), 5.44 (s, 1H), 5.39 (t, J=8.4 Hz, 1H), 4.98 (d, J=10.8 Hz, 1H, PhCH$_2$), 4.86 (d, J=11.4 Hz, 1H, PhCH$_2$), 4.78 (d, J=12.6 Hz, 1H, PhCH$_2$), 4.73 (d, J=7.8 Hz, 1H), 4.70 (d, J=12.0 Hz, 1H, PhCH$_2$), 4.63 (d, J=12.0 Hz, 1H, PhCH$_2$), 4.55 (d, J=3.6 Hz, 1H), 4.31 (d, J=12.0 Hz, 1H, PhCH$_2$), 4.22 (dd, J=5.4, 10.8 Hz, 1H), 3.95 (t, J=9.0 Hz, 1H), 3.85 (t, J=9.0 Hz, 1H), 3.78 (t, J=9.6 Hz, 1H), 3.64 (dd, J=3.0, 10.8 Hz, 1H), 3.54-3.49 (m, 2H), 3.46 (m, 1H), 3.39-3.35 (m, 2H), 3.28 (s, 3H), $^{13}$C NMR (150 MHz, CDCl$_3$) δ 165.63, 165.07, 139.54, 138.44, 137.82, 136.99, 133.42, 133.16, 129.87, 129.57, 129.23, 129.16, 128.96, 128.66, 128.55, 128.49, 128.41, 128.33, 128.30, 128.17, 127.92, 127.61, 127.44, 126.27, 101.50, 100.90, 98.50, 80.03, 78.98, 75.49, 73.76, 73.65, 73.03, 72.34, 69.64, 68.72, 67.53, 66.44, 55.48. HRMS (ESI+): calc. for C$_{55}$H$_{54}$NaO$_{13}$ [M+Na]$^+$ 945.3457, found: 945.3445.

EXAMPLE 56: Preparation of a Compound III-04 by Glycosylation with the Trivalent Iodine Reagent

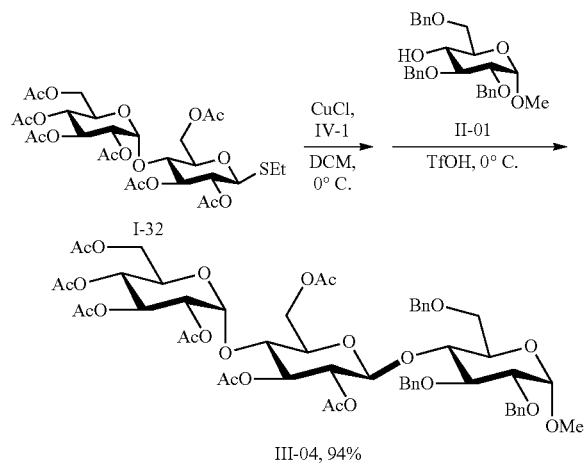

According to the standard operating procedure for the reaction, the donor I-32 (35.2 mg, 0.052 mmol, 1.2 equivalents), the trivalent iodine reagent IV-1 (21.6 mg, 0.065 mmol, 1.5 equivalents), and the molecular sieve were added to the reaction bottle. CuCl was added, and until I-32 was completely converted, the acceptor II-01 (20.0 mg, 0.043 mmol, 1.0 equivalent) and TfOH were added. After the reaction was completed, a compound III-04 (43.8 mg, 94%) was obtained as a colorless syrup after treatment.

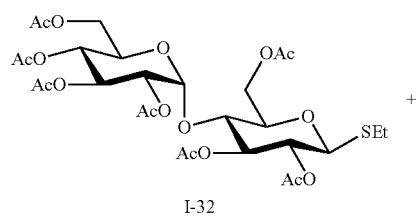

According to the standard operating procedure for the reaction, the donor I-32 (35.2 mg, 0.052 mmol, 1.2 equivalents), the acceptor II-01 (20.0 mg, 0.043 mmol, 1.0 equivalent), the trivalent iodine reagent IV-1 (21.6 mg, 0.065 mmol, 1.5 equivalents), and the molecular sieve were added to the reaction bottle. CuCl was added, and until I-32 was completely converted, TfOH was added. After the reaction was completed, the compound III-04 (41.0 mg, 88%) was obtained as a colorless syrup after treatment. $^1$H NMR (400 MHz, CDCl$_3$) δ 7.49-7.26 (m, 15H, Ar—H), 5.42-5.36 (m, 1H), 5.33 (d, J=3.9 Hz, 1H), 5.07 (t, J=8.5 Hz, 1H), 5.02 (t, J=7.6 Hz, 1H), 4.96 (d, J=11.6 Hz, 1H), 4.87 (dd, J=10.6, 3.6 Hz, 1H), 4.79 (d, J=12.0 Hz, 1H), 4.72 (dd, J=15.3, 5.7 Hz, 3H), 4.57 (dd, J=8.0, 4.3 Hz, 2H), 4.46 (d, J=8.1 Hz, 1H), 4.42 (d, J=12.0 Hz, 1H), 4.22 (dd, J=12.5, 3.5 Hz, 1H), 4.14 (dd, J=12.0, 2.8 Hz, 1H), 4.07 (dd, J=12.1, 3.9 Hz, 1H), 3.99 (dd, J=12.5, 2.1 Hz, 1H), 3.91-3.83 (m, 3H), 3.83-3.77 (m, 2H), 3.61 (t, J=9.4 Hz, 2H), 3.47 (dd, J=9.2, 3.7 Hz, 1H), 3.37 (s, 3H), 3.15 (dt, J=9.7, 3.3 Hz, 1H), 2.11 (s, 3H), 2.08 (s, 3H), 2.05 (d, J=2.5 Hz, 3H), 2.02 (s, 3H), 1.98 (s, 3H), 1.97-1.92 (m, 6H).

EXAMPLE 57: Preparation of a Compound III-05 by Glycosylation with the Trivalent Iodine Reagent

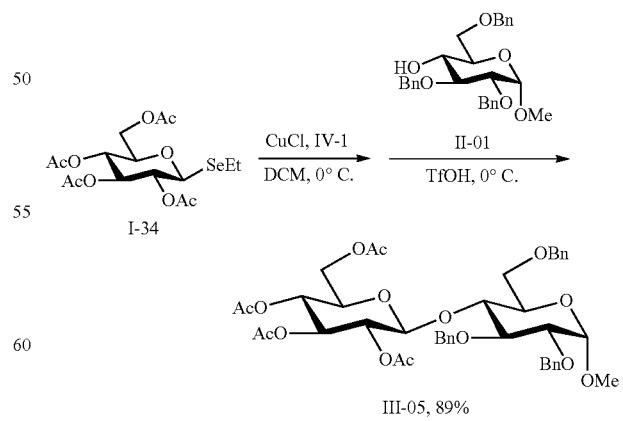

According to the standard operating procedure for the reaction, the donor I-34 (22.8 mg, 0.052 mmol, 1.2 equivalents), the trivalent iodine reagent IV-1 (21.6 mg, 0.065 mmol, 1.5 equivalents), and the molecular sieve were added to the reaction bottle. CuCl was added, and until I-34 was completely converted, the acceptor II-01 (20.0 mg, 0.043 mmol, 1.0 equivalent) and TfOH were added. After the reaction was completed, a compound III-05 (30.4 mg, 89%) was obtained as a colorless syrup after treatment.

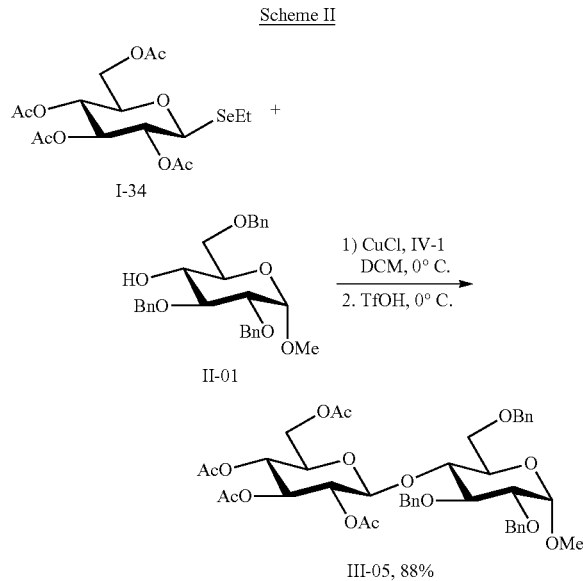

According to the standard operating procedure, the donor I-34 (22.8 mg, 0.052 mmol, 1.2 equivalents), the acceptor II-01 (20.0 mg, 0.043 mmol, 1.0 equivalent), the trivalent iodine reagent IV-1 (21.6 mg, 0.065 mmol, 1.5 equivalents), and the molecular sieve were added to the reaction bottle. CuCl was added, and until I-34 was completely converted, TfOH was added. After the reaction was completed, the compound III-05 (30.1 mg, 88%) was obtained as a colorless syrup after treatment. $^1$H NMR (400 MHz, CDCl$_3$) δ 7.40-7.20 (15H, m, Ar—H), 5.00 (1H, t, J=9.2 Hz), 4.97-4.91 (2H, m), 4.87 (1H, t, J=9.2 Hz), 4.75-4.70 (3H, m, PhCH$_2$), 4.57 (1H, d, J=11.6 Hz, PhCH$_2$), 4.55 (1H, d, J=3.2 Hz, H-1), 4.47 (1H, d, J=8.0 Hz, H-l'), 4.40 (1H, d, J=12.0 Hz, PhCH$_2$) 4.12 (1H, dd, J=12.0, 4.0 Hz, H-6a), 3.88-3.79 (3H, m), 3.74 (1H, dd, J=10.8, 2.8 Hz), 3.60-3.56 (2H, m), 3.45 (1H, dd, J=8.4, 4.4 Hz) 3.34 (3H, s, —OCH$_3$), 3.30-3.26 (1H, m), 1.98 (3H, s, —COCH$_3$), 1.96 (3H, s, —COCH$_3$), 1.93 (3H, s, —COCH$_3$), 1.92 (3H, s, —COCH$_3$).

EXAMPLE 58: Preparation of a Compound III-06 by Glycosylation with the Trivalent Iodine Reagent

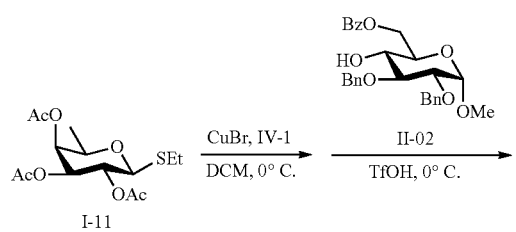

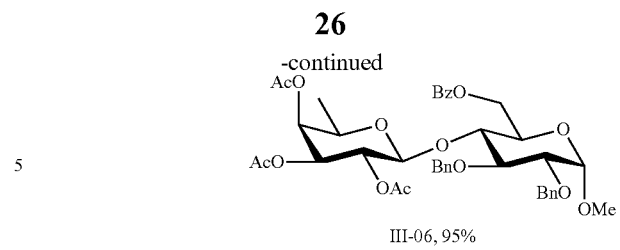

According to the standard operating procedure for the reaction, the donor I-11 (16.7 mg, 0.052 mmol, 1.2 equivalents), the trivalent iodine reagent IV-1 (21.0 mg, 0.065 mmol, 1.5 equivalents), and the molecular sieve were added to the reaction bottle. CuBr was added, and until I-I1 was completely converted, the acceptor II-02 (20.0 mg, 0.042 mmol, 1.0 equivalent) and TfOH were added. After the reaction was completed, a compound III-06 (29.8 mg, 95%) was obtained as a colorless syrup after treatment. $^1$H NMR (600 MHz, CDCl$_3$) δ 8.00 (2H, dd, J=1.2, 7.8 Hz, Ar—H), 7.58 (1H, m, Ar—H), 7.45 (2H, t, J=7.8 Hz, Ar—H), 7.41 (2H, d, J=7.2 Hz, Ar—H), 7.35-7.27 (8H, m, Ar—CH), 5.18 (1H, dd, J=8.4, 10.2 Hz, H-2'), 5.11 (1H, d, J=3.0 Hz, H-4), 5.00 (1H, d, J=10.8 Hz, PhCH$_2$), 4.98 (1H, d, J=11.4 Hz, PhCH$_2$), 4.90 (1H, dd, J=3.6, 10.8 Hz, H-3), 4.76 (1H, d, J=8.4 Hz, H-i'), 4.75 (1H, d, J=12.0 Hz, PhCH$_2$), 4.63 (1H, dd, J=1.8, 11.4 Hz, H-6a'), 4.61 (1H, d, J=12.0 Hz, PhCH$_2$), 4.57 (1H, d, J=3.6 Hz, H-1), 4.36 (1H, dd, J=5.4, 11.4 Hz, H-6b), 4.00 (1H, t, J=9.0 Hz, H-4), 3.94 (1H, m, H-5'), 3.85 (1H, dd, J=8.4, 9.6 Hz, H-3), 3.54 (1H, dd, J=3.6, 9.6 Hz, H-2), 3.48 (1H, m, H-5), 3.38 (3H, s, OCH$_3$), 2.14 (3H, s, COCH$_3$), 2.04 (3H, s, COCH$_3$), 1.95 (3H, s, COCH$_3$), 0.99 (3H, d, J=6.6 Hz, H-6').

EXAMPLE 59: Preparation of a Compound III-07 by Glycosylation with the Trivalent Iodine Reagent

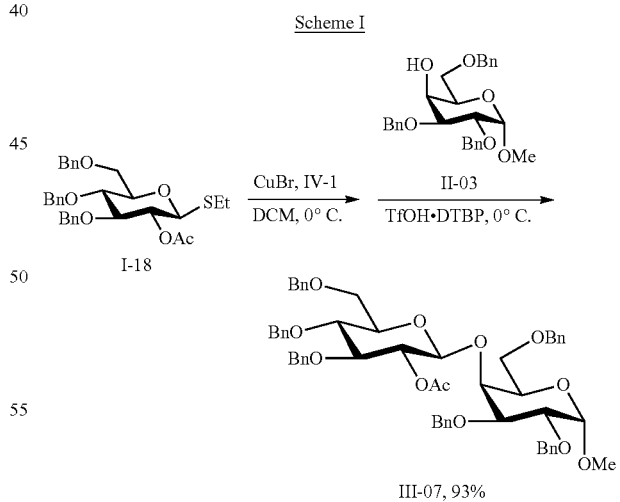

According to the standard operating procedure for the reaction, the donor I-18 (27.9 mg, 0.052 mmol, 1.2 equivalents), the trivalent iodine reagent IV-1 (21.6 mg, 0.065 mmol, 1.5 equivalents), and the molecular sieve were added to the reaction bottle. CuBr was added, and until I-18 was completely converted, the acceptor II-03 (20 mg, 0.043 mmol, 1.0 equivalent) and TfOH·DTBP were added. After the reaction was completed, a compound III-07 (43.4 mg, 93%) was obtained as a colorless syrup after treatment.

Scheme II

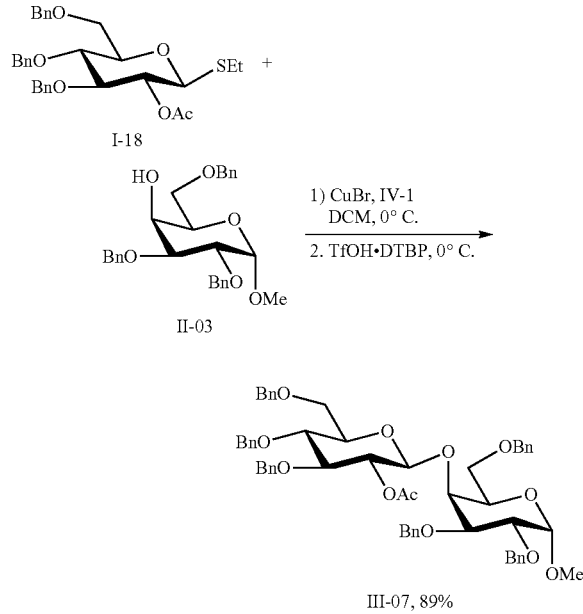

According to the standard operating procedure for the reaction, the donor I-18 (27.9 mg, 0.052 mmol, 1.2 equivalents), the acceptor II-03 (20 mg, 0.043 equivalents), the trivalent iodine reagent IV-1 (21.6 mg, 0.065 mmol, 1.5 equivalents), and the molecular sieve were added to the reaction bottle. CuBr was added, and until I-18 was completely converted, TfOH·DTBP was added. After the reaction was completed, the compound III-07 (35.9 mg, 89%) was obtained as a colorless syrup after treatment. $^1$H NMR (600 MHz, CDCl$_3$) δ 7.36-7.24 (28H, m, Ar—H), 7.18 (m, 2H, Ar—H), 4.99 (1H, t, J=8.4 Hz), 4.80 (1H, d, J=12.0 Hz), 4.77 (2H, d, J=11.4 Hz), 4.74 (1H, d, J=12.0 Hz), 4.67 (2H, d, J=12.0 Hz), 4.64 (1H, d, J=3.6 Hz, H-1), 4.58 (1H, d, J=11.4 Hz), 4.55 (1H, d, J=10.8 Hz, H-1'), 4.50 (1H, d, J=12.0 Hz), 4.47 (2H, d, J=12.0 Hz), 4.41 (1H, d, J=12.0 Hz), 4.03 (1H, d, J=2.4 Hz), 3.88 (1H, m), 3.84 (1H, dd, J=2.4, 9.6 Hz), 3.80-3.78 (2H, m), 3.70-3.61 (5H, m), 3.39-3.37 (1H, m), 3.35 (s, 3H, OCH$_3$), 1.74 (3H, s, COCH$_3$).

EXAMPLE 60: Preparation of a Compound III-08 by Glycosylation with the Trivalent Iodine Reagent

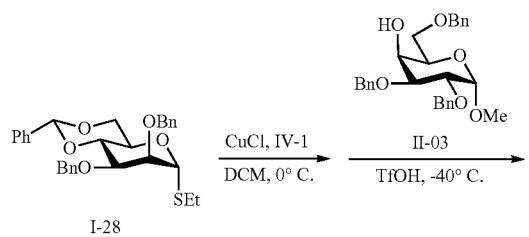

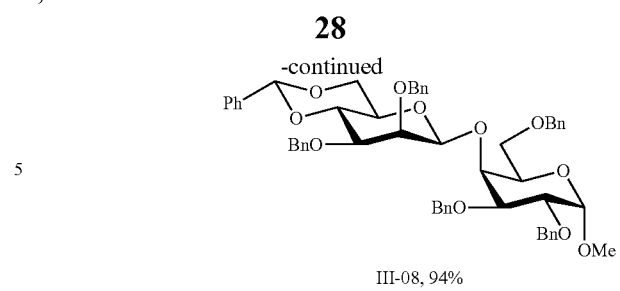

According to the standard operating procedure for the reaction, the donor I-28 (25.6 mg, 0.052 mmol, 1.2 equivalents), the trivalent iodine reagent IV-1 (21.6 mg, 0.065 mmol, 1.5 equivalents), and the molecular sieve were added to the reaction bottle. CuCl was added, and until I-28 was completely converted, the acceptor II-03 (20 mg, 0.043 mmol, 1.0 equivalent) and TfOH were added. After the reaction was completed, a compound III-08 (36.2 mg, 94%) was obtained as a colorless syrup after treatment. $^1$H NMR (400 MHz, CDCl$_3$) δ 7.43-7.16 (m, 30H, Ar—H), 5.50 (s, 1H), 4.78 (d, J=12.4 Hz, 1H, Ph CH$_2$), 4.78 (d, J=11.6 Hz, 1H, PhCH$_2$), 4.70 (d, J=3.6 Hz, 1H, H-1), 4.69-4.63 (m, 3H, H-i', PhCH$_2$), 4.59-4.51 (m, 3H, PhCH$_2$), 4.49 (d, J=12.0 Hz, 1H, PhCH$_2$), 4.47-4.41 (m, 2H, PhCH$_2$), 4.12-4.02 (m, 3H), 3.91-3.82 (m, 3H), 3.79-3.73 (m, 2H), 3.69 (dd, J=10.0, 5.6 Hz, 1H), 3.61 (dd, J=10.0, 6.4 Hz, 1H), 3.35 (s, 3H), 3.32 (dd, J=10.0, 3.0 Hz, 1H), 3.09 (td, J=10.0, 4.8 Hz, 1H). $^{13}$C NMR (100 MHz, CDCl$_3$) δ 139.0, 138.6, 138.6, 138.5, 138.4, 137.7, 129.0, 128.7, 128.5, 128.5, 128.4, 128.4, 128.3, 128.2, 128.1, 128.0, 127.9, 127.7, 127.7, 127.6, 127.5, 127.5, 126.2, 102.8, 101.4, 98.5, 78.6, 78.6, 78.4, 76.5, 75.4, 75.0, 73.8, 73.4, 73.4, 72.3, 69.8, 69.3, 68.7, 67.7, 55.5. HRMS (ESI+): calc. for C$_{55}$H$_{58}$NaO$_{11}$ [M+Na]$^+$ 917.3871, found: 917.3884.

EXAMPLE 61: Preparation of a Compound III-09 by Glycosylation with the Trivalent Iodine Reagent According to the standard operating procedure for the reaction, the donor I-36 (16.7 mg, 0.052 mmol, 1.2 equivalents), the trivalent iodine reagent IV-1 (21.6 mg, 0.065 mmol, 1.5 equivalents), and the molecular sieve were added to the reaction bottle. CuBr was added, and until I-36 was completely converted, the acceptor II-03 (20 mg, 0.043 mmol, 1.0 equivalent) and TfOH were added. After the reaction was completed, a compound III-09 (28.9 mg, 93%) was obtained as a colorless syrup after treatment. $^1$H NMR (600 MHz, CDCl$_3$) δ 7.38 (d, J=7.2 Hz, 2H, Ar—H), 7.32 (dd, J=4.8, 12.6 Hz, I0H, Ar—H), 7.28 (m, 1H, Ar—H), 7.27 (m, 2H, Ar—H), 5.38 (d, 2H, H-i', H-2'), 5.29 (dd, J=4.2, 7.2 Hz, 1H, H-3'), 4.81 (d, J=11.4 Hz, 2H, PhCH$_2$), 4.66 (d, J=11.4 Hz, 1H, PhCH$_2$), 4.65 (d, J=12.0 Hz, 1H, PhCH$_2$), 4.60 (d, J=2.4 Hz, 1H, H-1), 4.55 (d, J=11.4 Hz, 1H, PhCH$_2$), 4.51 (d, J=11.4 Hz, 1H, PhCH$_2$), 4.29 (dd, J=3.6, 11.6 Hz, 1H, H-5a'), 4.21 (m, 1H, H-4'), 4.13 (s, 1H, H-4), 4.09 (dd, J=6.6, 12.0 Hz, 1H, H-5b'), 3.90 (m, 1H, H-5), 3.87 (d, J=1.8 Hz, 2H), 3.68 (dd, J=9.6, 6.6 Hz, 1H, H-6a), 3.55 (dd, J=6.0, 9.0 Hz, 1H, H-6b), 3.36 (s, 3H, OMe), 2.04 (s, 3H), 2.00 (s, 3H), 1.91 (s, 3H). $^{13}$C NMR (100 MHz, CDCl$_3$) δ 170.56, 169.55, 169.26, 138.51, 138.29, 138.19, 128.43, 128.38, 128.27, 127.80, 127.77, 127.64, 127.50, 127.46, 107.15, 98.72, 78.09, 78.01, 76.16, 75.77, 74.91, 73.71, 73.43, 73.40, 71.13, 69.20, 68.65, 64.63, 55.37, 20.74, 20.54, 20.42. HRMS (ESI+): calc. for C$_{39}$H$_{46}$NaO$_{13}$ [M+Na]$^+$745.2831, found: 745.2823.

EXAMPLE 62: Preparation of a Compound III-10 by Glycosylation with the Trivalent Iodine Reagent

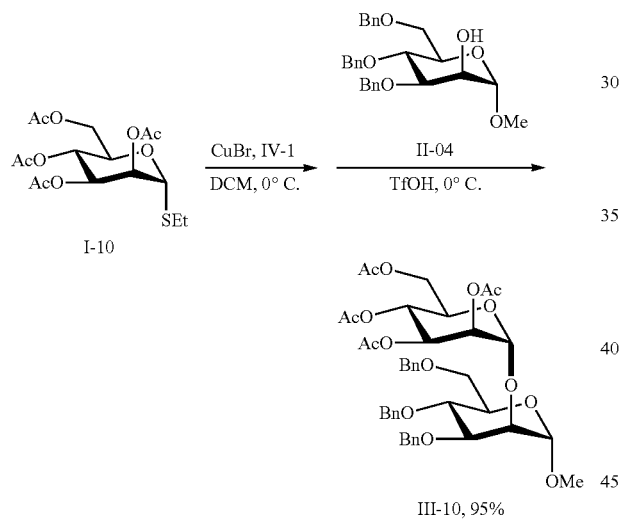

According to the standard operating procedure for the reaction, the donor I-10 (20.3 mg, 0.052 mmol, 1.2 equivalents), the trivalent iodine reagent IV-1 (21.6 mg, 0.065 mmol, 1.5 equivalents), and the molecular sieve were added to the reaction bottle. CuBr was added, and until I-10 was completely converted, the acceptor II-04 (20.0 mg, 0.043 mmol, 1.0 equivalent) and TfOH were added. After the reaction was completed, a compound III-10 (32.5 mg, 95%) was obtained as a colorless syrup after treatment.

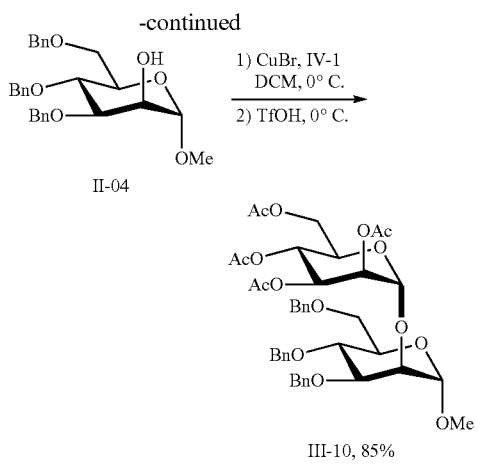

According to the standard operating procedure for the reaction, the donor I-10 (20.3 mg, 0.052 mmol, 1.2 equivalents), the acceptor II-04 (20.0 mg, 0.043 mmol, 1.0 equivalents), the trivalent iodine reagent IV-1 (21.6 mg, 0.065 mmol, 1.5 equivalents), and the molecular sieve were added to the reaction bottle. CuBr was added, and until I-10 was completely converted, TfOH was added. After the reaction was completed, the compound III-10 (29.1 mg, 85%) was obtained as a colorless syrup after treatment. $^1$H NMR (400 MHz, CDCl$_3$) δ 7.36-7.23 (13H, d, J=7.6 Hz, Ar—CH), 7.15-7.13 (2H, m, Ar—CH), 5.43 (1H, dd, J=2.0, 3.2 Hz, H-2), 5.39 (1H, dd, J =3.6, 10.0 Hz, H-3), 5.23 (1H, t, J=9.6 Hz, H-4), 4.95 (1H, s, H-1), 4.81 (1H, d, J=10.8 Hz, PhCH$_2$), 4.77 (1H, d, J=2.0 Hz, H-i'), 4.69 (1H, d, J=12.0 Hz, PhCH$_2$), 4.63-4.54 (3H, m, PhCH$_2$), 4.48 (1H, d, J=10.8 Hz, PhCH$_2$), 4.22 (1H, dd, J=5.2, 11.6 Hz, H-6a), 4.20-4.15 (1H, m, H-5), 4.09 (1H, dd, J=2.0, 11.6 Hz, H-6b), 3.92 (1H, br s, H-2'), 3.90-3.82 (2H, m, H-6a', H-4'), 3.75-3.70 (3H, m, H-3', H-5', H-6b'), 3.33 (3H, s, OCH$_3$), 2.09 (3H, s, COCH$_3$), 2.07 (3H, s, COCH$_3$), 1.98 (3H, s, COCH$_3$), 1.97 (3H, s, COCH$_3$).

EXAMPLE 63: Preparation of a compound III-11 by glycosylation with the trivalent iodine reagent

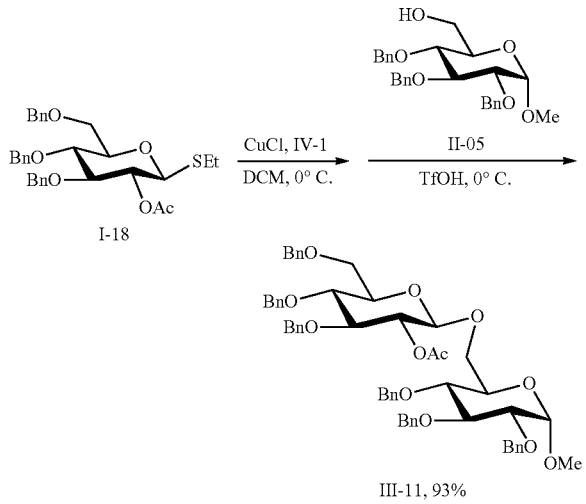

According to the standard operating procedure for the reaction, the donor I-18 (27.7 mg, 0.052 mmol, 1.2 equivalents), the trivalent iodine reagent IV-1 (21.6 mg, 0.065 mmol, 1.5 equivalents), and the molecular sieve were added to the reaction bottle. CuCl was added, and until I-18 was completely converted, the acceptor II-05 (20.0 mg, 0.043 mmol, 1.0 equivalent) and TfOH were added. After the reaction was completed, a compound III-11 (37.6 mg, 93%) was obtained as a colorless syrup after treatment. $^1$H NMR (400 MHz, CDCl$_3$) δ 7.37-7.25 (m, 30H), 5.03 (t, J=8.8 Hz, 1H), 4.95 (d, J=11.2 Hz, 1H), 4.83-4.73 (m, 5H), 4.63 (d, J=11.6 Hz, 1H), 4.62 (d, J=12.0 Hz, 1H) 4.58-4.48 (m, 5H), 4.37 (d, J=8.0 Hz, 1H, H-1), 4.07 (dd, J=10.8, 1.6 Hz, 1H), 3.95 (t, J=9.2 Hz, 1H), 3.76-3.69 (m, 2H), 3.68-3.59 (m, 4H), 3.50 (dd, J=9.6, 3.6 Hz, 1H), 3.48-3.40 (m, 2H), 3.33 (s, 3H), 1.85 (s, 3H).

EXAMPLE 64: Preparation of a Compound III-12 by Glycosylation with the Trivalent Iodine Reagent

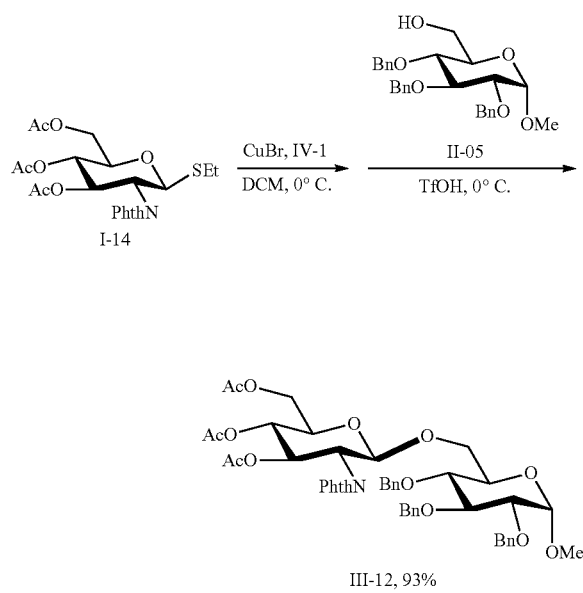

III-12, 93%

According to the standard operating procedure for the reaction, the donor I-14 (24.8 mg, 0.052 mmol, 1.2 equivalents), the trivalent iodine reagent IV-1 (28.8 mg, 0.086 mmol, 2.0 equivalents), and the molecular sieves were added to the reaction bottle. CuBr was added, and until I-14 was completely converted, the acceptor II-05 (20 mg, 0.043 mmol, 1.0 equivalent) and TfOH were added. After the reaction was completed, a white solid compound III-12 (35.3 mg, 93%) was obtained after treatment. $^1$H NMR (400 MHz, CDCl$_3$) δ 7.53 (4H, br s, Ar—H), 7.30-7.19 (13H, m, Ar—H), 7.01-6.98 (2H, m, Ar—H), 5.77 (1H, dd, J=8.8, 10.4 Hz, H-2), 5.39 (1H, d, J=8.8 Hz, H-1), 5.13 (1H, t, J=10.0, 10.2 Hz, H-3), 4.80 (1H, d, J=10.8 Hz, PhCH$_2$), 4.66 (1H, d, J=12.0 Hz, PhCH$_2$), 4.60 (1H, d, J=10.8 Hz, PhCH$_2$), 4.52 (1H, d, J=12.0 Hz, PhCH$_2$), 4.38-4.32 (3H, m), 4.30 (1H, dd, J=4.4, 12.0 Hz), 4.12 (1H, dd, J=2.4, 12.4 Hz), 4.08-4.03 (2H, m), 3.84-3.83 (1H, m), 3.82 (1H, dd, J=9.6 Hz), 3.61 (2H, dd, J=4.0, 12.8 Hz), 3.33 (1H, dd, J=3.6, 9.6 Hz), 3.20 (1H, t, J=9.2 Hz), 3.12 (3H, s, OCH$_3$), 2.04 (3H, s, COCH$_3$), 1.98 (3H, s, COCH$_3$), 1.80 (3H, s, COCH$_3$).

EXAMPLE 65: Preparation of a Compound III-13 by Glycosylation with the Trivalent Iodine Reagent

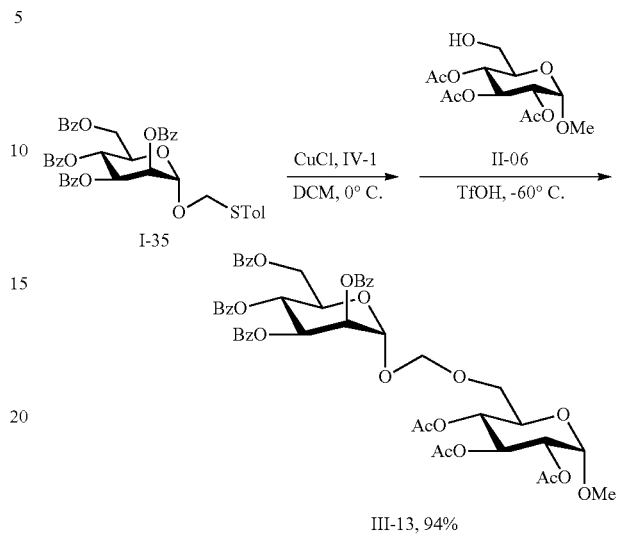

III-13, 94%

According to the standard operating procedure for the reaction, the donor I-35 (24.7 mg, 0.034 mmol, 1.2 equivalents), the trivalent iodine reagent IV-1 (14.1 mg, 0.042 mol, 1.5 equivalents), and the molecular sieve were added to the reaction bottle. CuCl was added, and until I-35 was completely converted, the acceptor II-06 (9.0 mg, 0.028 mmol, 1.0 equivalent) and TfOH were added. After the reaction was completed, a compound III-13 (24.4 mg, 94%) was obtained as a colorless syrup after treatment. $^1$H NMR (600 MHz, CDCl$_3$) δ 8.10-8.08 (m, 2H, Ar—H), 8.05-8.03 (m, 2H, Ar—H), 7.95-7.92 (m, 2H, Ar—H), 7.84-7.81 (m, 2H, Ar—H), 7.61-7.56 (m, 2H, Ar—H), 7.52-7.47 (m, 1H, Ar—H), 7.45-7.34 (m, 7H, Ar—H), 7.29-7.25 (m, 2H, Ar—H), 6.09 (t, J=10.2 Hz, 1H, H-4'), 5.90 (dd, J=10.2, 3.6 Hz, 1H, H-3'), 5.70 (dd, J=3.0, 1.8 Hz, 1H, H-2'), 5.48 (dd, J=10.2, 9.6 Hz, 1H, H-3), 5.42 (d, J=1.8 Hz, 1H, H-i'), 5.15 (t, J=9.6 Hz, 1H, H-4), 5.10 (d, J=6.8 Hz, 1H, CH$_2$), 4.95 (d, J=3.6 Hz, 1H, H-1), 4.88 (dd, J=10.2, 3.6 Hz, 1H, H-2), 4.83 (d, J=6.6 Hz, 1H, CH$_2$), 4.71-4.67 (m, 1H, H-6'a), 4.50-4.43 (m, 2H, H-5', H-6'b), 3.96-3.90 (m, 1H, H-5), 3.85 (dd, J=11.4, 4.2 Hz, 1H, H-6a), 3.71 (dd, J=11.4, 2.4 Hz, 1H, H-6b), 3.40 (s, 3H, —OCH$_3$), 2.06 (s, 3H, —COCH$_3$), 2.00 (s, 3H, —COCH$_3$), 1.97 (s, 3H, —COCH$_3$).

EXAMPLE 66: Preparation of a Compound III-14 by Glycosylation with the Trivalent Iodine Reagent Scheme I

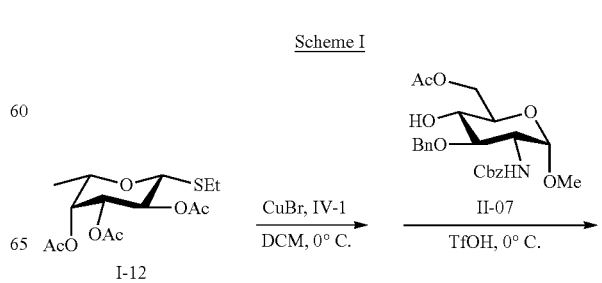

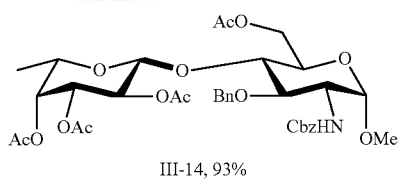

III-14, 93%

According to the standard operating procedure for the reaction, the donor I-12 (17.4 mg, 0.052 mmol, 1.2 equivalents), the trivalent iodine reagent IV-1 (21.6 mg, 0.065 mmol, 1.5 equivalents), and the molecular sieve were added to the reaction bottle. CuBr was added, and until I-12 was completely converted, the acceptor II-07 (20 mg, 0.043 mmol, 1.0 equivalent) and TfOH were added. After the reaction was completed, a compound III-14 (29.6 mg, 93%) was obtained as a colorless syrup after treatment.

Scheme II

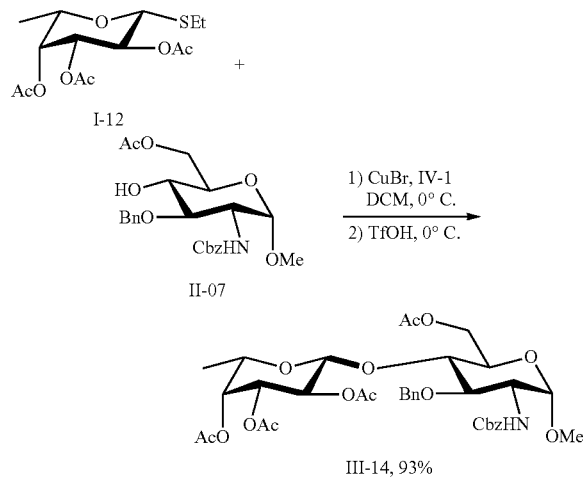

III-14, 93%

According to the standard operating procedure, the donor I-12 (17.4 mg, 0.052 mmol, 1.2 equivalent), the acceptor II-07 (20 mg, 0.043 mmol, 1.0 equivalent), the trivalent iodine reagent IV-1 (21.6 mg, 0.065 mmol, 1.5 equivalents), and the molecular sieve were added to the reaction bottle. CuBr was added, and until I-12 was completely converted, TfOH was added.

After the reaction was completed, a compound III-14 (29.6 mg, 93%) was obtained as a colorless syrup after treatment. $^1$H NMR (400 MHz, CDCl$_3$) δ 7.31-7.28 (10H, m, Ar—H), 5.14-5.04 (4H, m), 4.93-4.87 (3H, m), 4.68 (1H, d, J=10.0 Hz), 4.63 (1H, d, J=3.2 Hz, H-1), 4.57 (1H, d, J=10.0 Hz), 4.33 (1H, dd, J=2.0, 12.0 Hz, H-6a'), 4.27 (1H, dd, J=4.8, 12.0 Hz, H-6b'), 3.96 (1H, m, H-5'), 3.88 (1H, t, J=9.6, 9.2 Hz,), 3.74 (1H, m, H-5), 3.61 (2H, m), 3.33 (3H, s, CH3), 2.16 (3H, s, CH$_3$), 2.05 (3H, s, CH$_3$), 2.04 (3H, d, CH$_3$), 1.96 (3H, s, CH$_3$), 1.09 (3H, d, J=6.4 Hz, CH$_3$). $^{13}$C NMR (100 MHz, CDCl$_3$) δ 170.96, 170.89, 170.34, 169.59, 156.02, 137.65, 136.38, 128.85, 128.76, 128.49, 128.33, 100.16, 99.03, 81.39, 75.80, 74.15, 69.79, 69.18, 68.67, 67.29, 63.26, 55.33, 54.89, 29.89, 21.23, 21.18, 20.90, 20.83, 15.99. HRMS (ESI+): calc. for C$_{36}$H$_{45}$NNaO$_{15}$ [M+Na]$^+$754.2681, found: 754.2677.

EXAMPLE 67: Preparation of a Compound III-15 by Glycosylation with the Trivalent Iodine Reagent

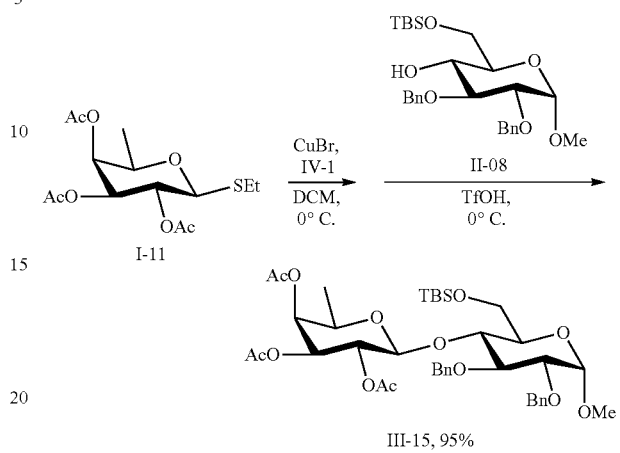

III-15, 95%

According to the standard operating procedure, the donor I-11 (16.4 mg, 0.049 mmol, 1.2 equivalents), the trivalent iodine reagent IV-1 (20.5 mg, 0.062 mmol, 1.5 equivalents), and the molecular sieve were added to the reaction bottle. CuBr was added, and until I-11 was completely converted, the acceptor II-08 (20 mg, 0.041 mmol, 1.0 equivalent) and TfOH were added. After the reaction was completed, a compound III-15 (29.6 mg, 95%) was obtained as a colorless syrup after treatment. $^1$H NMR (600 MHz, CDCl$_3$) δ 7.47 (2H, d, J=7.2 Hz, Ar—H), 7.35-7.30 (8H, m, Ar—H), 5.18 (2H, m, H-4', H-2'), 5.02 (1H, d, J=10.8 Hz, PhCH$_2$), 4.95 (1H, dd, J=3.6, 10.8 Hz, H-3'), 4.89 (1H, d, J=11.4 Hz, PhCH$_2$), 4.82 (1H, d, J=7.8 Hz, H-i'), 4.79 (1H, d, J=12.0 Hz, PhCH$_2$), 4.64 (1H, d, J=12.6 Hz, PhCH$_2$), 4.58 (1H, d, J=3.6 Hz, H-1), 3.93 (1H, t, J=9.0 Hz, H-3), 3.83 (1H, dd, H-6a, H—H-4), 3.78 (1H, dd, J=4.2, 11.4 Hz, H-6b), 3.59 (1H, dq, H-5'), 3.55 (1H, m, H-5), 3.47 (1H, dd, J=3.6, 9.6 Hz, H-2), 3.38 (3H, s, OMe), 2.17 (3H, s), 2.08 (3H, s), 2.00 (3H, s), 1.08 (3H, d, J=6.0 Hz, CH$_3$), 0.91 (9H, s, C(CH$_3$)$_3$), 0.09 (3H, s, CH$_3$), 0.07 (3H, s, CH$_3$). $^{13}$C NMR (150 MHz, CDCl$_3$) δ 170.69, 170.26, 169.37, 139.36, 138.34, 128.35, 128.07, 127.99, 127.75, 127.59, 127.24, 100.23, 97.93, 80.03, 79.69, 76.65, 75.19, 73.45, 71.72, 70.94, 70.37, 70.03, 69.07, 61.55, 55.08, 25.86, 20.91, 20.71, 20.65, 18.24, 16.01, −5.06, −5.25. HRMS (ESI+): calc. for C$_{39}$H$_{56}$NaO$_{13}$Si [M+Na]$^+$783.3382, found: 783.3366.

EXAMPLE 68: Preparation of a Compound III-16 by Glycosylation with the Trivalent Iodine Reagent

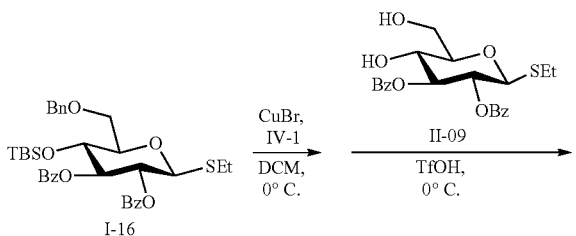

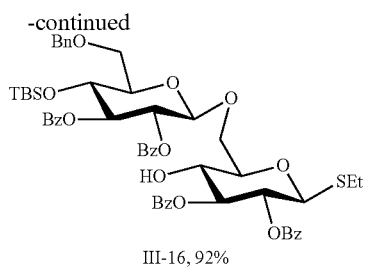

III-16, 92%

According to the standard operating procedure for the reaction, the donor I-16 (33.1 mg, 0.052 mmol, 1.0 equivalent), the trivalent iodine reagent IV-1 (26.1 mg, 0.078 mmol, 1.5 equivalent), and the molecular sieves were added to the reaction bottle. CuBr was added, and until I-16 was completely converted, the acceptor II-09 (27.0 mg, 0.062 mmol, 1.2 equivalents) and TfOH were added. After the reaction was completed, a white solid compound III-16 (48.2 mg, 92%) was obtained after treatment. $^1$H NMR (400 MHz, CDCl$_3$) δ 7.92-7.90 (m, 4H, Ar—H), 7.88-7.84 (m, 4H, Ar—H), 7.50-7.43 (m, 3H, Ar—H), 7.41-7.36 (m, 1H, Ar—H), 7.36-7.23 (m, 13H, Ar—H), 5.55 (t, J=9.6 Hz, 1H, H-3'), 5.43 (t, J=9.2 Hz, 1H, H-3), 5.33 (t, J=9.2 Hz, 2H, H-2, H-2'), 4.85 (d, J=8.0 Hz, 1H, H-i'), 4.60 (d, J=9.6 Hz, 1H, H-1), 4.54 (d, J=12.0 Hz, 1H, PhCH$_2$), 4.46 (d, J=12.0 Hz, 1H, PhCH$_2$), 4.14 (dd, J=4.2, 11.6 Hz, 1H), 4.00 (t, J=8.8 Hz, H-4'), 3.98 (dd, J=4.0, 11.2 Hz, 1H), 3.88 (t, J=9.6 Hz, 1H, H-4), 3.84 (d, J=4.0 Hz, 1H, OH), 3.75-3.69 (m, 2H), 3.67-3.60 (m, 2H), 2.68-2.52 (m, 2H, SCH$_2$), 1.14 (t, J=7.6 Hz, 3H, CH$_3$), 0.69 (s, 9H), −0.05 (s, 3H), −0.25 (s, 3H). $^{13}$C NMR (150 MHz, CDCl$_3$) δ 166.97, 165.94, 165.51, 165.45, 137.80, 133.42, 133.30, 133.25, 133.19, 130.04, 129.96, 129.87, 129.85, 129.82, 129.53, 129.44, 129.37, 128.54, 128.49, 128.46, 128.43, 128.42, 128.14, 127.92, 100.90, 83.56, 79.59, 77.55, 76.55, 75.95, 73.68, 71.91, 70.51, 69.98, 69.42, 68.57, 68.07, 25.71, 24.20, 17.95, 14.84, −4.12, −4.66. HRMS (ESI+): calc. for C$_{55}$H$_{62}$NaO$_{14}$SSi [M+Na]$^+$1029.3522, found: 1029.3500.

EXAMPLE 69: Preparation of a Compound III-17 by Glycosylation with the Trivalent Iodine Reagent

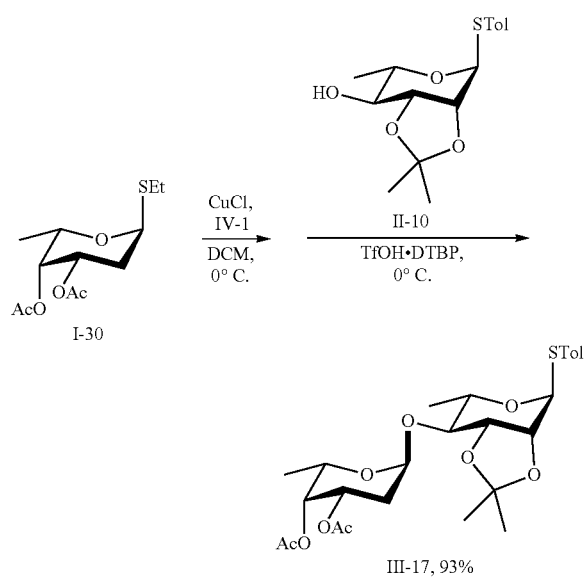

III-17, 93%

According to the standard operating procedure for the reaction, the donor I-30 (14.4 mg, 0.052 mmol, 1.2 equivalents), the trivalent iodine reagent IV-1 (21.6 mg, 0.065 mol, 1.5 equivalents), and the molecular sieve were added to the reaction bottle. CuCl was added, and until I-30 was completely converted, the acceptor II-10 (13.3 mg, 0.043 mmol, 1.0 equivalent) and TfOH·DTBP were added. After the reaction was completed, a white solid compound III-17 (30 mg, 93%) was obtained after treatment. $^1$H NMR (400 MHz, CDCl$_3$) δ 7.34 (2H, d, J=8.4 Hz Ar—CH), 7.11 (3H, m, J=8.0 Hz, Ar—CH), 5.64 (1H, s, H-1), 5.59 (1H, d, J=3.2 Hz,H-4), 5.20 (1H, ddd, J=3.2, 5.2, 8.0 Hz, H-3), 5.17 (1H, s, H-i'), 4.28 (1H, d, J=5.6 Hz, H-2'), 4.20 (1H, dd, J=5.6, 7.2 Hz, H-3'), 4.08 (2H, m, H-5, H-5'), 3.54 (1H, dd, J=7.2, 9.6 Hz, H-4'), 3.13 (3H, s), 2.13 (3H, s), 2.07 (1H, td, H-2a), 1.97 (3H, s), 1.87 (1H, dq, H-2b), 1.51 (3H, s), 1.32 (3H, s), 1.19 (3H, d, J=6 Hz), 1.10 (3H, d, J=6.4 Hz). $^{13}$C NMR (100 MHz, CDCl$_3$) δ 170.94, 170.37, 138.15, 132.73, 130.06, 129.61, 109.82, 96.15, 84.26, 78.70, 77.55, 77.23, 76.91, 76.84, 69.96, 66.81, 65.73, 65.31, 30.19, 28.16, 26.74, 21.34, 21.15, 20.99, 18.15, 16.70. HRMS (ESI+): calc. for C$_{26}$H$_{36}$NaO$_9$S [M+Na]$^+$547.1972, found: 547.1962.

EXAMPLE 70: Preparation of a Compound III-18 by Glycosylation with the Trivalent Iodine Reagent

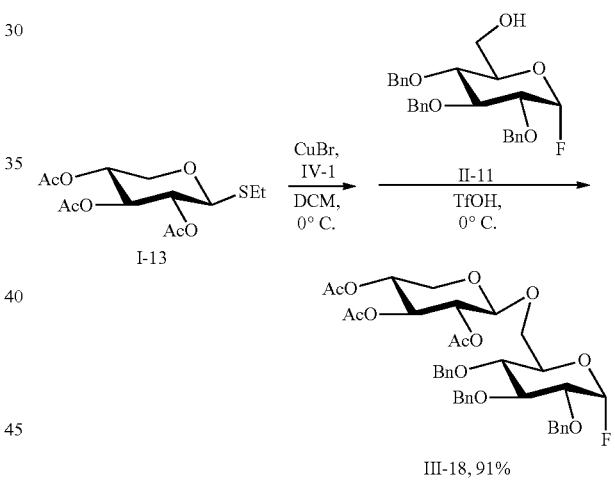

III-18, 91%

According to the standard operating procedure for the reaction, the donor I-13 (16.7 mg, 0.052 mmol, 1.2 equivalents), the trivalent iodine reagent IV-1 (21.6 mg, 0.065 mol, 1.5 equivalents), and the molecular sieve were added to the reaction bottle. CuBr was added, and until I-13 was completely converted, the acceptor II-11 (19.5 mg, 0.043 mmol, 1.0 equivalent) and TfOH were added. After the reaction was completed, a white solid compound III-18 (27.8 mg, 91%) was obtained after treatment. $^1$H NMR (400 MHz, CDCl$_3$) δ 7.33-7.22 (15H, m, Ar—H), 5.50 (1H, dd, J=2.8, 53.2 Hz, H-1), 5.13 (1H, t, J=8.8, 8.4 Hz), 4.94 (3H, m), 4.80 (3H, m, PhCH$_2$), 4.67 (1H, d, J=12.0 Hz, PhCH$_2$), 4.53 (1H, d, J=10.8 Hz, PhCH$_2$), 4.48 (1H, d, J=6.8 Hz), 4.09 (1H, dd, J=4.8, 11.6 Hz, H-6a), 4.00 (1H, dd, J=1.6, 11.2 Hz, H-6b), 3.95 (1H, t, J=9.2, 9.6 Hz), 3.90 (1H, m, H-5), 3.76 (1H, dd, J=3.6, 11.2 Hz, H-5a'), 3.57 (1H, t, J=9.6, 10.0 Hz), 3.50 (1H, ddd, J=2.4, 9.6, 12.0 Hz, H-2), 3.29 (1H, dd, J=8.8, 11.6 Hz, H-5b'), 2.02 (3H, s, CH$_3$), 2.02 (3H, s, CH$_3$), 1.99 (3H, s, CH$_3$), 1.92 (3H, s, CH$_3$). $^{13}$C NMR (100 MHz, CDCl$_3$) δ

170.33, 170.00, 169.46, 138.58, 138.07, 137.76, 128.78, 128.64, 128.32, 128.26, 128.19, 128.10, 127.94, 106.77, 100.61, 81.48, 79.51 (d, J=20 Hz), 76.69, 76.00, 75.34, 73.79, 72.44, 72.40, 71.77, 70.96, 68.91, 67.19, 20.94, 20.91, 20.84. HRMS (ESI+): calc. for $C_{38}H_{43}FNaOI_2$ [M+Na]$^+$733.2631, found: 733.2611.

EXAMPLE 71: Preparation of a Compound III-19 by Glycosylation with the Trivalent Iodine Reagent

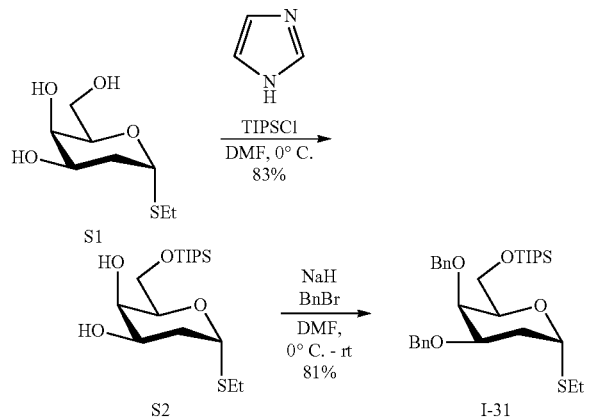

A compound Si (350 mg, 1.68 mmol) and imidazole (286 mg, 4.2 mmol) were dissolved in DMF and placed in 0° C. water, and TIPSCl was added. After the reaction was completed, the mixture was washed with saturated NH$_4$Cl, water, and saturated NaCl in sequence. The organic phase was dried over anhydrous sodium sulfate, concentrated in vacuo, and purified by silica gel column chromatography to obtain a white solid S2 (507 mg, 83%). $^1$H NMR (600 MHz, CDCl$_3$) δ 4.45 (d, J=3.5 Hz, 1H), 4.31 (d, J=9.7 Hz, 1H), 4.27 (d, J=1.9 Hz, 2H), 3.68 (t, J=9.3 Hz, 1H), 3.52 (td, J=10.1, 3.5 Hz, 1H), 3.48 (d, J=1.0 Hz, 1H), 2.82-2.72 (m, 3H), 2.58 (s, 1H), 1.63 (s, 1H), 1.31 (t, J=7.4 Hz, 3H), 1.05 (d, J=3.9 Hz, 18H). $^{13}$C NMR (150 MHz, CDCl$_3$) δ 86.37, 75.59, 75.18, 72.81, 70.78, 67.23, 27.70, 27.50, 24.85, 23.47, 20.77, 15.29. HRMS (ESI+): calc. for $C_{17}H_{36}NaO_4SSi$+[M+Na]$^+$387.1996, found: 387.1990.

A compound S2 (20 mg, 0.055 mmol) was dissolved in DMF and placed in 0° C. water, NaH (6.6 mg, 0.16 mmol) and BnBr (28 mg, 0.16 mmol) were added, and the mixture was slowly heated to room temperature. After the reaction was completed, methanol was added to terminate the reaction, and the mixture was extracted with ethyl acetate, washed with water and saturated NaCl in sequence. The organic phase was dried over anhydrous sodium sulfate, concentrated in vacuo, and purified by silica gel column chromatography to obtain a colorless syrup I-31 (26 mg, 81%). $^1$H NMR (600 MHz, CDCl$_3$) δ7.40-7.37 (6H, m, Ar—H), 7.33 (3H, m, Ar—H), 7.28 (1H, m, Ar—H), 5.53 (1H, d, J=5.4 Hz, H-1), 4.96 (1H, d, J=11.4 Hz, PhCH$_2$), 4.70 (1H, d, J=11.4 Hz, PhCH$_2$), 4.64 (1H, d, J=12.0 Hz, PhCH$_2$), 4.11 (1H, t, J=6.6 Hz, H-3), 3.96 (1H, s, H-4), 3.80 (1H, m, H-5), 3.80 (1H, dd, J=6.6, 10.2 Hz), 3.79 (1H, dd, J=10.2, 6.6 Hz), 2.66 (1H, ddd, H-2a), 2.53 (2H, m, SCH$_2$), 1.99 (1H, dd, J=4.2, 13.2 Hz, H-2b), 1.27 (3H, t, J=7.2 Hz, CH$_3$), 1.07 (21H, m, TIPS). $^{13}$C NMR (150 MHz, CDCl$_3$) δ 138.60, 138.57, 128.60, 128.57, 128.44, 127.96, 127.84, 85.43, 82.94, 77.65, 75.96, 75.17, 71.12, 70.20, 67.60, 27.79, 27.76, 25.41, 23.56, 20.82, 15.27. HRMS (ESI+): calc. for $C_{3}1H_{48}NaO_4SSi$+[M+Na]$^+$567.2935, found: 567.2924.

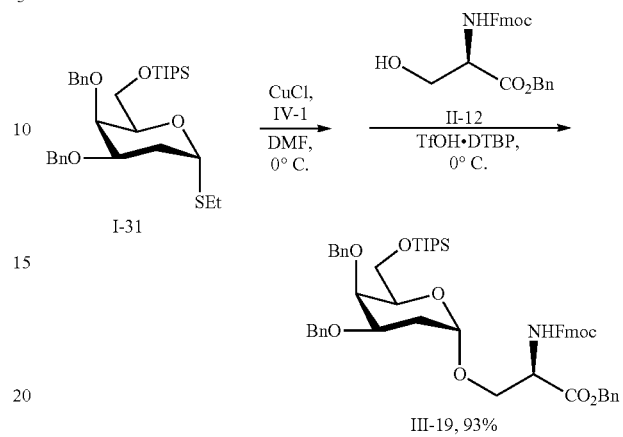

According to the standard operating procedure for the reaction, the donor I-31 (47 mg, 0.086 mmol, 2.0 equivalents), the trivalent iodine reagent IV-1 (43.2 mg, 0.13 mmol, 3.0 equivalents), and the molecular sieve were added to the reaction bottle. CuCl was added, and until I-31 was completely converted, the acceptor II-12 (18.0 mg, 0.043 mmol, 1.0 equivalent) and TfOH were added. After the reaction was completed, a white solid compound III-19 (36.0 mg, 93%) was obtained after treatment. $^1$H NMR (400 MHz, CDCl$_3$) δ 7.75 (d, J=7.6 Hz, 2H, Ar—H), 7.58 (d, J=7.2 Hz, 2H, Ar—H), 7.38 (t, J=7.6 Hz, 2H, Ar—H), 7.30 (m, 12H, Ar—H), 5.65 (d, J=8.8 Hz, 1H, NH), 5.28 (d, J=12.0 Hz, 1H, PhCH$_2$), 5.11 (d, J=12.0 Hz, 1H, PhCH$_2$), 4.90 (d, J=11.6 Hz, 1H, PhCH$_2$), 4.76 (d, J=2.8 Hz, 1H, H-1), 4.64 (d, J=11.6 Hz, 1H, PhCH$_2$), 4.60-4.49 (m, 4H), 4.42 (dd, J=7.2, 10.4 Hz, 1H, H-6a), 4.32 (dd, J=7.2, 10.4 Hz, 1H), 4.22 (t, J=7.2 Hz, 1H), 3.90 (s, 1H, H-4), 3.85 (t, J=4.0 Hz, 2H), 3.78 (m, 1H, H-5), 3.70 (m, 2H), 3.63 (t, J=6.0 Hz, 1H), 2.08 (td, J=3.6, 12.4 Hz, 1H, H-2a), 1.76 (dd, J=4.0, 12.8 Hz, 1H, H-2b), 1.02-0.98 (m, 21H, OTIPS). $^{13}$C NMR (100 MHz, CDCl$_3$) δ 170.36, 156.14, 143.98, 143.93, 141.42, 139.04, 138.55, 135.47, 128.77, 128.72, 128.57, 128.54, 128.34, 128.32, 127.87, 127.74, 127.63, 127.52, 127.22, 125.26, 125.21, 120.13, 99.00, 74.68, 74.50, 72.74, 72.44, 70.55, 68.28, 67.42, 62.77, 54.55, 47.26, 30.95, 18.11, 11.98. HRMS (ESI+): calc. for $C_{54}H_{65}NNaO_9Si$ [M+Na]+ 922.4321, found: 922.4313.

EXAMPLE 72: Preparation of a Compound III-20 by Glycosylation with the Trivalent Iodine Reagent

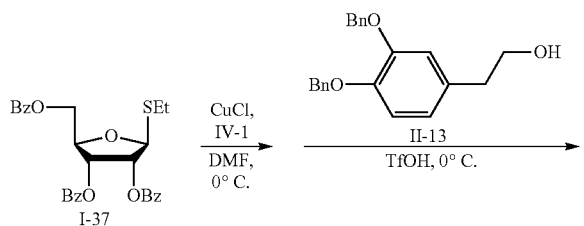

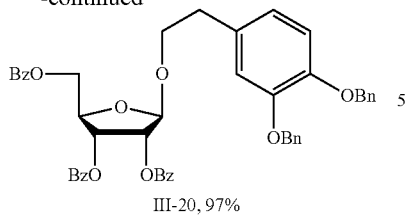

III-20, 97%

According to the standard operating procedure for the reaction, the donor I-37 (36.4 mg, 0.071 mmol, 1.2 equivalents), the trivalent iodine reagent IV-1 (29.7 mg, 0.089 mmol, 1.5 equivalents), and the molecular sieve were added to the reaction bottle. CuCl was added, and until I-37 was completely converted, the acceptor II-13 (20 mg, 0.59 mmol, 1.0 equivalent) and TfOH were added. After the reaction was completed, a colorless syrup compound III-20 (45.2 mg, 97%) was obtained after treatment. $^1$H NMR (600 MHz, CDCl$_3$) δ 8.05 (dd, J=1.2, 8.4 Hz, 2H, Ar—H), 8.00 (dd, J=1.2, 8.4 Hz, 2H, Ar—H), 7.88 (dd, J=1.2, 7.8 Hz, 2H, Ar—H), 7.56 (m, 1H, Ar—H), 7.50 (m, 2H, Ar—H), 7.45 (d, J=7.8 Hz, 2H, Ar—H), 7.41 (m, 4H, Ar—H), 7.31 (m, 10H, Ar—H), 6.85 (d, J=8.4 Hz, 1H, Ar—H), 6.79 (d, J=1.8 Hz, 1H, Ar—H), 6.68 (dd, J=1.8, 8.4 Hz, 1H, Ar—H), 5.83 (dd, J=1.8, 7.2 Hz, 1H, H-3), 5.66 (d, J=4.8 Hz, 1H, H-2), 5.22 (s, 1H, H-1), 5.12 (s, 2H, PhCH$_2$), 5.10 (s, 2H, PhCH$_2$), 4.70 (m, 1H, H-4), 4.57 (dd, J=4.2, 12.0 Hz, 1H, H-5a), 4.41 (dd, J=5.4, 12.0 Hz, 1H, H-5b), 3.92 (dt, J=6.6, 9.0 Hz, OCH$_2$), 3.60 (dt, J=7.2, 9.0 Hz, 1H, OCH$_2$), 2.79-2.68 (m, 2H, CH$_2$). $^{13}$C NMR (150 MHz, CDCl$_3$) δ 166.25, 165.51, 165.39, 149.10, 147.73, 137.65, 137.54, 133.60, 133.49, 133.26, 132.00, 129.92, 129.90, 129.85, 129.37, 129.09, 128.61, 128.53, 128.50, 128.48, 127.82, 127.78, 127.54, 127.43, 121.91, 116.11, 115.51, 105.46, 78.95, 75.68, 72.75, 71.62, 71.44, 69.29, 65.03, 35.62. HRMS (ESI+): calc. for C$_{45}$H$_{42}$NaO$_{10}$ [M+Na]$^+$ 801.2670, found: 801.2693.

EXAMPLE 73: Preparation of a Compound III-21 by Glycosylation with the Trivalent Iodine Reagent

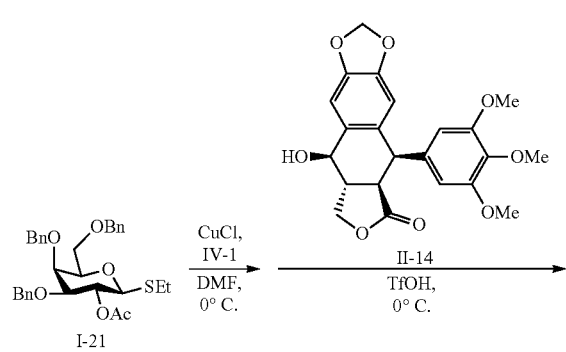

I-21

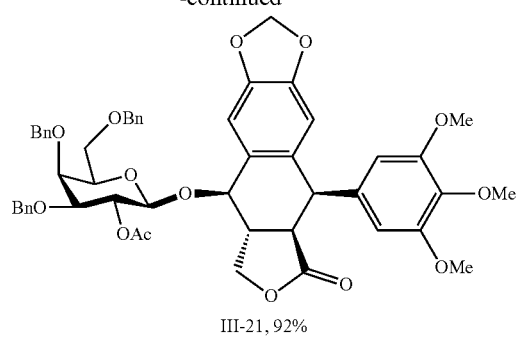

III-21, 92%

According to t the standard operating procedure for the reaction, the donor I-21 (31.1 mg, 0.058 mmol, 1.2 equivalents), the trivalent iodine reagent IV-1 (24.2 mg, 0.072 mmol, 1.5 equivalents), and the molecular sieve were added to the reaction bottle. CuCl was added, and until I-21 was completely converted, the acceptor II-14 (20.0 mg, 0.048 mmol, 1.0 equivalent) and TfOH were added. After the reaction was completed, a colorless syrup compound III-21 (39.5 mg, 92%) was obtained after treatment. $^1$H NMR (600 MHz, CDCl$_3$) δ 7.36-7.27 (13H, m, Ar—CH), 7.22 (2H, m, Ar—CH), 7.16 (1H, s, Ar—CH), 6.47 (1H, s, Ar—CH), 6.35 (2H, s, Ar—CH), 5.96 (1H, d, J=1.2 Hz), 5.94 (1H, d, J=1.2 Hz), 5.42 (1H, dd, J=7.8, 10.2 Hz, H-2), 4.93 (1H, d, J=12.0 Hz, PhCH$_2$), 4.87 (1H, d, J=9.6 H), 4.67 (1H, d, J=12.0 Hz, PhCH$_2$), 4.59 (1H, d, J=11.4 Hz, PhCH$_2$), 4.56-4.54 (2H, m), 4.50 (1H, d, J=12.0 Hz, PhCH$_2$), 4.41 (1H, d, J=9.6 Hz, H-1), 4.40 (1H, d, J=11.4 Hz, PhCH2), 4.38 (1H, d, J=12.0 Hz, PhCH$_2$), 4.05 (1H, dd, J=9.0, 10.2 Hz), 3.93 (1H, d, J=3.0 Hz, H-4), 3.78 (3H, s, OCH$_3$), 3.73 (6H, s, OCH$_3$), 3.61 (1H, dd, J=6.0, 9.0 Hz, H-6a), 3.56 (1H, dd, J=6.0, 9.0 Hz, H-6b), 3.52 (1H, t, J=6.0 Hz, H-5), 3.49 (1H, dd, J=3.0, 10.2 Hz, H-3), 2.89-2.83 (1H, m), 2.76 (1H, dd, J=4.2, 14.4 Hz), 2.00 (3H, s, COCH$_3$).

EXAMPLE 74: Preparation of a Compound III-22 by Glycosylation with the Trivalent Iodine Reagent

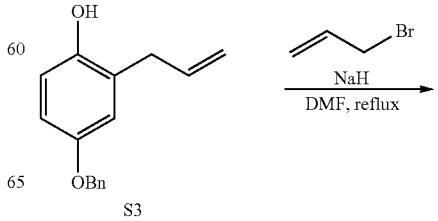

S3

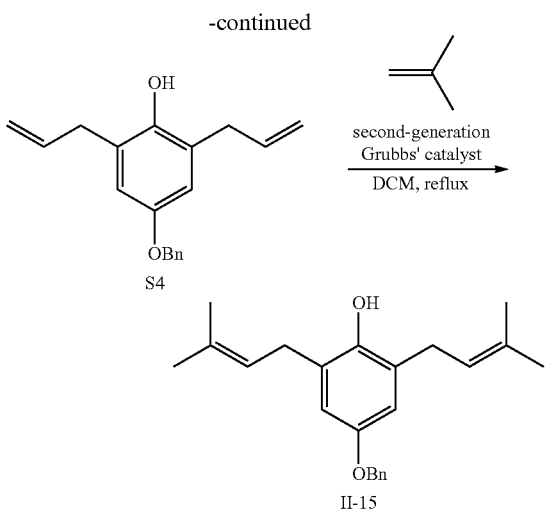

A compound S3 (350 mg, 1.5 mmol) was dissolved in DMF, NaH (58.4 mg, 1.5 mmol) and allyl bromide (0.25 mL, 3.0 mmol) were added, and the mixture was heated to reflux. After the reaction of the raw materials was completed, the organic phase was washed with saturated NaOH and saturated NaCl in sequence, and then dried over anhydrous $Na_2SO_4$. After being concentrated in vacuo and purified by silica gel column chromatography, a yellow oily liquid S4 (364 mg, 89%) was obtained. $^1H$ NMR (600 MHz, $CDCl_3$) δ 7.45 (2H, d, J=7.8 Hz, Ar—H), 7.41 (2H, t, J=7.8 Hz, Ar—H), 7.35 (1H, t, J=7.2 Hz, Ar—H), 6.70 (2H, s, Ar—H), 6.02 (2H, m, CH), 5.18 (4H, m, $CH_2$), 5.02 (2H, s, $PhCH_2$), 4.80 (1H, s, OH), 3.40 (4H, d, J=6.6 Hz, $ArCH_2$). $^{13}C$ NMR (150 MHz, $CDCl_3$) δ 152.81, 146.79, 137.49, 136.51, 128.65, 128.00, 127.71, 126.98, 116.62, 115.07, 70.73, 35.60. HRMS (ESI+): calc. for $C_{19}H_{20}NaO_2$ $[M+Na]^+$ 303.1356, found: 303.1350.

A compound S4 (100 mg, 0.36 mmol) was dissolved in DCM, 2-methyl-2-butene (1.9 mL, 17.8 mmol) and second generation Grubbs catalyst (30.3 mg, 0.04 mmol) were added, and the mixture was heated to reflux. After the reaction was completed, the raw materials were concentrated in vacuo, and then purified by silica gel column chromatography to obtain II-15 (96 mg, 80%). $^1H$ NMR (600 MHz, $CDCl_3$) δ 7.42 (dd, J=0.8, 8.4 Hz, 2H, Ar—H), 7.37 (m, 2H, Ar—H), 7.31 (m, 1H, Ar—H), 6.63 (s, 2H, Ar—H), 5.29 (m, 2H, CH), 4.98 (s, 2H, $PhCH_2$), 4.95 (s, 1H, OH), 3.31 (d, J=7.2 Hz, 4H, $CH_2$), 1.76 (s, 3H), 1.75 (s, 3H), 1.74 (s, 6H). $^{13}C$ NMR (150 MHz, $CDCl_3$) δ 152.59, 146.84, 137.66, 134.53, 128.66, 128.29, 127.95, 127.71, 122.01, 114.20, 70.73, 29.93, 25.95, 17.99.

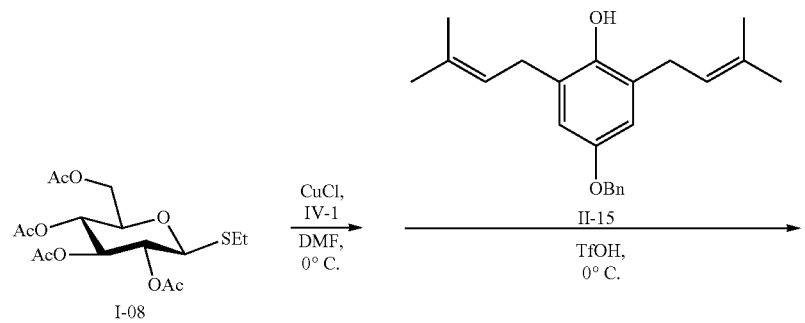

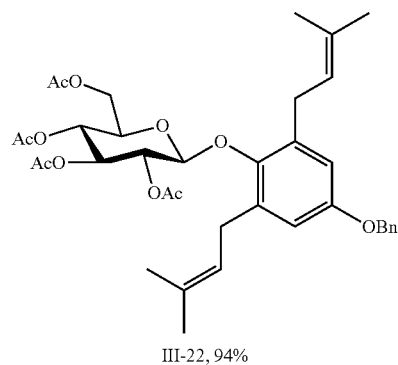

According to the standard operating procedure for the reaction, the donor I-08 (15.4 mg, 0.039 mmol, 1.2 equivalents), the trivalent iodine reagent IV-1 (16.5 mg, 0.050 mmol, 1.5 equivalents), and the molecular sieve were added to the reaction bottle. CuCl was added, and until I-08 was completely converted, the acceptor II-15 (11 mg, 0.033 mmol, 1.0 equivalent) and TfOH were added. After the reaction was completed, a white solid compound III-22 (20.7 mg, 94%) was obtained after treatment. $^1$H NMR (600 MHz, CDCl$_3$) δ 7.43 (m, 2H, Ar—H), 7.40 (m, 2H, Ar—H), 7.34 (m, 1H), 6.63 (s, 2H), 6.63 (s, 2H, Ar—H), 5.35 (dd, J=7.8, 9.0 Hz, 1H, H-2), 5.26 (t, J=9.6 Hz, 1H, H-3), 5.22 (m, 2H, CH), 5.21 (t, J=9.6 Hz, 1H, H-4), 5.00 (s, 2H, PhCH$_2$), 4.81 (d, J=7.8 Hz, 1H), 4.81 (d, J=8.0 Hz, 1H), 4.23 (dd, J=12.3, 4.3 Hz, 1H), 4.22(dd, J=4.2, 12.0 Hz, 1H, H-6a), 4.09 (dd, J=2.4, 12.0 Hz, 1H, H-6b), 3.58 (m, 1H, H-5), 3.42 (dd, J=7.8, 15.6 Hz, 2H, Ar—CH$_2$), 3.34 (dd, J=6.6, 16.2 Hz, ArCH$_2$), 2.11 (s, 3H), 2.06 (s, 3H), 2.05 (s, 3H), 2.04 (s, 3H), 1.76 (s, 6H), 1.70 (s, 6H). $^{13}$C NMR (150 MHz, CDCl$_3$) δ 170.76, 170.52, 169.54, 169.44, 155.96, 145.65, 137.28, 136.37, 133.05, 128.69, 128.08, 127.77, 127.75, 122.66, 113.57, 102.23, 73.21, 71.91, 71.78, 70.29, 68.45, 61.81, 28.73, 25.87, 20.83, 20.78, 20.75, 20.73, 17.97. HRMS (ESI+): calc. for C$_{37}$H$_{46}$NaO$_{11}$ [M+Na]$^+$ 689.2932, found: 689.2922.

EXAMPLE 75: Preparation of a Compound III-23 by Glycosylation with the Trivalent Iodine Reagent According to the standard operating procedure for the reaction, the donor I-33 (30 mg, 0.029 mmol, 1.0 equivalent), the trivalent iodine reagent IV-1 (38.4 mg, 0.116 mol, 4.0 equivalent), and the molecular sieve were added to the reaction bottle. CuCl was added, and until I-33 was completely converted, the acceptor II-16 (17.0 mg, 0.057 mmol, 2.0 equivalents) and BF$_3$·Et$_2$O were added. After the reaction was completed, a white solid compound III-23 (34.5 mg, 94%) was obtained. $^1$H NMR (600 MHz, CDCl$_3$) δ 8.02 (d, J=7.8 Hz, 2H), 7.98 (d, J=8.4 Hz, 2H), 7.80 (d, J=7.8 Hz, 2H), 7.58 (t, J=7.2 Hz, 1H), 7.49 (t, J=7.2 Hz, 1H), 7.39-7.07 (m, 31H), 5.99 (dd, J=9.6, 3.0 Hz, 1H), 5.79 (s, 1H), 5.70 (s, 1H), 5.44 (s, 1H), 5.36 (s, 1H), 4.98 (d, J=7.8 Hz, 1H), 4.80 (d, J=10.8 Hz, 1H), 4.73 (t, J=10.2 Hz, 1H), 4.63 (m, J=12.0 Hz, 2H), 4.57 (d, J=11.6 Hz, 2H), 4.49-4.44 (m, 2H), 4.38 (d, J=12.0 Hz, 1H), 4.31 (d, J=10.8 Hz, 1H), 4.11-4.08 (m, 1H), 4.04-3.96 (m, 3H), 3.90-3.88 (m, 1H), 3.80-3.75 (m, 2H), 3.71 (s, 3H), 3.59 (d, J=10.8 Hz, 1H), 3.06 (qd, J=13.8, 5.4 Hz, 2H), 1.44 (s, 9H).

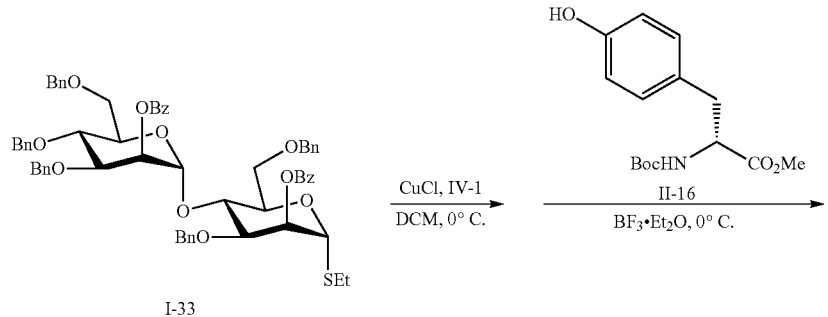

I-33

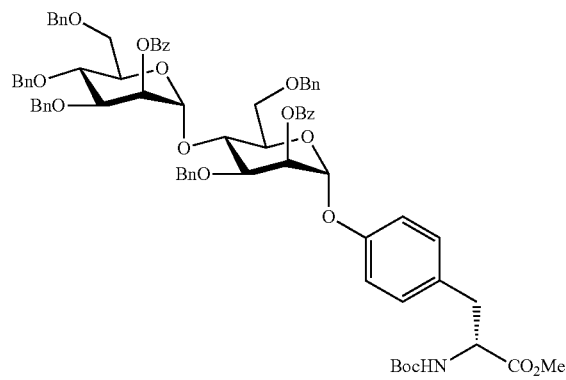

III-23, 94%

EXAMPLE 76: Preparation of a Compound III-24 by Glycosylation with the Trivalent Iodine Reagent

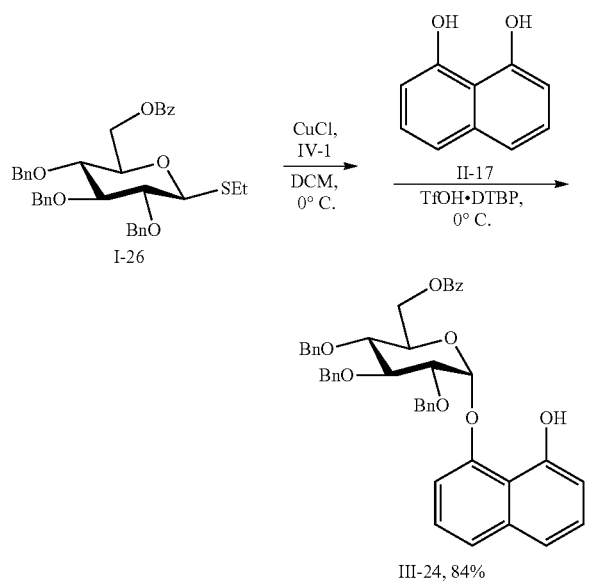

According to the standard operating procedure for the reaction, the donor I-26 (31.1 mg, 0.052 mmol, 1.0 equivalent), the trivalent iodine reagent IV-3 (21.6 mg, 0.065 mmol, 1.5 equivalent), and the molecular sieve were added to the reaction bottle. CuCl was added, and until I-26 was completely converted, the acceptor II-17 (16.7 mg, 0.104 mmol, 2.0 equivalents) and TfOH·DTBP were added. After the reaction was completed, a white solid compound III-24 (27.5 mg, 76%) was obtained after treatment. $^1$H NMR (600 MHz, CDCl$_3$) δ 9.45 (s, 1H, OH), 7.90-7.88 (m, 2H, Ar—H), 7.57-7.54 (m, 1H, Ar—H), 7.46-7.43 (m, 3H, Ar—H), 7.41-7.37 (m, 5H, Ar—H), 7.36-7.30 (m, l0H, Ar—H), 7.20-7.16 (m, 3H, Ar—H), 7.00 (t, J=6.4 Hz, 1H, Ar—H), 6.95 (d, J=7.8 Hz, Ar—H), 5.51 (d, J=3.6 Hz, 1H, H-1), 5.05 (d, J=11.4 Hz, 1H, PhCH$_2$), 5.00 (d, J=11.4 Hz, 1H, PhCH$_2$), 4.91 (d, J=12.0 Hz, 1H, PhCH$_2$), 4.85 (d, J=11.4 Hz, 1H, PhCH$_2$), 4.77 (d, J=12.6 Hz, 1H, PhCH$_2$), 4.69 (d, J=11.4 Hz, 1H, PhCH$_2$), 4.49 (dd, J=6.6, 9.6 Hz), 4.30 (dd, J=3.6, 9.6 Hz, 1H), 4.27-4.23 (m, 2H), 4.14 (dd, J=3.0, 10.2 Hz, H-2), 3.97 (d, J=2.4 Hz, 1H). $^{13}$C NMR (150 MHz, CDCl$_3$) δ 165.99, 154.17, 154.02, 138.25, 137.84, 137.47, 136.67, 133.12, 129.68, 129.63, 129.62, 128.56, 128.49, 128.46, 128.45, 128.34, 128.21, 128.01, 127.98, 127.83, 127.77, 127.62, 125.71, 123.31, 118.96, 115.75, 111.21, 109.74, 99.31, 79.10, 75.88, 74.76, 74.46, 74.14, 73.85, 69.90, 63.90. HRMS (ESI+): calc. for C$_{44}$H$_{40}$NaO$_8$ [M+Na]$^+$719.2615, found: 719.2627.

EXAMPLE 77: Preparation of a Compound III-25 by Glycosylation with the Trivalent Iodine Reagent

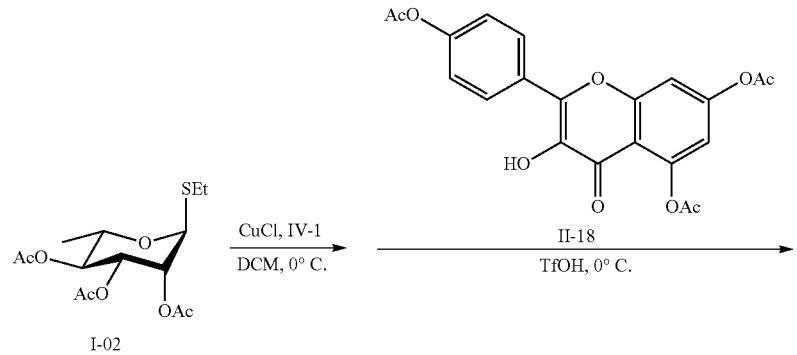

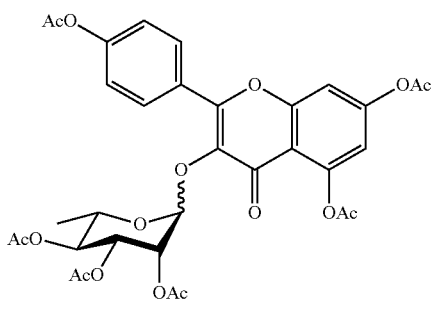

III-25, 74% (α/β 10:1)

According to the standard operating procedure for the reaction, the donor I-02 (28.7 mg, 0.086 mmol, 2.0 equivalents), the trivalent iodine reagent IV-1 (43.1 mg, 0.129 mmol, 3.0 equivalents), and the molecular sieve were added to the reaction bottle. CuCl was added, and until I-02 was completely converted, the acceptor II-18 (17.7 mg, 0.043 mmol, 1.0 equivalent) and TfOH were added. After the reaction was completed, a white solid compound III-25 (21.8 mg, 74%) was obtained after treatment. $^1$H NMR (600 MHz, CDCl$_3$) δ 7.85 (m, 2H, Ar—H), 7.24 (m, 2H, Ar—H), 7.13 (d, J=2.4 Hz, 1H, Ar—H), 6.81 (d, J=1.8 Hz, 1H), 5.92 (dd, J=0.6, 3.0 Hz, 1H, H-2), 5.28 (d, J=0.6 Hz, 1H, H-1), 5.16 (dd, J=3.6, 10.2 Hz, 1H, H-3), 5.12 (t, J=9.0 Hz, 1H, H-4), 3.58 (m, 1H, H-5), 2.34 (s, 3H), 2.34 (s, 3H), 2.33 (s, 3H), 2.29 (s, 3H), 1.29 (d, J=6.0 Hz, 3H). $^{13}$C NMR (150 MHz, CDCl$_3$) δ 170.51, 170.01, 169.90, 169.75, 168.92, 168.09, 167.94, 157.29, 156.18, 154.09, 153.53, 152.74, 134.23, 129.53, 127.16, 122.01, 113.96, 106.52, 97.45, 70.86, 70.78, 70.67, 68.67, 20.99, 20.81, 20.69, 20.64, 17.42. HRMS (ESI+): calc. for C$_{33}$H$_{32}$NaO$_{16}$ [M+Na]$^+$ 707.1583, found: 707.1574.

EXAMPLE 78: Preparation of a Compound III-26 by Glycosylation with the Trivalent Iodine Reagent

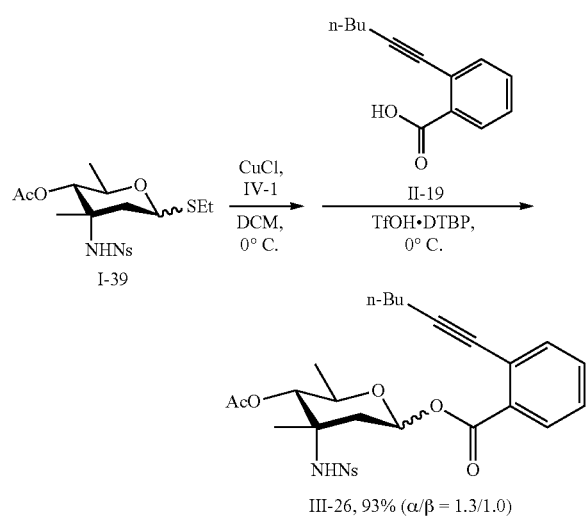

According to the standard operating procedure for the reaction, the donor I-39 (20 mg, 0.046 mmol, 1.0 equivalent), the trivalent iodine reagent IV-1 (23.2 mg, 0.069 mol, 1.5 equivalent), and the molecular sieve were added to the reaction bottle. CuCl was added, and until I-39 was completely converted, the acceptor II-19 (18.6 mg, 0.092 mmol, 2.0 equivalents) and TfOH·DTBP were added. After the reaction was completed, a compound III-26 (20.5 mg, 93%) was obtained as a colorless syrup after treatment. Data of a-configuration product III-26, $^1$H NMR (600 MHz CD$_3$COCD$_3$): δ 8.38-8.34 (m, 2H, -Ph), 8.22 (d, J=7.6 Hz, 1H, -Ph), 8.18-8.15 (m, 2H, -Ph), 7.57-7.39 (m, 2H, -Ph), 7.43-7.39 (m, 1H, -Ph), 6.75 (s, 1H, —NH), 6.38 (d, J=3.6 Hz, 1H, H-1), 4.67 (d, J=10.0 Hz, 1H, H-4), 4.39 (dq, J=6.4, 10.0 Hz, 1H, H-5), 2.81 (dd, J=1.2, 15.2 Hz, 1H, H-2a), overlapped with H$_2$O), 2.51 (t, J=7.2 Hz, 2H), 2.14 (dd, J=3.6, 15.2 Hz, 1H, H-2b), 2.11 (s, 3H, COCH$_3$), 1.67-1.60 (m, 2H), 1.57-1.51 (m, 2H), 1.20 (s, 3H, —CH$_3$—C3), 1.09 (d, J=6.4 Hz, 3H, H-6), 0.96 (t, J=7.6 Hz, 3H, -Me). Data of P-configuration product III-26, $^1$H NMR (600 MHz CD$_3$COCD$_3$): δ 8.45-8.43 (m, 2H, Ph), 8.27 (m, 2H, -Ph), 7.86 (d, J=7.8 Hz, 1H, -Ph), 7.58-7.53 (m, 2H, -Ph), 7.45-7.42 (m, 1H, -Ph), 6.73 (s, 1H, —NH), 6.38 (d, J=1.8, 10.2 Hz, 1H, H-1), 5.04 (m, 1H, H-5), 4.61 (d, J=10.2 Hz, 1H, H-4), 2.85 (dd, J=1.8, 13.8 Hz, 1H, H-2a), 2.51 (t, J=7.2 Hz, 2H), 2.14 (s, 3H, COCH$_3$), 1.94 (dd, J=10.2, 13.8 Hz, 1H, H-2b), 1.66-1.61 (m, 2H), 1.55-1.49 (m, 2H), 1.25 (s, 3H, —CH$_3$—C3), 1.25 (d, J=6.6 Hz, 3H, H-6), 0.96 (t, J=7.8 Hz, 3H, -Me).

EXAMPLE 79: Preparation of a Compound III-27 by Glycosylation with the Trivalent Iodine Reagent

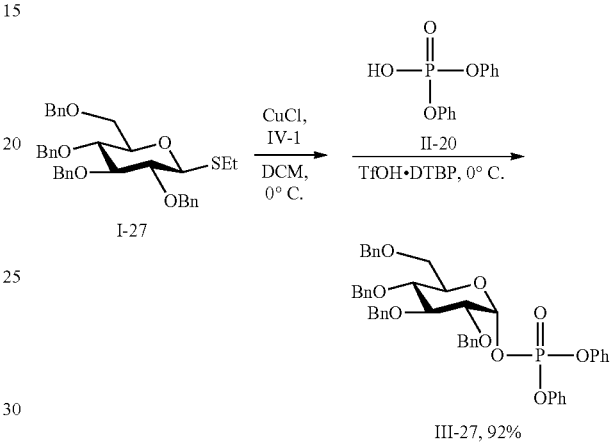

According to the standard operating procedure for the reaction, the donor I-27 (28.0 mg, 0.048 mmol, 1.2 equivalents), the trivalent iodine reagent IV-1 (20.0 mg, 0.06 mol, 1.5 equivalents), and the molecular sieve were added to the reaction bottle. CuCl was added, and until I-27 was completely converted, the acceptor II-20 (10 mg, 0.04 mmol, 1.0 equivalent) and TfOH·DTBP were added. After the reaction was completed, a compound III-27 (28.6 mg, 92%) was obtained as a colorless syrup after treatment. $^1$H NMR (600 MHz, CDCl$_3$) δ 7.33-7.26 (m, 20H), 7.25-7.19 (m, 6H), 7.15-7.11 (m, 4H), 6.06 (dd, J=6.6, 3.0 Hz, 1H), 4.89 (d, J=10.8 Hz, 1H), 4.80 (d, J=10.8 Hz, 1H), 4.78-4.73 (m, 2H), 4.63 (d, J=11.4 Hz, 1H), 4.54 (d, J=12.0 Hz, 1H), 4.48 (d, J=10.8 Hz, 1H), 4.42 (d, J=12.0 Hz, 1H), 3.88 (t, J=9.0 Hz, 1H), 3.77 (dt, J=10.2, 2.4 Hz, 1H), 3.72 (dd, J=10.2, 9.0 Hz, 1H), 3.65-3.61 (m, 2H), 3.35 (dd, J=10.8, 1.8 Hz, 1H).

EXAMPLE 80: Preparation of a Compound III-28 by Glycosylation with the Trivalent Iodine Reagent

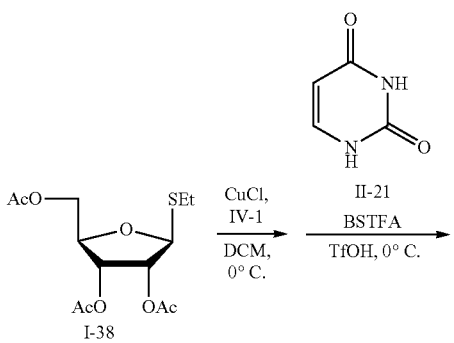

-continued

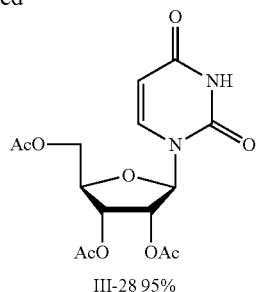

III-28 95%

According to the standard operating procedure for the reaction, the donor I-36 (20 mg, 0.063 mmol, 1.0 equivalent), the trivalent iodine reagent IV-1 (27.1 mg, 0.081 mmol, 1.3 equivalent), and the molecular sieve were added to the reaction bottle. CuCl was added, and until I-36 was completely converted, the acceptor II-21 (32.0 mg, 0.125 mmol, 2.0 equivalents) and BSTFA (0.13 mL, 0.500 mmol, 8.0 equivalents) were stirred in acetonitrile for 30 min and then added to the donor reaction bottle, and then TfOH was added. After the reaction was completed, a compound III-28 (21.9 mg, 95%) was obtained as a colorless syrup after treatment. $^1$H NMR (600 MHz, CDCl$_3$) δ 9.40 (s, 1H, NH), 7.39 (d, J=8.4 Hz, 1H), 6.03 (d, J=4.8 Hz, 1H), 5.78 (d, J=8.4 Hz, 1H), 5.34-5.31 (m, 2H), 4.36-4.31 (m, 3H), 2.13 (s, 3H, —COCH$_3$), 2.12 (s, 3H, —COCH$_3$), 2.09 (s, 3H, —COCH$_3$).

EXAMPLE 81: Preparation of a Compound III-29 by Glycosylation with the Trivalent Iodine Reagent

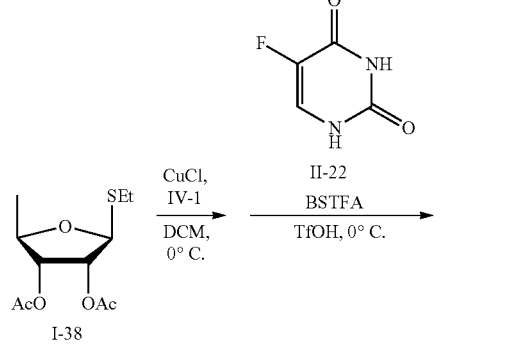

I-38

III-29, 95%

According to the standard operating procedure for the reaction, the donor I-38 (20 mg, 0.076 mmol, 1.0 equivalent), the trivalent iodine reagent IV-1 (38.2 mg, 0.11 mmol, 1.5 equivalent), and the molecular sieve were added to the reaction bottle. CuCl was added, and until I-38 was completely converted, the acceptor II-22 (41.8 mg, 0.15 mmol, 2.0 equivalents) and BSTFA (0.15 mL, 0.6 mmol, 8.0 equivalents) were stirred in acetonitrile for 30 min and then added to the donor reaction bottle, and then TfOH was added. After the reaction was completed, a compound III-29 (23.9 mg, 95%) was obtained as a colorless syrup after treatment. $^1$H NMR (600 MHz, CDCl$_3$) δ 9.61 (brs, 1H), 7.36 (d, J=5.4 Hz, 1H), 5.94 (d, J=4.8 Hz, 1H), 5.29 (t, J=5.4 Hz, 1H), 5.01 (t, J=5.4 Hz, 1H), 4.24-4.19 (m, 1H), 2.11 (s, 3H), 2.09 (s, 3H), 1.45 (d, J=6.6 Hz, 3H).

EXAMPLE 82: Preparation of a Compound III-30 by Glycosylation with the Trivalent Iodine Reagent

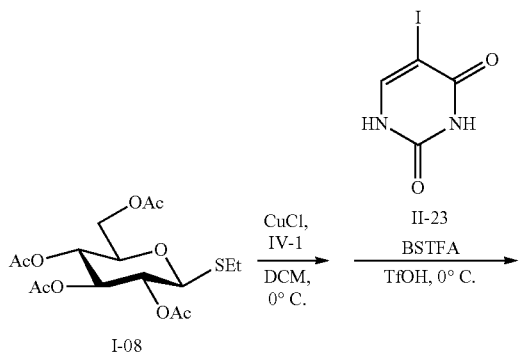

I-08

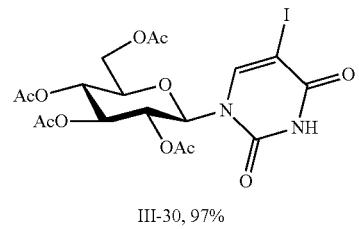

III-30, 97%

According to the standard operating procedure for the reaction, the donor I-08 (20 mg, 0.051 mmol, 1.0 equivalent), the trivalent iodine reagent IV-1 (22.1 mg, 0.066 mmol, 1.3 equivalent), and the molecular sieve were added to the reaction bottle. CuCl was added, and until I-08 was completely converted, the acceptor II-23 (39.0 mg, 0.10 mmol, 2.0 equivalents) and BSTFA (0.10 mL, 0.4 mmol, 8.0 equivalents) were stirred in acetonitrile for 30 min and then added to the donor reaction bottle, and then TfOH was added. After the reaction was completed, a compound III-30 (28.0 mg, 97%) was obtained as a colorless syrup after treatment. $^1$H NMR (600 MHz, CDCl$_3$) δ 9.10 (brs, 1H, NH), 7.78 (s, 1H), 5.87 (d, J=9.6 Hz, 1H, H-1), 5.42 (t, J=9.6 Hz, 1H), 5.20-5.16 (m, 2H), 4.29 (dd, J=12.6, 5.2 Hz, 1H, H-6a), 4.17 (dd, J=12.6, 2.4 Hz, 1H, H-6b), 3.97 (ddd, J 10.2, 5.2, 1.8 Hz, 1H, H-5), 2.13 (s, 3H, —COCH$_3$), 2.08 (s, 3H, —COCH$_3$), 2.04 (s, 3H, —COCH$_3$), 2.03 (s, 3H, —COCH$_3$).

EXAMPLE 83: Preparation of a Compound III-31 by Glycosylation with the Trivalent Iodine Reagent

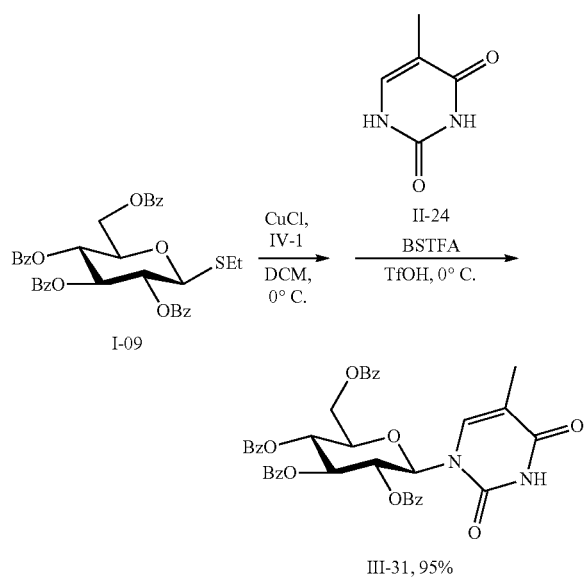

According to the standard operating procedure for the reaction, the donor I-09 (30 mg, 0.047 mmol, 1.0 equivalent), the trivalent iodine reagent IV-1 (20.3 mg, 0.070 mmol, 1.3 equivalent), and the molecular sieve were added to the reaction bottle. CuCl was added, and until I-09 was completely converted, the acceptor II-24 (25.3 mg, 0.094 mmol, 2.0 equivalents) and BSTFA (0.10 mL, 0.376 mmol, 8.0 equivalents) were stirred in acetonitrile for 30 min and then added to the donor reaction bottle, and then TfOH was added. After the reaction was completed, a compound III-31 (31.3 mg, 95%) was obtained as a white solid. $^1$H NMR (600 MHz, CDCl$_3$) δ 8.51 (s, 1H, NH), 8.05-7.26 (m, 21H), 6.26 (d, J=9.6 Hz, 1H, H-1), 6.08 (t, J=9.6 Hz, 1H), 5.78 (t, J=9.6 Hz, 1H), 5.68 (t, J=9.6 Hz, 1H), 4.67 (dd, J=12.6, 2.8 Hz, 1H, H-6a), 4.49 (dd, J=12.6, 5.2 Hz, 1H, H-6b), 4.40 (ddd, J=10.0, 5.2, 2.8 Hz, 1H, H-5), 1.93 (d, J=1.2 Hz, 3H, CH$_3$).

EXAMPLE 84: Preparation of a Compound III-32 by Glycosylation with the Trivalent Iodine Reagent

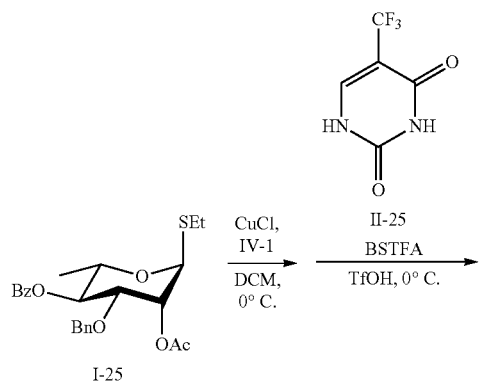

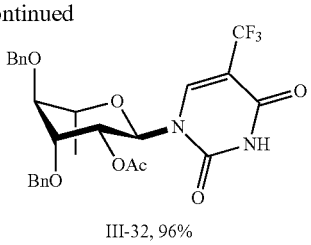

According to the standard operating procedure for the reaction, the donor I-25 (30 mg, 0.070 mmol, 1.0 equivalent), the trivalent iodine reagent IV-1 (30.0 mg, 0.091 mmol, 1.3 equivalent), and the molecular sieve were added to the reaction bottle. CuCl was added, and until I-25 was completely converted, the acceptor II-25 (45.2 mg, 0.139 mmol, 2.0 equivalents) and 20 BSTFA (0.14 mL, 0.556 mmol, 8.0 equivalents) were stirred in acetonitrile for 30 min and then added to the donor reaction bottle, and then TfOH was added. After the reaction was completed, a compound III-32 (37.1 mg, 97%) was obtained as a colorless syrup after treatment. $^1$H NMR (600 MHz, CDCl$_3$) δ 8.40 (brs, 1H), 7.91 (s, 1H), 7.38-7.31 (m, 6H), 7.30-7.26 (m, 4H), 6.27 (d, J=9.6 Hz, 1H, H-1), 5.23 (dd, J=9.6, 3.0 Hz, 1H, H-2), 4.63 (d, J=12.0 Hz, 1H, —CH$_2$Ph), 4.55 (d, J=12.0 Hz, 1H, —CH$_2$Ph), 4.52 (s, 2H, 2x-CH$_2$Ph), 4.34 (q, J=7.2 Hz, 1H, H-5), 4.07 (t, J=3.0 Hz, 1H, H-3), 3.45 (dd, J=3.6, 1.2 Hz, 1H, H-4), 2.02 (s, 3H, —COCH$_3$), 1.48 (d, J=7.2 Hz, 3H, —CH$_3$).

EXAMPLE 85: Preparation of a Compound III-33 by Glycosylation with the Trivalent Iodine Reagent

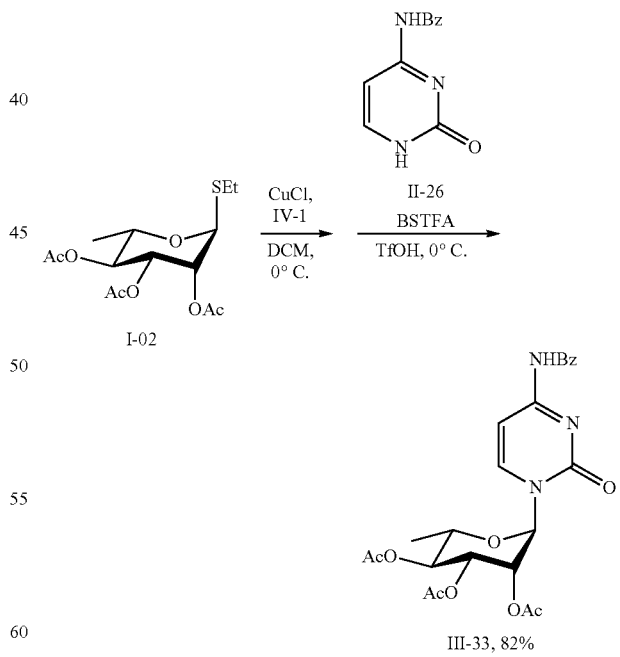

According to the standard operating procedure for the reaction, I-02 (20 mg, 0.060 mmol, 1.0 equivalent), the trivalent iodine reagent IV-1 (26.0 mg, 0.078 mmol, 1.3 equivalent), and the molecular sieve were added to the reaction bottle. CuCl was added, and until 11-02 was completely converted, the acceptor II-26 (34.4 mg, 0.120 mmol, 2.0 equivalents) and BSTFA (0.12 mL, 0.48 mmol, 8.0 equivalents) were stirred in acetonitrile for 30 min and then added to the donor reaction bottle, and then TfOH was added. After the reaction was completed, a compound III-33 (24.0 mg, 82%) was obtained as a colorless syrup after treatment. $^1$H NMR (600 MHz, CDCl$_3$) δ 8.69 (s, 1H, NH), 7.93-7.81 (m, 3H), 7.63-7.49 (m, 4H), 6.46 (d, J=9.6 Hz, 1H), 5.45 (t, J=3.6 Hz, 1H), 5.30 (dd, J=9.6, 3.6 Hz, 1H), 4.86 (dd, J=3.6, 1.2 Hz, 1H), 4.32 (q, J=7.2 Hz, 1H, H-5), 2.21 (s, 3H, —COCH$_3$), 2.19 (s, 3H, —COCH$_3$), 1.96 (s, 3H, —COCH$_3$), 1.58 (d, J=7.2 Hz, 3H, —CH$_3$).

EXAMPLE 86: Preparation of a Compound III-34 by Glycosylation with the Trivalent Iodine Reagent

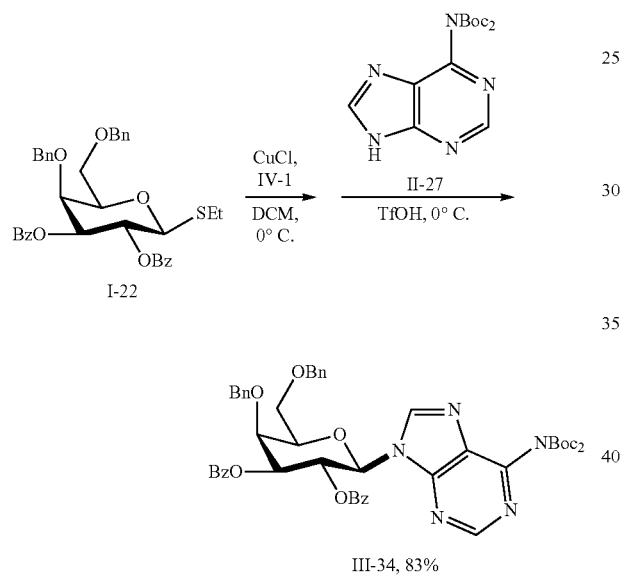

According to the standard operating procedure for the reaction, the donor I-22 (42.8 mg, 0.071 mmol, 1.2 equivalents), the trivalent iodine reagent IV-1 (29.7 mg, 0.089 mmol, 1.5 equivalents), and the molecular sieve were added to the reaction bottle. CuCl was added, and until I-22 was completely converted, the acceptor II-27 (20 mg, 0.059 mmol, 1.0 equivalent) and TfOH were added. After the reaction was complete, a white solid compound III-34 (43.1 mg, 83%) was obtained after treatment. $^1$H NMR (600 MHz, CDCl$_3$) δ 8.70 (s, 1H), 8.42 (s, 1H), 7.73 (d, J=7.2 Hz, 2H), 7.49-7.46 (m, 1H), 7.39-7.27 (m, 12H), 7.24-7.16 (m, 5H), 6.10 (t, J=9.6 Hz, 1H), 5.96 (d, J=9.6 Hz, 1H), 5.05 (d, J=11.4 Hz, 1H), 4.68 (dd, J=12.0, 5.4 Hz, 2H), 4.55 (d, J=12.0 Hz, 1H), 4.47 (q, J=12.0 Hz, 2H), 4.17 (d, J=1.8 Hz, 1H), 3.96 (t, J=6.6 Hz, 1H), 3.92 (dd, J=9.6, 2.4 Hz, 1H), 3.66 (qd, J=9.6, 6.6 Hz, 2H), 1.29 (s, 18H).

EXAMPLE 87: Preparation of a Compound III-35 by Glycosylation with the Trivalent Iodine Reagent

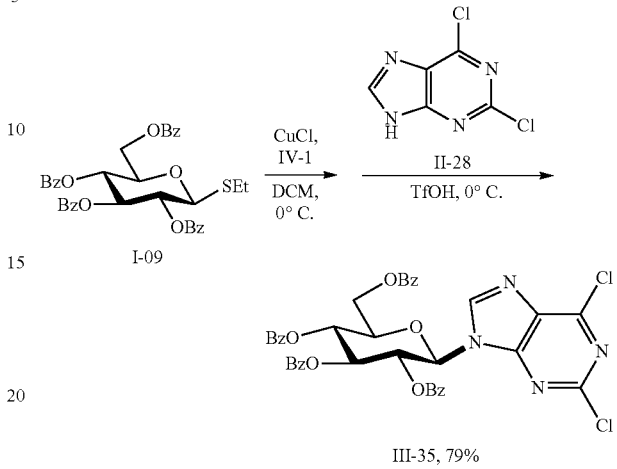

According to the standard operating procedure for the reaction, the donor I-09 (40.7 mg, 0.063 mmol, 1.2 equivalents), the trivalent iodine reagent IV-1 (26.5 mg, 0.079 mol, 1.5 equivalents), and the molecular sieve were added to the reaction bottle. CuCl was added, and until I-09 was completely converted, the acceptor II-28 (10.0 mg, 0.053 mmol, 1.0 equivalent) and TfOH were added. After the reaction was completed, a white solid compound III-35 (32.1 mg, 79%) was obtained after treatment. $^1$H NMR (600 MHz, CDCl$_3$) δ 8.47 (s, 1H), 8.02 (dd, J=8.4, 1.2 Hz, 2H), 7.94 (dd, J=8.4, 1.2 Hz, 2H), 7.82 (dd, J=8.4, 1.2 Hz, 2H), 7.74 (dd, J=8.4, 1.2 Hz, 2H), 7.58-7.26 (m, 12H), 6.27 (d, J=9.6 Hz, 1H, H-1), 6.17 (t, J=9.6 Hz, 1H), 6.03 (t, J=9.6 Hz, 1H), 5.90 (t, J=9.6 Hz, 1H), 4.71-4.67 (m, 1H), 4.55-4.51 (m, 2H).

EXAMPLE 88: Preparation of a Compound III-36 by Glycosylation with the Trivalent Iodine Reagent

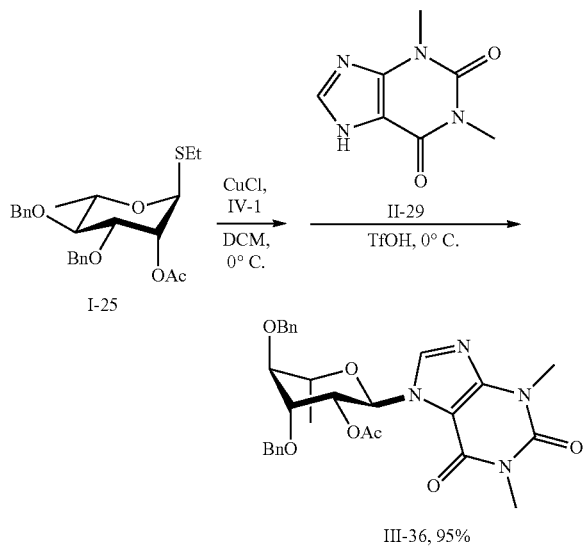

According to the standard operating procedure for the reaction, the donor I-25 (43.0 mg, 0.099 mmol, 1.2 equivalents), the trivalent iodine reagent IV-1 (41.6 mg, 0.124 mmol, 1.5 equivalents), and the molecular sieve were added to the reaction bottle. CuCl was added, and until I-25 was completely converted, the acceptor II-29 (15 mg, 0.083 mmol, 1.0 equivalent) and TfOH were added. After the reaction was complete, a white solid compound III-36 (43.2 mg, 95%) was obtained after treatment. $^1$H NMR (400 MHz, CDCl$_3$) δ 7.78 (s, 1H, CH), 7.37-7.25 (m, I0H, Ar—H), 6.62 (d, J=8.4 Hz, 1H, H-1), 5.70 (dd, J=8.4, 3.2 Hz, 1H, H-2), 4.63 (d, J=12.0 Hz, 1H, —CH$_2$Ph), 4.59 (d, J=12.0 Hz, 1H, —CH$_2$Ph), 4.55 (d, J=12.0 Hz, 1H, —CH$_2$Ph), 4.51 (d, J=12.0 Hz, 1H, —CH$_2$Ph), 4.18-4.10 (m, 1H, H-5), 4.03 (t, J=3.6 Hz, 1H, H-3), 3.57 (s, 3H, —CH3), 3.48 (t, J=4.0 Hz, 1H, H-4), 3.40 (s, 3H, —CH$_3$), 1.93 (s, 3H, —COCH$_3$), 1.48 (d, J=6.8 Hz, 3H, —CH$_3$). $^{13}$C NMR (100 MHz, CDCl$_3$) δ 169.7, 154.9, 151.7, 148.9, 139.9, 137.5, 137.4, 128.7, 128.2, 128.2, 128.2, 128.0, 106.9, 77.7, 75.8, 73.7, 73.3, 72.6, 69.5, 30.0, 28.2, 20.8, 17.1. HRMS (ESI+): calc. for C$_{29}$H$_{32}$N$_4$NaO$_7$ [M+Na]$^+$571.2163, found: 571.2155.

EXAMPLE 89: Preparation of a Compound III-37 by Glycosylation with the Trivalent Iodine Reagent

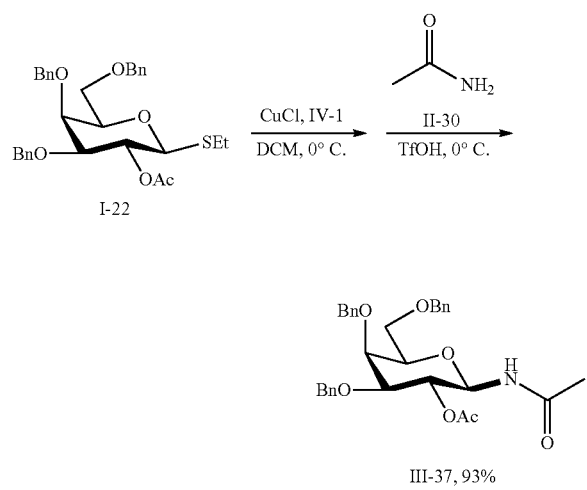

According to the standard operating procedure for the reaction of the reaction, the donor I-22 (60.8 mg, 0.102 mmol, 1.2 equivalents), the trivalent iodine reagent IV-1 (42.4 mg, 0.127 mol, 1.5 equivalents), and the molecular sieve were added to the reaction bottle. CuCl was added, and until I-22 was completely converted, the acceptor II-30 (5.0 mg, 0.085 mmol, 1.0 equivalents) and TfOH were added. After the reaction was completed, a white solid compound III-37 (47.1 mg, 93%) was obtained after treatment. $^1$H NMR (600 MHz, CDCl$_3$) δ 8.00-7.96 (m, 2H, Ar—H), 7.60 (t, J=7.2 Hz, 1H, Ar—H), 7.45 (t, J=7.8 Hz, 2H, Ar—H), 7.37-7.27 (m, I0H, Ar—H), 7.25-7.19 (m, 5H, Ar—H), 6.46-6.42 (m, 1H, NH), 5.52 (t, J=9.6 Hz, 1H, H-2), 5.21 (t, J=9.6 Hz, 1H, H-1), 4.96 (d, J=11.4 Hz, 1H, —CH$_2$Ph), 4.67 (d, J=12.0 Hz, 1H, —CH$_2$Ph), 4.63 (d, J=11.4 Hz, 1H, —CH$_2$Ph), 4.56 (d, J=12.0 Hz, 1H, —CH$_2$Ph), 4.48 (d, J=12.0 Hz, 1H, —CH$_2$Ph), 4.44 (d, J=12.0 Hz, 1H, —CH$_2$Ph), 4.10 (d, J=2.4 Hz, 1H, H-4), 3.81-3.77 (m, 2H, H-3, H-5), 3.66-3.60 (m, 2H, H-6a, H-6b), 1.87 (s, 3H, COCH$_3$).

EXAMPLE 90: Preparation of a Compound III-38 by Glycosylation with the Trivalent Iodine Reagent

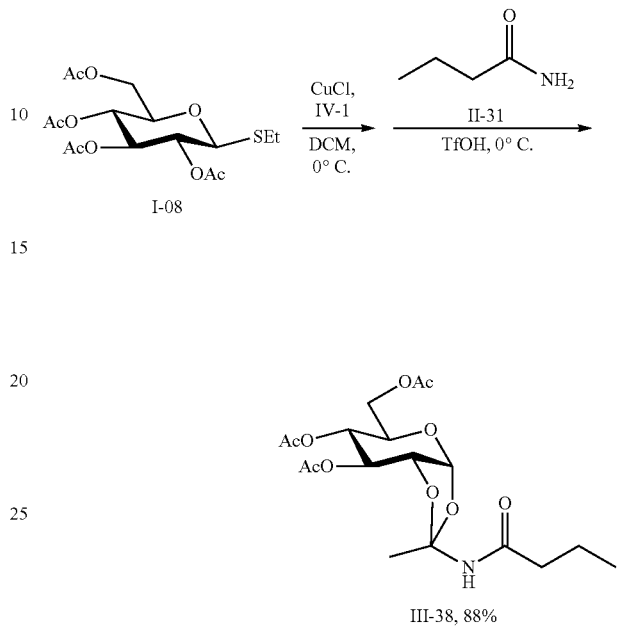

According to the standard operating procedure for the reaction, the donor I-08 (43.3 mg, 0.110 mmol, 1.2 equivalents), the trivalent iodine reagent IV-1 (46.0 mg, 0.138 mol, 1.5 equivalents), and the molecular sieve were added to the reaction bottle. CuCl was added, and until I-08 was completely converted, the acceptor II-31 (8.0 mg, 0.092 mmol, 1.0 equivalent) and TfOH were added. After the reaction was completed, a compound III-38 (33.7 mg, 88%) was obtained as a colorless syrup after treatment. $^1$H NMR (600 MHz, CDCl3) δ 6.08 (s, 1H, NH), 5.81 (d, J=5.2 Hz, 1H, H-1), 5.19 (t, J=3.0 Hz, 1H, H-3), 4.88 (dd, J=9.6, 2.8 Hz, 1H, H-4), 4.46-4.43 (m, 1H, H-2), 4.21-4.16 (m, 2H, H-6a, H-6b), 3.98-3.95 (m, 1H, H-5), 2.10-2.05 (m, 11H), 1.90 (s, 3H, –CH3), 1.65-1.59 (m, 2H), 0.92 (t, J=7.2 Hz, 3H). $^{13}$C NMR (150 MHz, CDCl$_3$) δ 172.2, 170.7, 169.7, 169.2, 110.5, 97.9, 74.2, 70.2, 68.1, 67.3, 63.1, 38.9, 24.7, 20.8, 20.8, 20.8, 18.7, 13.6. HRMS (ESI+): calc. for C$_{18}$H$_{27}$NO$_{10}$ [M+Na]$^+$440.1527, found: 440.1542.

EXAMPLE 91: Preparation of a Compound III-39 by Glycosylation with the Trivalent Iodine Reagent

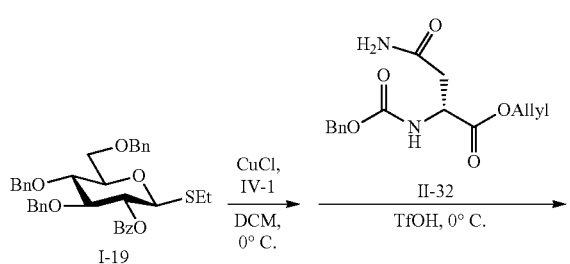

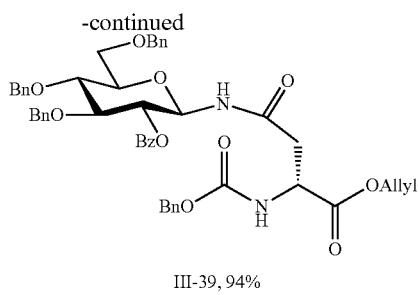

III-39, 94%

According to the standard operating procedure for the reaction, the donor I-19 (29.3 mg, 0.049 mmol, 1.5 equivalents), the trivalent iodine reagent IV-1 (24.0 mg, 0.072 mmol, 2.2 equivalents), and the molecular sieve were added to the reaction bottle. CuCl was added, and until I-19 was completely converted, the acceptor II-32 (10.0 mg, 0.033 mmol, 1.0 equivalent) and TfOH were added. After the reaction was complete, a white solid compound III-39 (25.8 mg, 94%) was obtained after treatment. $^1$H NMR (400 MHz, CDCl$_3$) δ 7.96 (d, J=7.2 Hz, 2H), 7.56 (t, J=7.2 Hz, 1H), 7.41 (t, J=7.6 Hz, 2H), 7.37-7.25 (m, 13H), 7.18-7.06 (m, 7H), 6.51 (d, J=8.8 Hz, 1H), 5.90 (d, J=8.8 Hz, 1H), 5.61-5.51 (m, 1H), 5.21 (t, J=9.2 Hz, 1H), 5.15-5.02 (m, 4H), 4.98 (d, J=10.4 Hz, 1H), 4.77 (d, J=10.8 Hz, 1H), 4.76 (d, J=10.8 Hz, 1H), 4.70 (d, J=11.2 Hz, 1H), 4.64 (d, J=12.0 Hz, 1H), 4.55-4.43 (m, 3H), 4.33 (dd, J=13.2, 5.6 Hz, 1H), 4.18 (dd, J=13.2, 5.6 Hz, 1H), 3.92-3.81 (m, 2H), 3.79-3.71 (m, 2H), 3.57 (d, J=9.2 Hz, 1H), 2.84 (dd, J=16.4, 4.2 Hz, 1H), 2.68 (dd, J=16.4, 4.2 Hz, 1H).

EXAMPLE 92: Preparation of a Compound III-40 by Glycosylation with the Trivalent Iodine Reagent

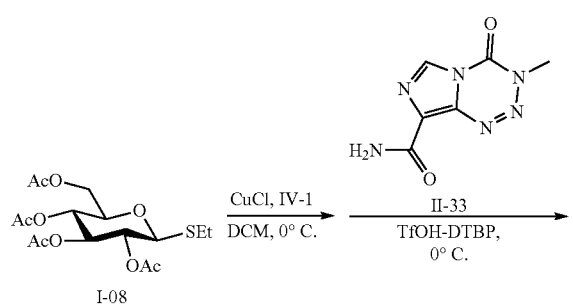

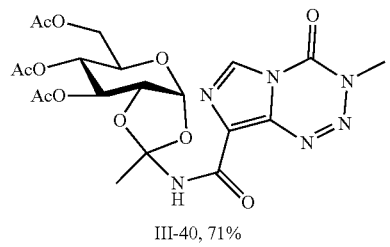

III-40, 71%

According to the standard operating procedure for the reaction, the donor I-08 (20.3 mg, 0.052 mmol, 1.2 equivalents), the trivalent iodine reagent IV-1 (21.6 mg, 0.065 mol, 1.5 equivalents), and the molecular sieve were added to the reaction bottle. CuCl was added, and until I-08 was completely converted, the acceptor II-33 (8.4 mg, 0.043 mmol, 1.0 equivalent) and TfOH·DTBP were added. After the reaction was completed, a compound III-40 (16.1 mg, 71%) was obtained as a colorless syrup after treatment. $^1$H NMR (CDCl$_3$, 600 MHz) δ: 8.37 (1H, s), 7.90 (1H, s), 6.02 (1H, d, J=5.4 Hz), 5.22 (1H, t, J=3.0 Hz), 4.92 (1H, dd, J=2, 4, 9.6 Hz), 4.70 (1H, dd, J=3.0, 4.8 Hz), 4.23 (2H, m), 4.04 (3H, s), 4.02-3.99 (1H, m), 2.11 (6H, m), 2.03 (3H, s).

EXAMPLE 93: Preparation of a Compound III-41 by Glycosylation with the Trivalent Iodine Reagent

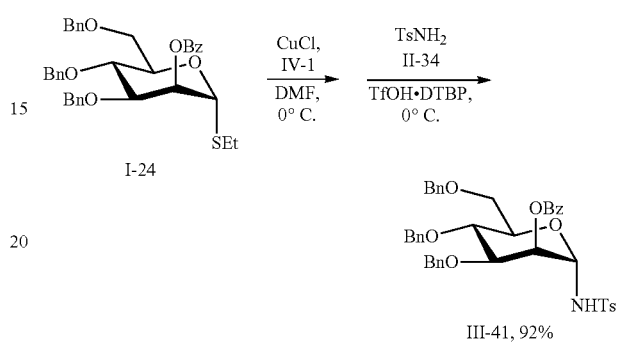

III-41, 92%

According to the standard operating procedure for the reaction, the donor I-24 (42.0 mg, 0.071 mmol, 1.2 equivalents), the trivalent iodine reagent IV-1 (29.3 mg, 0.088 mol, 1.5 equivalents), and the molecular sieve were added to the reaction bottle. CuCl was added, and until I-24 was completely converted, the acceptor II-34 (10.0 mg, 0.058 mmol, 1.0 equivalent) and TfOH were added. After the reaction was completed, a compound III-41 (38.8 mg, 92%) was obtained as white foam after treatment. $^1$H NMR (600 MHz, CDCl3) δ 8.03 (d, J=7.8 Hz, 2H, Ar—H), 7.78 (d, J=7.8 Hz, 2H, Ar—H), 7.56 (t, J=7.2 Hz, 1H, Ar—H), 7.38-7.15 (m, 19H, Ar—H), 5.79 (d, J=8.4 Hz, 1H, NH), 5.63 (d, J=3.0 Hz, 1H, H-2), 5.46 (dd, J=7.8, 3.0 Hz, 1H), 4.72 (t, J=12.0 Hz, 2H, 2x-CH2Ph), 4.59 (d, J=12.0 Hz, 1H, –CH2Ph), 4.50 (d, J=11.4 Hz, 1H, –CH2Ph), 4.47 (d, J=10.8 Hz, 1H, —CH2Ph), 4.43 (d, J=12.0 Hz, 1H, –CH2Ph), 4.01 (t, J=8.4 Hz, 1H, H-4), 3.91-3.87 (m, 1H, H-3), 3.65 (dd, J=10.8, 3.6 Hz, 1H, H-6a), 3.52-3.48 (m, 1H, H-5), 3.22-3.16 (m, 1H, H-6b), 2.34 (s, 3H, CH3). HRMS (ESI+): calc. for C41H41NO8 [M+Na]$^+$730.2445, found: 730.2427.

EXAMPLE 94: Preparation of a Compound III-42 by Glycosylation with the Trivalent Iodine Reagent

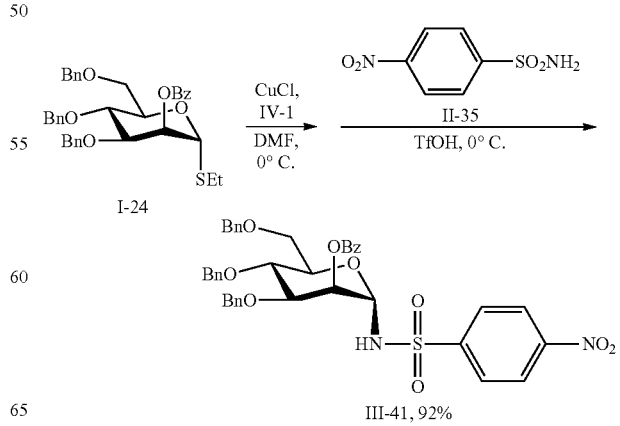

III-41, 92%

According to the standard operating procedure for the reaction, the donor I-24 (31.1 mg, 0.052 mmol, 1.2 equivalents), the trivalent iodine reagent IV-1 (21.6 mg, 0.064 mmol, 1.5 equivalents), and the molecular sieve were added to the reaction bottle. CuCl was added, and until I-24 was completely converted, the acceptor II-35 (8.7 mg, 0.043 mmol, 1.0 equivalent) and TfOH were added. After the reaction was completed, a compound III-42 (29.2 mg, 92%) was obtained as a colorless syrup after treatment. $^1$H NMR (400 MHz, CDCl$_3$) δ 8.09-7.94 (m, 6H, Ar—H), 7.58 (t, J=7.4 Hz, 1H, Ar—H), 7.41-7.22 (m, 15H, Ar—H), 7.19-7.12 (m, 2H, Ar—H), 6.27 (brs, 1H), 5.54 (d, J=6.0 Hz, 2H), 4.72-4.60 (m, 2H), 4.57-4.41 (m, 4H), 3.96-3.80 (m, 2H), 3.79-3.67 (m, 2H), 3.32 (dd, J=9.6, 2.0 Hz, 1H). $^{13}$C NMR (100 MHz, CDCl$_3$) δ 165.9, 150.0, 146.7, 137.9, 137.5, 137.4, 133.8, 130.1, 129.2, 128.8, 128.7, 128.6, 128.2, 128.1, 128.0, 127.9, 124.2, 79.2, 76.6, 74.1, 73.9, 73.9, 73.6, 72.6, 69.1, 68.0. HRMS (ESI+): calc. for C$_{41}$H$_{41}$NNaO$_5$ [M+Na]+761.2139, found: 761.2136.

EXAMPLE 95: Preparation of a Compound III-43 by Glycosylation with the Trivalent Iodine Reagent

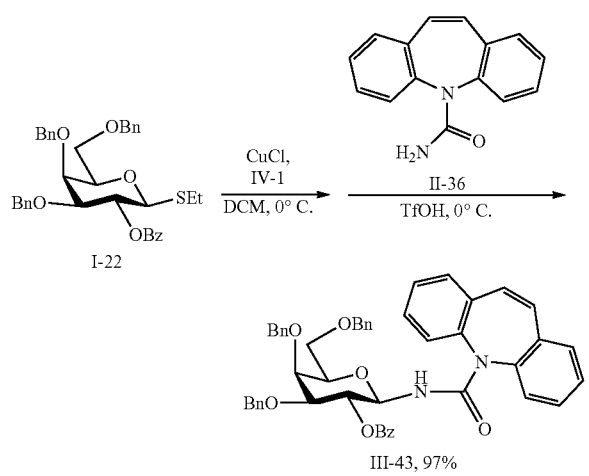

According to the standard operating procedure for the reaction, the donor I-22 (31.1 mg, 0.052 mmol, 1.2 equivalents), the trivalent iodine reagent IV-1 (21.6 mg, 0.064 mmol, 1.5 equivalents), and the molecular sieve were added to the reaction bottle. CuCl was added, and until I-22 was completely converted, the acceptor II-36 (10.2 mg, 0.043 mmol, 1.0 equivalent) and TfOH were added. After the reaction was completed, a white solid compound III-43 (32.2 mg, 97%) was obtained after treatment. $^1$H NMR (600 MHz, CDCl$_3$) δ 8.00 (s, 2H), 7.66 (t, J=7.2 Hz, 1H), 7.52 (t, J=7.8 Hz, 2H), 7.42-7.14 (m, 25H), 5.3-5.29 (m, 2H, NH, H-2), 5.09 (t, J=9.0 Hz, 1H, H-1), 4.89 (d, J=11.4 Hz, 1H, PhCH$_2$), 4.61 (d, J=11.4 Hz, 1H, Ph CH$_2$), 4.60 (d, J=11.4 Hz, 1H, PhCH$_2$), 4.51 (d, J=12.0 Hz, 1H, PhCH$_2$), 4.45 (d, J=12.0 Hz, 1H, PhCH$_2$), 4.43 (d, J=12.0 Hz, 1H, PhCH$_2$), 4.05 (d, J=2.4 Hz, 1H, H-4), 3.73-3.68 (m, 2H, H-3, H-5), 3.65-3.58 (m, 2H). $^{13}$C NMR (150 MHz, CDCl$_3$) δ 166.2, 155.3, 138.4, 137.9, 137.8, 133.4, 130.1, 129.8, 129.5, 128.7, 128.6, 128.5, 128.4, 128.1, 128.1, 127.9, 127.8, 127.8, 127.7, 81.0, 80.3, 75.1, 74.9, 73.6, 73.3, 72.2, 71.3, 67.8. HRMS (ESI+): calc. for C$_{49}$H$_{44}$N$_2$O$_7$ [M+Na]$^+$ 795.3041, found: 795.3021.

EXAMPLE 96: Preparation of a Compound III-44 by Glycosylation with the Trivalent Iodine Reagent

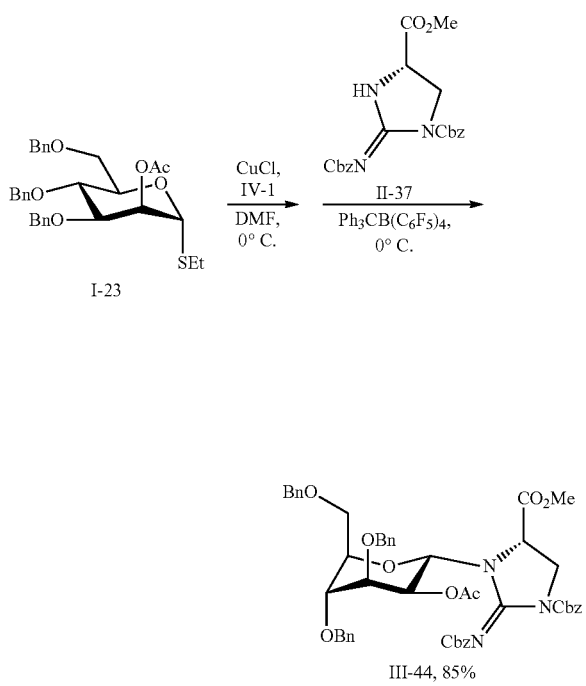

According to the standard operating procedure for the reaction, the donor I-23 (26.1 mg, 0.049 mmol, 2.0 equivalents), the trivalent iodine reagent IV-1 (24.4 mg, 0.073 mmol, 3.0 equivalents), and the molecular sieve were added to the reaction bottle. CuCl was added, and until I-23 was completely converted, the acceptor II-37 (10.0 mg, 0.024 mmol, 1.0 equivalent) and Ph$_3$CB(C$_6$F$_5$)$_4$ were added. After the reaction was completed, a compound III-44 (18.2 mg, 85%) was obtained as a colorless syrup after treatment. $^1$H NMR (600 MHz, CDCl$_3$) δ 7.37-7.24 (m, 23H, Ar—H), 7.18-7.16 (m, 2H, Ar—H), 5.85 (d, J=9.0 Hz, 1H, H-1), 5.17 (d, J=12.0 Hz, 1H), 5.12-5.00 (m, 4H), 4.55-4.45 (m, 5H), 4.40 (t, J=12.4 Hz, 2H), 4.17-4.10 (m, 3H), 4.04 (dd, J 10.8, 3.0 Hz, 1H), 3.82 (dd, J 10.4, 7.2 Hz, 1H), 3.68-3.65 (m, 1H), 3.64 (s, 3H, COOCH$_3$), 3.63-3.60 (m, 1H), 2.01 (s, 3H, COCH$_3$).

EXAMPLE 97: Preparation of a Compound III-45 by Glycosylation with the Trivalent Iodine Reagent

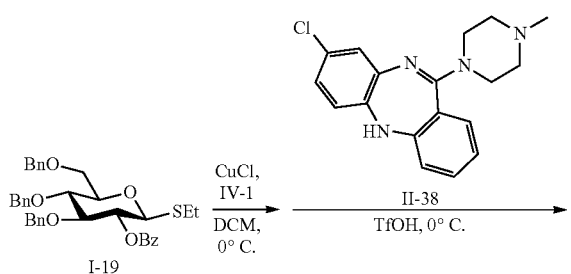

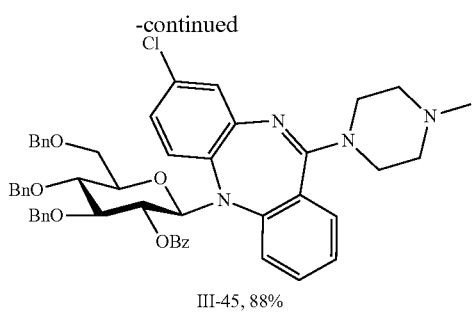

III-45, 88%

According to the standard operating procedure for the reaction, the donor I-19 (33.0 mg, 0.055 mmol, 1.2 equivalents), the trivalent iodine reagent IV-1 (23.0 mg, 0.069 mol, 1.5 equivalents), and the molecular sieve were added to the reaction bottle. CuCl was added, and until I-19 was completely converted, the acceptor II-38 (15.0 mg, 0.046 mmol, 1.0 equivalent) and TfOH were added. After the reaction was completed, a compound III-45 (34.9 mg, 88%) was obtained as a colorless syrup after treatment. tH NMR (600 MHz, CDCl$_3$) δ: 7.92 (d, J=7.2 Hz, 2H, Ar—H), 7.69 (t, J=7.2 Hz, 2H, Ar—H), 7.55 (d, J=7.2 Hz, 2H, Ar—H), 7.42 (m, 4H, Ar—H), 7.37 (t, J=7.2 Hz, 2H, Ar—H), 7.34-7.25 (m, 7H, Ar—H), 7.14 (dd, J=1.2, 7.2 Hz, 1H, Ar—H), 7.10-7.04 (m, 6H, Ar—H), 7.00 (d, J=3.6 Hz, 1H, Ar—H), 6.84 (dd, J=3.0, 9.0 Hz, 1H, Ar—H), 5.48 (t, J=9.0, 9.6 Hz, 1H, H-2), 5.03 (d, J=9.0 Hz, H-1), 4.85 (d, J=10.8 Hz, 1H, PhCH$_2$), 4.73 (d, J=12.0 Hz, 1H, PhCH$_2$), 4.67 (m, 2H, PhCH$_2$), 4.64 (d, J=10.8 Hz, 1H, PhCH$_2$), 4.57 (d, J=10.8 Hz, 1H, PhCH$_2$), 3.95 (m, 2H, H-6a, H-3), 3.87 (dd, J=5.4, 10.2 Hz, 1H, H-6b), 3.82 (t, J=9.0 Hz, 1H, H-4), 3.73 (m, 1H, H-5), 3.08 (s, 2H), 2.67 (s, 2H), 2.21 (s, 4H), 2.16 (s, 3H). $^{13}$C NMR (150 MHz, CDCl$_3$) δ 164.25, 160.87, 153.64, 146.07, 138.49, 138.12, 137.89, 137.44, 133.06, 132.03, 130.84, 130.34, 129.98, 129.32, 128.62, 128.56, 128.31, 128.23, 128.05, 127.77, 127.69, 127.50, 126.12, 125.97, 125.26, 124.96, 123.41, 122.98, 91.26, 84.21, 78.48, 76.53, 75.27, 73.50, 69.54, 55.05, 46.13, 29.85. HRMS (ESI+): calc. for C$_{52}$H$_{51}$ClN$_4$NaO$_6$ [M+Na]$^+$885.3389, found: 885.3372.

EXAMPLE 98: Preparation of a Compound III-46 by Glycosylation with the Trivalent Iodine Reagent

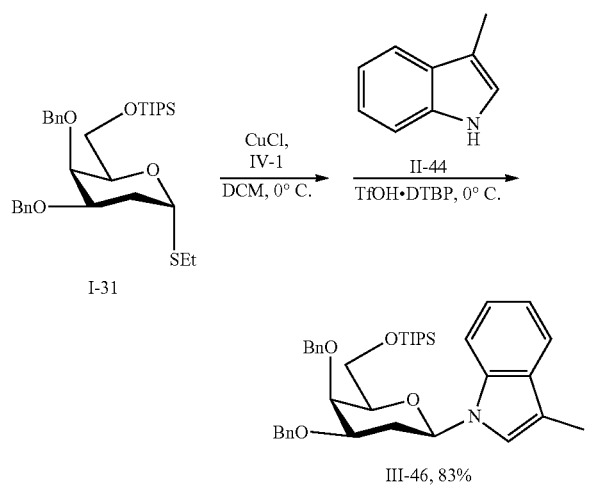

III-46, 83%

According to the standard operating procedure for the reaction, the donor I-31 (46.9 mg, 0.086 mmol, 2.0 equivalents), the trivalent iodine reagent IV-1 (43.1 mg, 0.13 mol, 3.0 equivalents), and the molecular sieve were added to the reaction bottle. CuCl was added, and until I-31 was completely converted, the acceptor II-44 (5.6 mg, 0.043 mmol, 1.0 equivalent) and TfOH·DTBP were added. After the reaction was completed, a white solid compound III-46 (16.5 mg, 83%) was obtained after treatment. $^1$H NMR (600 MHz, CDCl$_3$) δ 7.52 (d, J=7.2 Hz, 1H, Ar—H), 7.45-7.42 (m, 3H, Ar—H), 7.37-7.34 (m, 6H, Ar—H), 7.32-7.28 (m, 2H, Ar—H), 7.16 (t, J=7.2 Hz, 1H, Ar—H), 7.10 (t, J=7.2 Hz, 1H, Ar—H), 7.07 (s, 1H, Ar—H), 5.52 (dd, J=1.8, 11.4 Hz, 1H, H-1), 5.05 (d, J=10.8 Hz, 1H, —CH$_2$Ph), 4.77 (d, J=11.4 Hz, 1H, —CH$_2$Ph), 4.67 (d, J=12.0 Hz, 1H, —CH$_2$Ph), 4.65 (d, J=12.0 Hz, 1H, —CH$_2$Ph), 4.09 (s, 1H), 3.93 (t, J=9.0 Hz, 1H), 3.81 (m, 1H, H-5), 3.78 (dd, 1H, J=5.4, 9.0 Hz, H-6a), 3.63 (dd, 1H, J=5.4, 8.4 Hz, H-6b), 2.82 (q, J=12 Hz, H-2a), 2.28 (s, 3H), 2.19 (m, 1H, H-2b), 1.04 (m, 21H, TIPS). $^{13}$C NMR (151 MHz, CDCl$_3$) δ 139.24, 138.19, 136.05, 129.46, 128.51, 128.17, 127.74, 127.37, 127.32, 122.12, 121.78, 119.51, 118.99, 111.84, 110.17, 81.91, 78.01, 77.71, 74.49, 71.61, 70.31, 61.68, 31.95, 18.01, 11.88, 9.62. HRMS (ESI+): calc. for C$_{35}$H$_{51}$NNaO$_4$Si+[M+Na]$^+$636.3480, found: 636.3465.

EXAMPLE 99: Preparation of a Compound III-47 by Glycosylation with the Trivalent Iodine Reagent

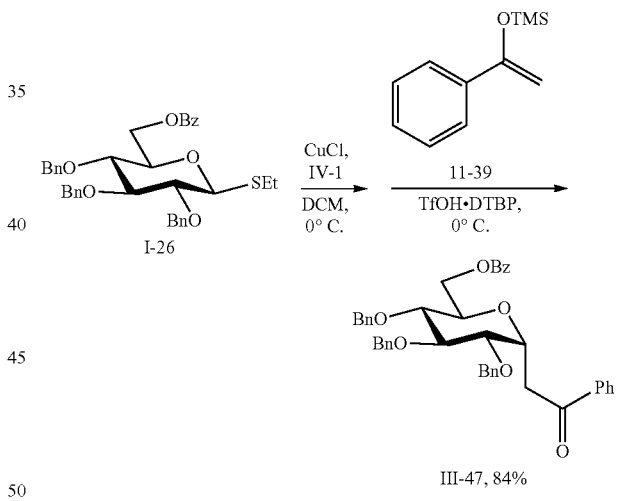

III-47, 84%

According to the standard operating procedure for the reaction, the donor I-26 (31.1 mg, 0.052 mmol, 1.2 equivalents), the trivalent iodine reagent IV-1 (21.6 mg, 0.065 mmol, 1.5 equivalents), and the molecular sieve were added to the reaction bottle. CuCl was added, and until I-26 was completely converted, the acceptor II-39 (8.8 L, 0.043 mmol, 1.0 equivalent) and TfOH·DTBP were added. After the reaction was completed, a white solid compound III-47 (23.7 mg, 84%) was obtained after treatment. $^1$H NMR (600 MHz, CDCl$_3$) δ 7.95 (d, J=7.2 Hz, 2H, Ar—H), 7.86 (d, J=7.2 Hz, 2H, Ar—H), 7.54 (t, J=7.2 Hz, 2H, Ar—H), 7.43-7.38 (m, 4H, Ar—H), 7.36-7.23 (m, 15H, Ar—H), 4.96 (d, J=10.8 Hz, 1H, —CH$_2$Ph), 4.94-4.90 (m, 1H, H-1), 4.89 (d, J=10.8 Hz, 1H, —CH$_2$Ph), 4.84 (d, J=10.8 Hz, 1H, —CH$_2$Ph), 4.71 (d, J=11.4 Hz, 1H, —CH$_2$Ph), 4.66 (d, J=11.4 Hz, 1H, —CH$_2$Ph), 4.61 (d, J=10.8 Hz, 1H, —CH₂Ph), 4.47 (dd, J=12.0, 2.4 Hz, 1H), 4.42 (dd, J 12.0, 4.8 Hz, 1H), 3.95 (ddd, J=9.0, 4.8, 2.4 Hz, 1H, H-5), 3.90-3.85 (m, 2H), 3.61 (t, J=8.4 Hz, 1H), 3.43 (dd, J=15.6, 4.8 Hz, 1H), 3.31 (dd, J=15.6, 8.4 Hz, 1H). ¹³C NMR (150 MHz, CDCl₃) δ 197.5, 166.4, 138.4, 137.9, 137.8, 137.1, 133.3, 133.1, 130.0, 129.8, 128.8, 128.7, 128.6, 128.6, 128.4, 128.3, 128.2, 128.2, 128.1, 128.0, 128.0, 82.1, 79.6, 77.9, 75.6, 75.2, 73.6, 71.2, 71.1, 64.0, 35.8. HRMS (ESI+): calc. for C₄₂H₄₀NaO₇ [M+Na]⁺679.2666, found: 679.2666.

EXAMPLE 100: Preparation of a Compound III-48 by Glycosylation with the Trivalent Iodine Reagent

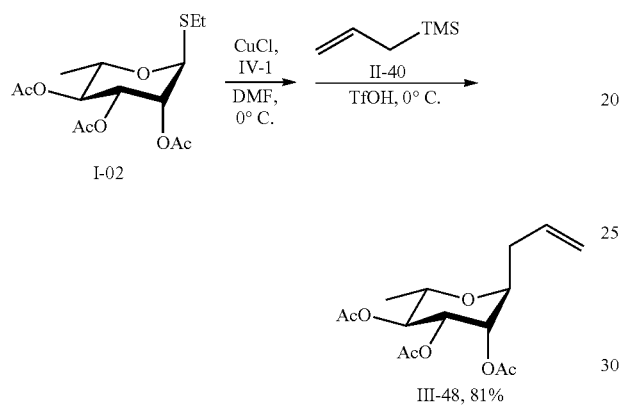

III-48, 81%

According to the standard operating procedure for the reaction, the donor I-02 (20 mg, 0.060 mmol, 1.0 equivalent), the trivalent iodine reagent IV-1 (30.0 mg, 0.09 mmol, 1.3 equivalent), and the molecular sieve were added to the reaction bottle. CuCl was added, and until I-02 was completely converted, the acceptor II-40 (13.7 mg, 0.120 mmol, 2.0 equivalents) and TfOH were added. After the reaction was completed, a compound III-48 (15.2 mg, 81%) was obtained as a colorless syrup after treatment. ¹H NMR (600 MHz, CDCl₃) δ 8.69 (s, 1H, NH), 7.93-7.81 (m, 3H), 7.63-7.49 (m, 4H), 6.46 (d, J=9.6 Hz, 1H), 5.45 (t, J=3.6 Hz, 1H), 5.30 (dd, J=9.6, 3.6 Hz, 1H), 4.86 (dd, J=3.6, 1.2 Hz, 1H), 4.32 (q, J=7.2 Hz, 1H, H-5), 2.21 (s, 3H, —COCH₃), 2.19 (s, 3H, —COCH₃), 1.96 (s, 3H, —COCH₃), 1.58 (d, J=7.2 Hz, 3H, —CH₃).

EXAMPLE 101: Preparation of a Compound III-49 by Glycosylation with the Trivalent Iodine Reagent

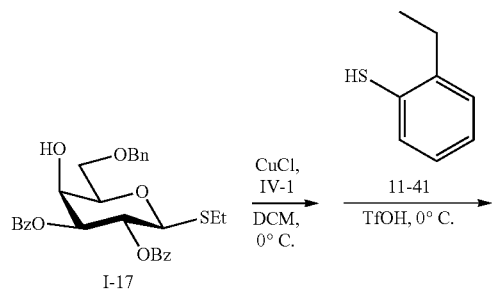

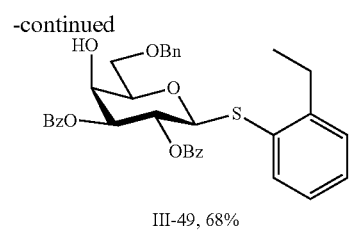

III-49, 68%

According to the standard operating procedure for the reaction, the donor I-17 (80 mg, 0.153 mmol, 1.0 equivalent), the trivalent iodine reagent IV-1 (76.7 mg, 0.230 mol, 1.5 equivalent), and the molecular sieve were added to the reaction bottle. CuCl was added, and until I-17 was completely converted, the acceptor II-41 (31.7 mg, 0.230 mmol, 1.5 equivalents) and TfOH were added. After the reaction was completed, a compound III-49 (62.3 mg, 68%) was obtained as a colorless syrup after treatment. ¹H NMR (400 MHz, CDCl₃) δ 7.96 (d, J=8.4 Hz, 4H, Ar—H), 7.65-7.07 (m, 15H, Ar—H), 5.85 (t, J=10.0 Hz, 1H, H-2), 5.30 (dd, J=10.0, 3.2 Hz, 1H, H-3), 4.86 (d, J=10.0 Hz, 1H, H-1), 4.58 (s, 2H, 2x-CH₂Ph), 4.41 (s, 1H, H-4), 3.88-3.78 (m, 3H), 2.73 (s, 1H, OH), 2.68-2.57 (m, 2H), 0.98 (t, J=7.6 Hz, 3H). HRMS (ESI+): calc. for C₃₅H₃₄NaO₇S [M+Na]⁺621.1917, found: 621.1912.

EXAMPLE 102: Preparation of a Compound III-50 by Glycosylation with the Trivalent Iodine Reagent

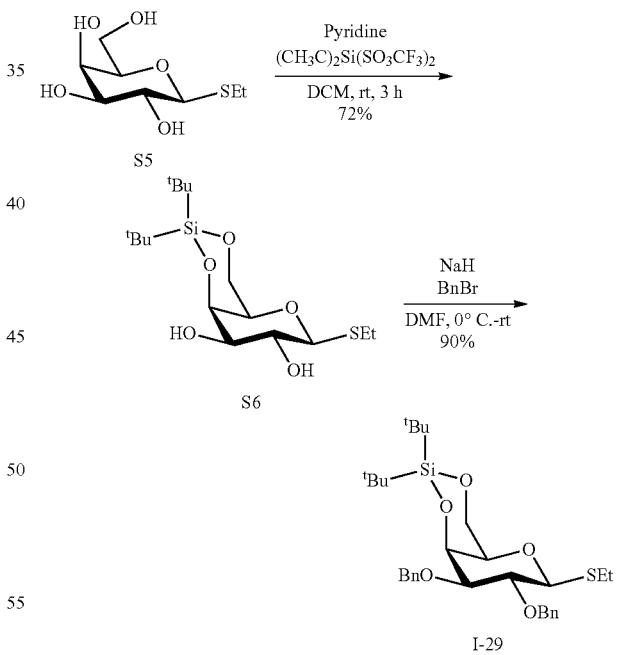

A compound S5 (170 mg, 0.76 mmol) was dissolved in DCM and placed in 0° C. water, and then di-tert-butyl trifluoromethanesulfonic acid silyl ester (0.25 mL, 0.76 mmol) was added. After stirring in water at 0° C. for 30 min, pyridine (0.19 mL, 2.28 mmol) was added and stirred for 15 min. After the reaction was completed, the mixture was extracted with ethyl acetate and washed with water and saturated NaCl in sequence. The organic phase was dried over anhydrous Na₂SO₄, concentrated in vacuo, and purified by silica gel column chromatography to obtain a white solid S6 (254 mg, 72%). ¹H NMR (600 MHz, CDCl₃) δ 4.44 (d, J=3.6 Hz, 1H), 4.31 (d, J=9.6 Hz, 1H, H-1), 4.27 (d, J=1.8 Hz, 2H, H-6), 3.68 (t, J=9.6 Hz, 1H, H-2), 3.52 (m, 1H, H-5), 3.47 (d, J=1.2 Hz, 1H), 2.81-2.72 (m, 3H), 2.58 (br s, 1H, OH), 1.63 (br s, 1H, OH), 1.31 (t, J=7.4 Hz, 3H, CH₃), 1.06 (s, 9H), 1.05 (s, 9H). ¹³C NMR (150 MHz, CDCl₃) δ 86.37, 75.59, 75.18, 72.81, 70.78, 67.23, 27.70, 27.50, 24.85, 23.47, 20.77, 15.29. HRMS (ESI+): calc. for C₁₆H₃₂NaO₅SSi [M+Na]⁺387.1632, found: 387.1642.

A compound S6 was dissolved in DMF and placed in 0° C. water, NaH (104 mg, 2.6 mmol) and BnBr (0.78 mL, 6.5 mmol) were added in sequence, and the temperature was raised to room temperature. After the reaction of the raw materials was completed, methanol was used to terminate the reaction, and the mixture was extracted with ethyl acetate, washed with water and saturated NaCl in sequence. The organic phase was dried over anhydrous Na₂SO₄, concentrated in vacuo, and purified by silica gel column chromatography to obtain a white solid I-29 (268 mg, 90%). ¹H NMR (600 MHz, CDCl₃) δ 7.41 (t, J=7.2 Hz, 4H, Ar—H), 7.33 (m, 4H, Ar—H), 7.29 (m, 2H, Ar—H), 4.85 (s, 2H), 4.77 (d, J=12.0 Hz, 1H, PhCH₂), 4.69 (d, J=12.0 Hz, 1H, PHCH₂), 4.50 (d, J=2.4 Hz, 1H, H-4), 4.40 (d, J=9.6 Hz, 1H, H-1), 4.24 (dd, J=1.2, 12.6 Hz, 1H, H-6a), 4.19 (dd, J=1.8, 12.6 Hz, H-6b), 3.76 (t, J=9.6 Hz, 1H, H-2), 3.45 (dd, J=3.0, 9.6 Hz, 1H, H-3), 3.29 (s, 1H, H-5), 2.70 (m, 2H, SCH₂), 1.29 (t, J=7.8 Hz, 3H, CH₃), 1.10 (s, 9H), 1.07 (s, 9H). 13C NMR (150 MHz, CDCl₃) δ 138.60, 138.57, 128.60, 128.57, 128.44, 127.96, 127.84, 85.43, 82.94, 77.65, 75.96, 75.17, 71.12, 70.20, 67.60, 27.79, 27.76, 25.41, 23.56, 20.82, 15.27. HRMS (ESI+): calc. for C₃₀H₄₄NaO₅SSi [M+Na]⁺567.2571, found: 567.2569.

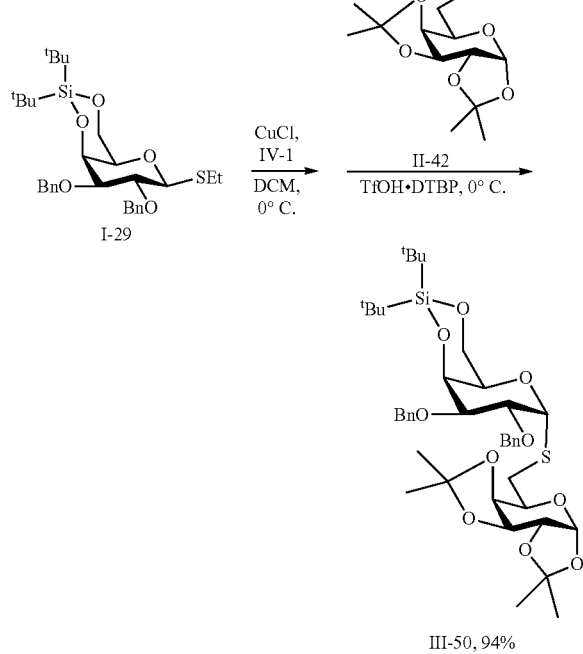

According to the standard operating procedure for the reaction, the donor I-29 (28.1 mg, 0.052 mmol, 1.2 equivalents), the trivalent iodine reagent IV-1 (21.6 mg, 0.065 mmol, 1.5 equivalents), and the molecular sieve were added to the reaction bottle. CuCl was added, and until I-29 was completely converted, the acceptor II-42 (11.9 mg, 0.043 mmol, 1.0 equivalent) and TfOH·DTBP were added. After the reaction was completed, a compound III-50 (30.7 mg, 94%) was obtained as a colorless syrup after treatment. ¹H NMR (600 MHz, CDCl₃) δ 7.42-7.38 (m, 4H, Ar—H), 7.33 (m, 4H, Ar—H), 7.28 (m, 2H, Ar—H), 5.52 (d, J=4.8 Hz, 1H), 5.45 (d, J=5.4 Hz, 1H), 4.78 (d, J=12.0 Hz, 1H, PhCH₂), 4.72 (d, J=12.6 Hz, 3H), 4.59 (dd, J=2.4, 7.8 Hz, 1H), 4.48 (d, J=3.0 Hz, 1H), 4.30 (dd, J=2.4, 5.4 Hz, 1H), 4.26 (dd, J=1.8, 7.8 Hz, 1H), 4.25-4.22 (m, 1H), 4.21 (dd, J=1.8, 10.2 Hz, 1H), 4.08 (dd, J=1.2, 12.0 Hz, 1H), 4.00 (m, 1H), 3.97 (s, 1H), 3.63 (dd, J=2.4, 9.6 Hz, 1H), 2.82 (dd, J=7.8, 13.2 Hz, 1H), 2.73 (dd, J=6.6, 13.2 Hz, 1H), 1.52 (s, 3H), 1.44 (s, 3H), 1.33 (s, 3H), 1.32 (s, 3H), 1.04 (s, 9H), 0.95 (s, 9H). ¹³C NMR (150 MHz, CDCl₃) δ 139.02, 138.34, 128.45, 128.44, 128.29, 127.76, 127.70, 127.59, 109.49, 108.89, 96.88, 85.66, 78.23, 73.72, 72.68, 71.64, 71.27, 71.25, 71.16, 70.69, 68.18, 67.22, 66.53, 30.64, 27.76, 27.40, 26.29, 26.15, 25.09, 24.74, 23.55, 20.81. HRMS (ESI+): calc. for C₄₀H₅₅NaO₁₀SSi [M+Na]⁺781.3412, found: 781.3398.

EXAMPLE 103: Preparation of a Compound III-51 by Glycosylation with the Trivalent Iodine Reagent

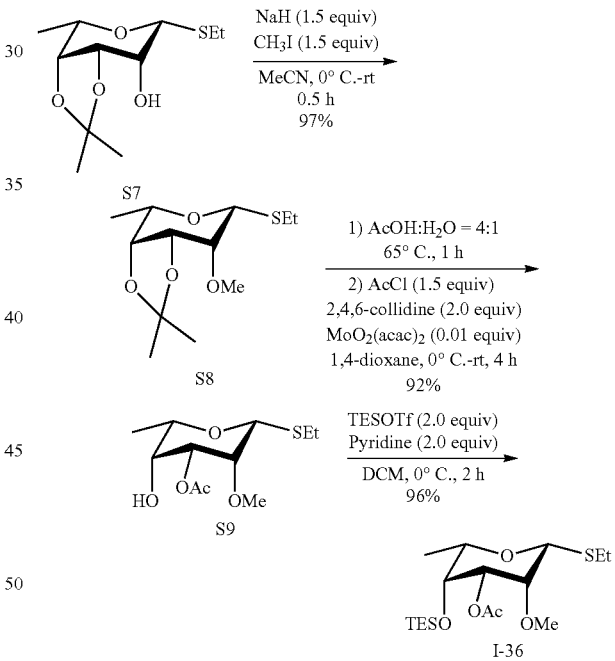

S7 (197 mg, 0.79 mmol, 1.0 equivalent) was weighed into a reaction bottle, degassed with argon, and then acetonitrile was added to dissolve. The mixture was placed in 0° C. water, and NaH (48 mg, 1.19 mmol, 1.5 equivalents) was slowly added into the reaction bottle. After stirring for 10 min, MeI (169 mg, 1.19 mmol, 1.5 equivalents) was added and the mixture was slowly heated to room temperature. After the reaction was completed, methanol was used to terminate the reaction, the solvent was removed by rotary evaporation, the product was diluted with EA, washed twice with H₂O, and once with a saturated NaCl solution, dried over anhydrous sodium sulfate, concentrated, and purified by silica gel column chromatography to obtain a syrupy liquid S8 (221.4 mg, 97%). $^1$H NMR (400 MHz, CDCl$_3$) δ 4.42 (1H, d, J=1.6 Hz, H-1), 4.22 (1H, t, J=5.6 Hz, H-3), 3.92 (1H, dd, J=2.8, 5.6 Hz, H-4), 3.71 (1H, dq, J=2.8, 6.8, Hz, H-5), 3.51(3H, s,—OMe), 3.33 (1H, dd, J=1.6, 5.2 Hz, H-2), 2.05 (2H, m, -SCH$_2$), 1.56 (3H, s, —CH$_3$), 1.40(3H,d, J=6.8, —CH$_3$), 1.34 (3H, s, —CH$_3$). $^{13}$C NMR (100 MHz, CDCl$_3$) δ 110.05, 83.77, 77.09, 74.53, 73.70, 72.70, 61.94, 26.07, 25.60, 16.94, 15.26. HRMS (ESI+): calc. for C$_{12}$H$_{22}$NaO$_4$S [M+Na]$^+$285.1131, found: 285.1127.

S8 (170 mg, 0.65 mmol) was placed in a reaction bottle, and (AcOH: H$_2$O=4:1) was added to dissolve. The mixture was placed at 65° C. and monitored by TLC. After the reaction was completed, the solvent was removed by rotary evaporation, MoO$_2$(acac)$_2$ (4.2 mg, 0.013 mmol, 0.02 equivalent) was added, and then 1,4-dioxane was added to dissolve, placed in an ice bath, 2,4,6-trimethylpyridine (157 mg, 1.3 mmol, 2.0 equivalents) was added, stirred for 10 min, AcCl (152.6 mg, 1.94 mmol, 1.5 equivalents) was added, and slowly heated to room temperature. Monitored by TLC, after the reaction was completed, the reaction was terminated with ice water, the solvent was removed by rotary evaporation, diluted with EA, washed twice with H$_2$O, washed once with HCl (1 M), washed once with saturated NaHCO$_3$, washed once with saturated NaCl solution, dried over anhydrous sodium sulfate, concentrated, and purified by silica gel column chromatography to obtain a liquid S9 (157.6 mg, 92%) as a colorless syrup. $^1$H NMR (400 MHz, CDCl$_3$) δ 4.74 (1H, t, J=3.2 Hz, H-3), 4.52 (1H, d, J=0.4 Hz, H-1), 3.65 (1H, m, H-2), 3.62 (1H, m, H-4), 3.56 (3H, s,—OMe), 3.49 (1H, dq, J=0.8, 6.4, Hz, H-5), 3.42 (1H, d, J=11.2 Hz, —OH), 2.70 (2H, m, —SCH$_2$), 2.13 (3H, s, —OAc), 1.25 (6H, m, —CH$_3$, —SCH$_2$CH$_3$). $^{13}$C NMR (100 MHz, CDCl$_3$) δ 170.55, 84.47, 80.52, 76.34, 73.18, 70.30, 62.44, 25.79, 21.21, 16.92, 15.23. HRMS (ESI+): calc. for C$_{11}$H$_{20}$NaO$_5$S [M+Na]$^+$287.0924 found: 287.0927.

S9 (313 mg, 1.18 mmol, 1.0 equivalent) was placed in a reaction bottle, and DCM was added to dissolve. Pyridine (375 mg, 4.74 mmol, 4.0 equivalents) was added, and the mixture was placed at 0° C., and then TESOTf (626 mg, 2.37 mmol, 2.0 equivalents) was added, and the mixture was monitored by TLC. After the reaction was completed, the solvent was removed by rotary evaporation, the reaction was terminated with saturated NaHCO$_3$, diluted with DCM, washed once with saturated copper sulfate, washed once with H$_2$O, washed once with saturated NaCl solution, dried over anhydrous sodium sulfate, concentrated, and purified by silica gel column chromatography to obtain a yellow syrupy liquid I-36 (430.5 mg, 96%). $^1$H NMR (600 MHz, CDCl$_3$) δ 4.78 (1H, t, J=3.6 Hz, H-3), 4.54 (1H, d, J=1.2 Hz, H-1), 3.73 (1H, m, H-2 or H-4), 3.57 (1H, m, H-2 or H-4), 3.51 (1H, dq, J=0.6, 6.0, Hz, H-5), 3.47 (3H, s,—OMe), 2.69 (2H, m, —SCH$_2$), 2.16 (3H, s, —OAc), 1.28 (6H, m, —CH$_3$, —SCH$_2$CH$_3$), 0.97 (9H, t, J=7.8 Hz, -TES), 0.64 (6H, q, -TES). $^{13}$C NMR (100 MHz, CDCl$_3$) δ 170.52, 85.07, 78.54, 76.23, 74.45, 69.91, 61.75, 29.84, 25.65, 21.35, 17.41, 15.16, 7.08, 5.22. HRMS (ESI+): calc. for C$_{17}$H$_{34}$NaO$_5$SSi [M+Na]$^+$401.1788 found: 401.1790.

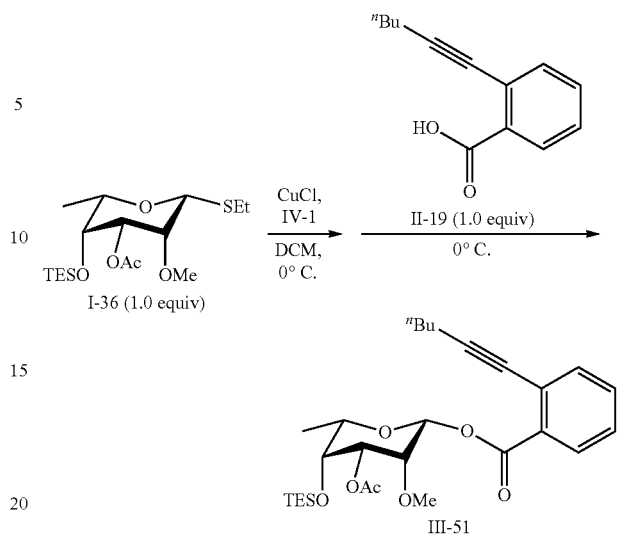

The donor I-36 (15 mg, 0.040 mmol, 1.0 equiv), the trivalent iodine reagent IV-1 (19.9 mg, 0.069 mmol, 1.5 equivalents), and the molecular sieve were added to the reaction bottle. CuCl was added, and until I-36 was completely converted, the acceptor II-19 (8.8 mg, 0.044 mmol, 1.1 equivalents) was added. After the reaction was completed, a compound III-51 (18.1 mg, 87%) was obtained as a colorless syrup after treatment. $^1$H NMR (600 MHz, CDCl$_3$) δ 7.87 (d, J=8.4 Hz, 1H), 7.51 (d, J=7.8 Hz, 1H), 7.43 (t, J=7.8 Hz, 1H), 7.30 (t, J=7.8 Hz 1H), 6.49 (s, 1H), 5.13 (t, J=3.0 Hz, 1H), 4.22 (q, J=6.6 Hz, 1H), 3.85 (s, 1H), 3.56 (s, 1H), 3.51 (s, 3H), 2.44 (m, 2H), 2.15 (s, 3H), 1.62-1.57 (m, 2H), 1.50-1.44 (m, 2H), 1.26 (d, J=6.6 Hz, 3H), 0.93 (t, J=7.2 Hz, 3H), 0.15 (s, 9H).

It will be easily understood by persons skilled in the art that the above description is only preferred embodiments of the disclosure, and the embodiments are not intended to limit the disclosure. Any modifications, equivalent substitutions, and improvements made within the spirit and principles of the disclosure should be included in the protection scope of the disclosure.

What is claimed is:

1. A glycosylation method involving a trivalent iodine reagent, wherein the glycosylation method is a scheme 1 as follows: a glycosyl donor (I) is activated in presence of the trivalent iodine reagent and a transition metal catalyst, and then reacts with a acceptor (II) under acid catalysis to obtain a glycosylation product (III);

a reaction formula is as follows:

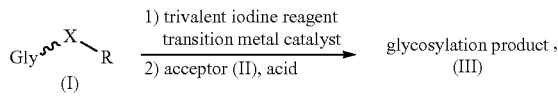

wherein
wherein in the glycosyl donor (I), Gly is a glycosyl group in which one or more hydroxyl groups on a sugar ring are protected by a protecting group; X is an oxygen, sulfur, or selenium atom; R is an alkyl group or an aryl group; the acceptor (II) is a nucleophile selected from sugars, alcohols, phenols, flavonoids, phosphates, pyrimidines, purines, amides, sulfonamides, guanidines, arylamines, indoles, enol silyl ethers, thiols, or thiophenols comprising one or more nucleophilic groups, alternatively, the glycosylation method is a scheme 2 as follows: the glycosyl donor (I) is activated in the presence of the trivalent iodine reagent and the transition metal catalyst, and then reacts with the acceptor (II) to obtain the glycosylation product (III);

a reaction formula is as follows:

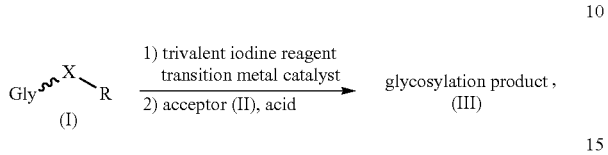

wherein
in the glycosyl donor (I), Gly is the glycosyl group in which one or more hydroxyl groups on the sugar ring are protected by the protecting group; X is the oxygen, sulfur, or selenium atom; R is the alkyl group or the aryl group; the acceptor (II) is selected from carboxylic acids comprising one or more nucleophilic groups.

2. The glycosylation method according to claim 1, wherein the trivalent iodine reagent is selected from an iodine ylide reagent represented by a formula (IV-a) and imino iodide represented by a formula (IV-b); wherein $R^1$ and $R^2$ are each independently selected from alkyl acyl, aryl formyl, alkyl sulfonyl, aryl sulfonyl, alkoxy acyl, phenoloxy acyl; $R^3$ is a sulfonyl group, preferably a p-toluenesulfonyl group; Ar is an aryl group, preferably a phenyl group, a 2-methoxyphenyl group, or a 2-nitrophenyl group;

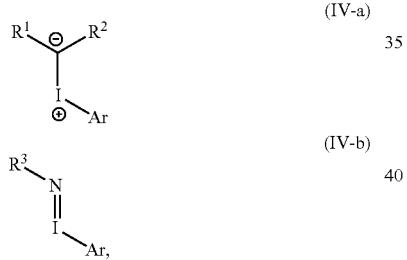

wherein
the transition metal catalyst is selected from materials comprising copper or rhodium; the acid is a Brønsted acid, a Lewis acid, or the acceptor (II) is the acid.

3. The glycosylation method according to claim 2, wherein the formula (IV-a) is a compound selected from any of following structures:

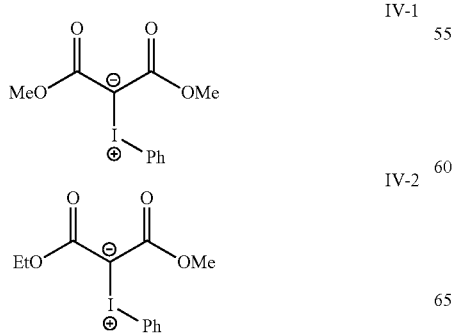

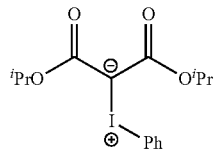

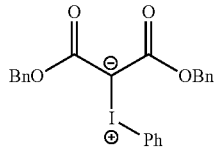

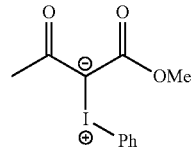

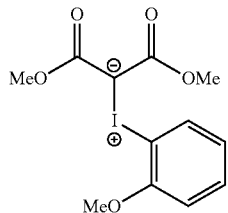

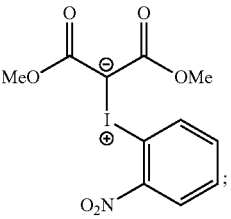

and
a structure of the formula (IV-b) is:

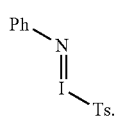

4. The glycosylation method according to claim 1, wherein in the glycosyl donor (I), the glycosyl Gly is selected from one of structures represented by a formula (I-a) or a formula (I-b), wherein $P^1$, $P^2$, $p^3$, and $P^4$ are each independently selected from hydrogen, an alkyl group, an alkoxy group, an acyloxy group, a siloxy group, a substituted amino group, a cyclic acetal group, a cyclic ketal group, or a glycosyl group;

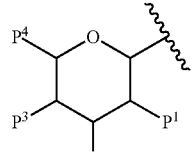
(I-a)
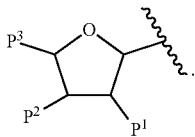
(I-b)
5. The glycosylation method according to claim 4, wherein a compound of the formula (I-a) is selected from any of following structures:
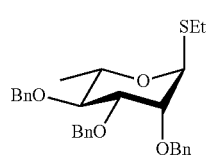
I-01
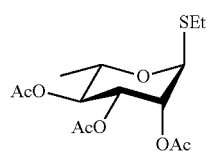
I-02
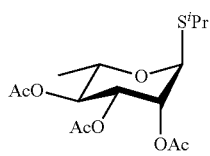
I-03
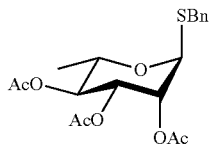
I-04
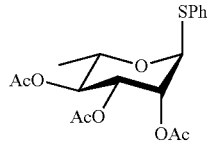
I-05
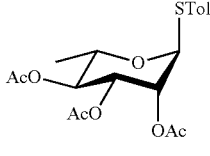
I-06
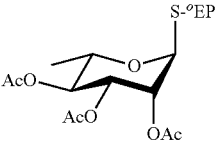
I-07
-continued
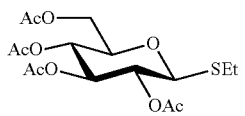
I-08
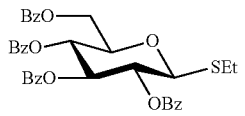
I-09
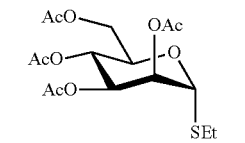
I-10
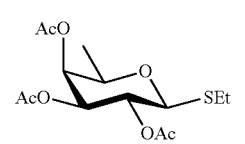
I-11
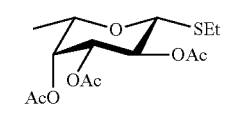
I-12
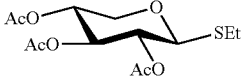
I-13
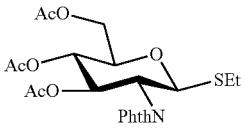
I-14
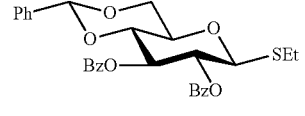
I-15
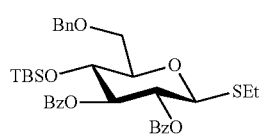
I-16
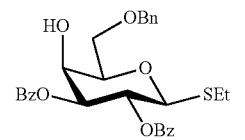
I-17
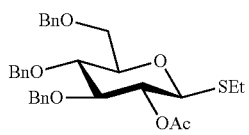
I-18
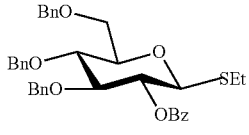
I-19

-continued
I-20 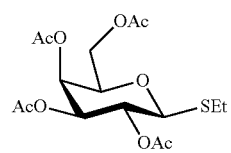
I-21 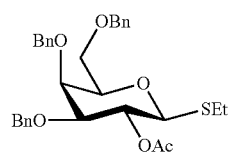
I-22 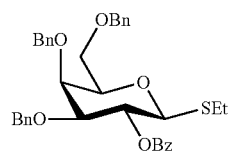
I-23 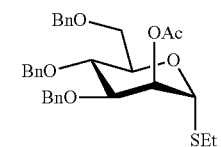
I-24 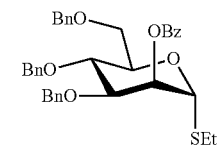
I-25 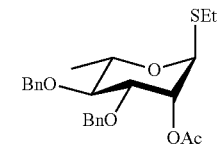
I-26 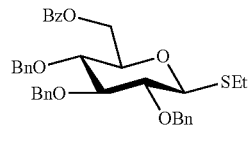
I-27 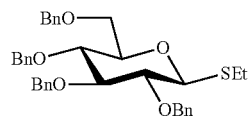
I-28 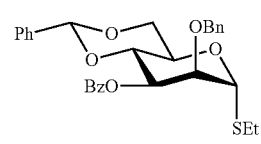
I-29 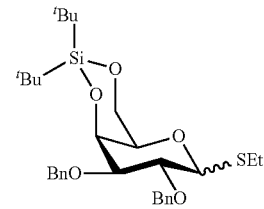
-continued
I-30 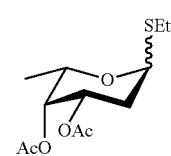
I-31 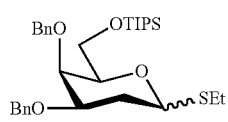
I-32 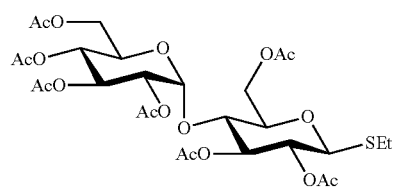
I-33 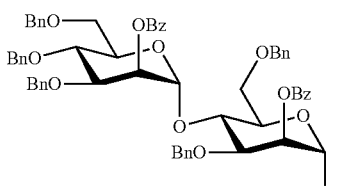
I-34 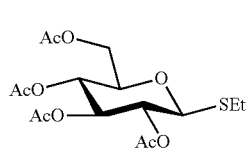
I-35 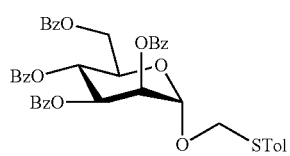
I-36 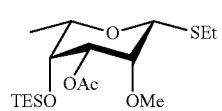
and
the formula (I-b) is a compound selected from any of following structures:
I-37
I-38

I-39
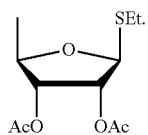
6. The glycosylation method according to claim 1, wherein the glycosyl acceptor comprising the one or more free hydroxyl groups is selected from a compound of any of following structures:
II-01
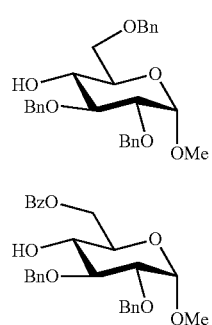
II-02
II-03
II-04
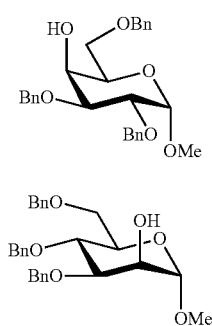
II-05
II-06
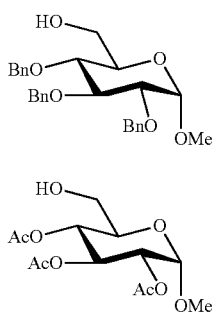
II-07
II-08
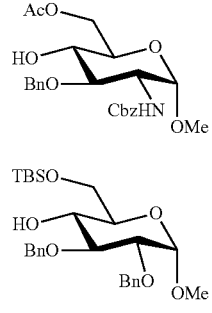
II-09
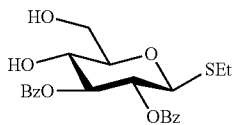
II-10
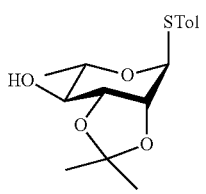
II-11
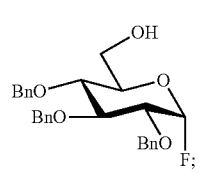
the alcohol or phenol acceptor is selected from a compound of any of following structures:
II-12
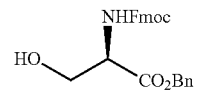
II-13
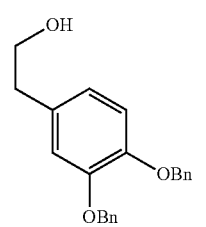
II-14
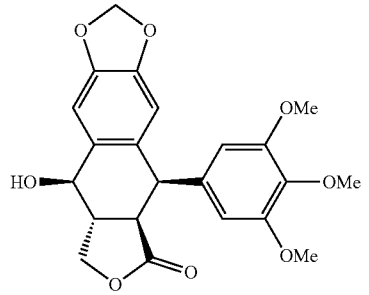
II-15
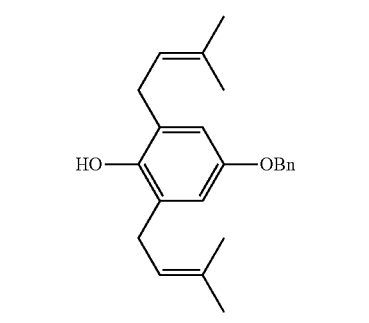

-continued

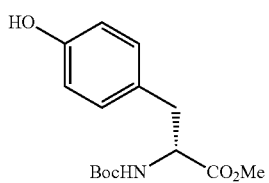
II-16

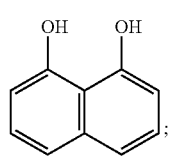
II-17 the flavonoid acceptor is selected from a compound of following structure:

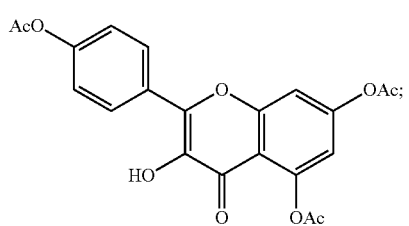
II-18 the carboxylic acid or phosphate acceptor is selected from a compound of following structure:

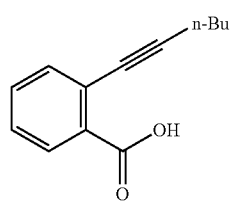
II-19

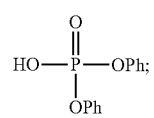
II-20 the pyrimidine acceptor is selected from a compound of any of following structures:

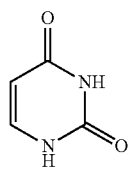
II-21

-continued

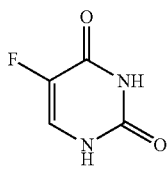
II-22

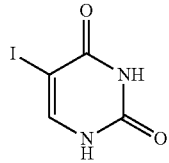
II-23

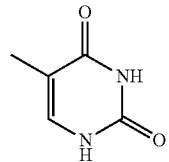
II-24

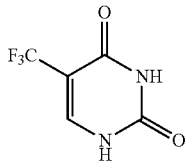
II-25

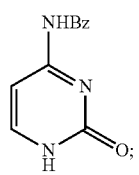
II-26 the purine acceptor is selected from a compound of any of following structures:

II-27

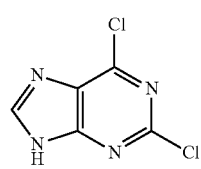
II-28

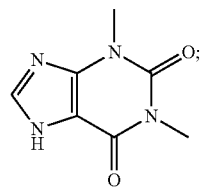
II-29 the amide acceptor is selected from a compound of any of following structures:

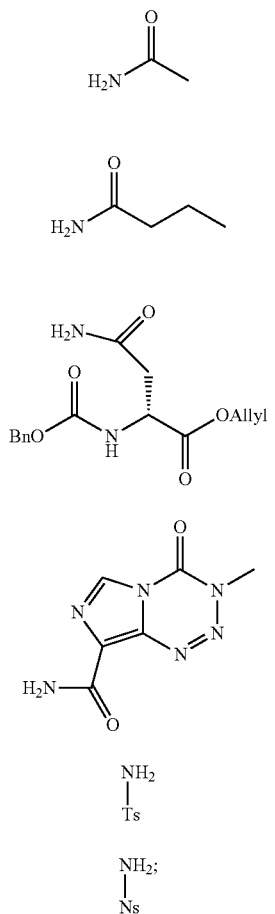

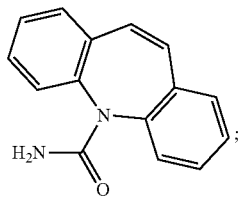

the sulfonamide acceptor is selected from a compound of following structure: ID

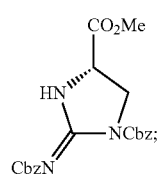

the guanidine acceptor is selected from following structure:

the arylamine acceptor is selected from a compound of following structure:

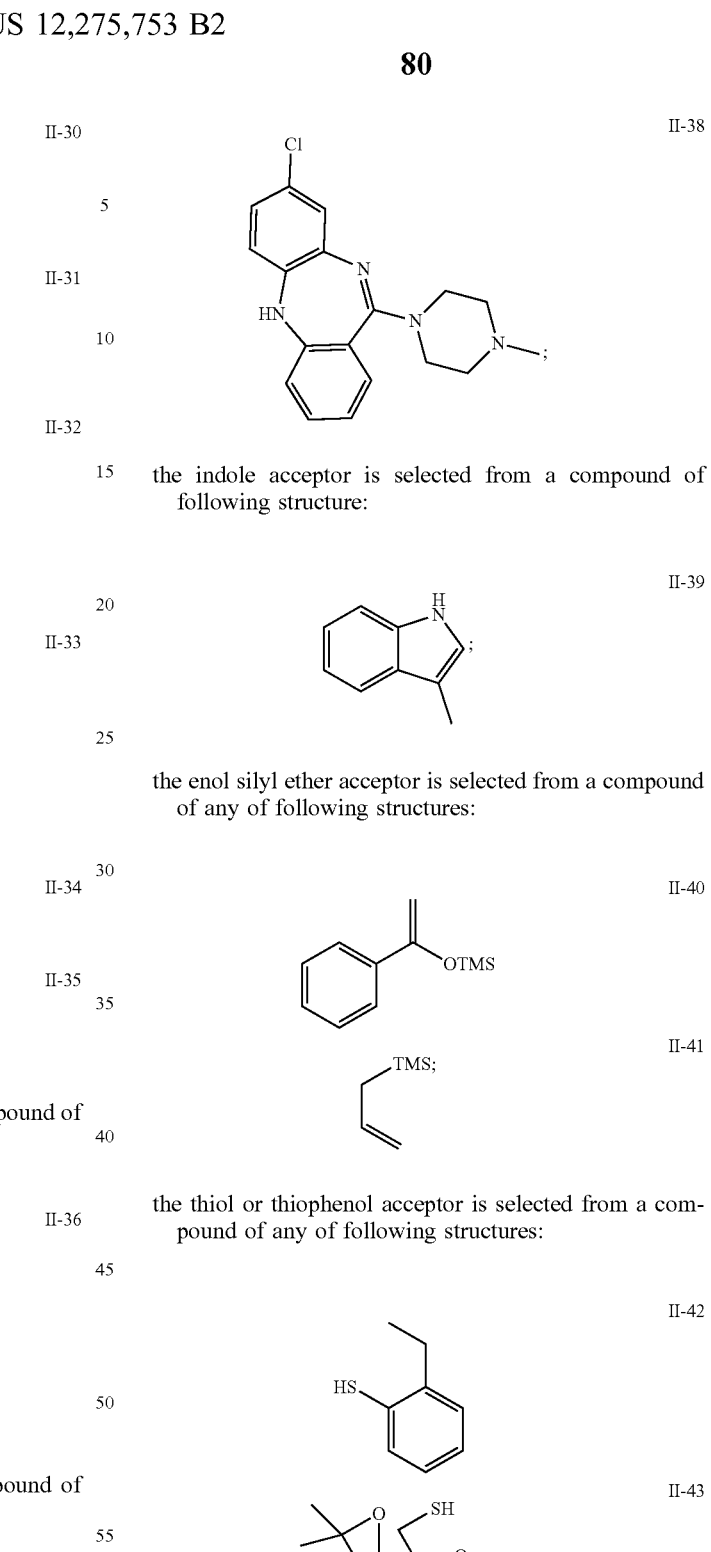

the indole acceptor is selected from a compound of following structure:

the enol silyl ether acceptor is selected from a compound of any of following structures:

the thiol or thiophenol acceptor is selected from a compound of any of following structures:

7. The glycosylation method according to claim 1, wherein the transition metal catalyst is cuprous chloride, cuprous bromide, cuprous iodide, cuprous bromide·dimethyl sulfide, cuprous tetrafluoroborate, cuprous trifluoromethanesulfonate, cuprous acetate, cuprous hexafluoroacetylacetonate ·1,5-cyclooctadiene, cuprous chloride [1,3-bis(2,6-diisopropylphenyl) imidazole-2-ylidene], cuprous diphenyl phosphate, cuprous thiophene-2-carboxylate, cupric chloride, cupric bromide, cupric acetate, cupric acetylacetonate, copper(II) hexafluoroacetylacetonate, copper(II) p-toluenesulfonate, copper(II) trifluoromethanesulfonate, copper(II) sulfate, cuprous trifluoromethanesulfonate toluene complex, rhodium (II) acetate dimer or rhodium (II) octanoate dimer.

8. The glycosylation method according to claim 1, wherein the acid is methanesulfonic acid, p-toluenesulfonic acid, camphorsulfonic acid, trifluoromethanesulfonic acid, trifluoromethanesulfonic acid-2,5-di-tert-butylpyridinium salt, trifluoromethanesulfonic acid-2,5-di-tert-butyl-4-methylpyridinium salt, pyridinium trifluoromethanesulfonate, diisopropylamine trifluoromethanesulfonate, tetrafluoroboric acid ethyl ether, bistrifluoromethanesulfonimide;

boron trifluoride etherate, tris(pentafluorophenyl)borane, trimethylsilyl trifluoromethanesulfonate, triethylsilyl trifluoromethanesulfonate, copper(II) trifluoromethanesulfonate, cuprous trifluoromethanesulfonate, or trityltetrakis(pentafluorophenyl)borate.

9. The glycosylation method according to claim 1, wherein a molar ratio of the acceptor (II) to the glycosyl donor (I) is 1:(0.5-2); and a molar ratio of the acceptor (II) to the trivalent iodine reagent is 1:(1-6).

10. The glycosylation method according to claim 1, wherein an amount of the transition metal catalyst is 0.01-10% of the acceptor (II); and an amount of the acid substance in the scheme 1 is 5-30% of the acceptor (II).

11. The glycosylation method according to claim 7, wherein the acid is methanesulfonic acid, p-toluenesulfonic acid, camphorsulfonic acid, trifluoromethanesulfonic acid, trifluoromethanesulfonic acid-2,5-di-tert-butylpyridinium salt, trifluoromethanesulfonic acid-2,5-di-tert-butyl-4-methylpyridinium salt, pyridinium trifluoromethanesulfonate, diisopropylamine trifluoromethanesulfonate, tetrafluoroboric acid ethyl ether, bistrifluoromethanesulfonimide; boron trifluoride etherate, tris(pentafluorophenyl)borane, trimethylsilyl trifluoromethanesulfonate, triethylsilyl trifluoromethanesulfonate, copper(II) trifluoromethanesulfonate, cuprous trifluoromethanesulfonate, or trityltetrakis(pentafluorophenyl)borate.

12. The glycosylation method according to claim 9, wherein an amount of the transition metal catalyst is 0.01-10% of the acceptor (II); and an amount of the acid substance in the scheme 1 is 5-30% of the acceptor (II).

* * * * *